(12) United States Patent
Berglund et al.

(10) Patent No.: US 7,029,689 B2
(45) Date of Patent: Apr. 18, 2006

(54) TUBULAR CONSTRUCT FOR IMPLANTATION

(75) Inventors: Joseph D. Berglund, Norcross, GA (US); Robert M. Nerem, Atlanta, GA (US); Athanassios Sambanis, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 378 days.

(21) Appl. No.: 10/143,554

(22) Filed: May 10, 2002

(65) Prior Publication Data

US 2003/0072741 A1    Apr. 17, 2003

Related U.S. Application Data

(60) Provisional application No. 60/289,961, filed on May 10, 2001.

(51) Int. Cl.
| | |
|---|---|
| *A61F 2/00* | (2006.01) |
| *C12N 11/02* | (2006.01) |
| *C12N 5/06* | (2006.01) |
| *C12N 5/08* | (2006.01) |
| *C12Q 1/02* | (2006.01) |

(52) U.S. Cl. .............. 424/423; 424/93.7; 435/29; 435/177; 435/395

(58) Field of Classification Search ............ 435/177, 435/178, 180, 182, 395, 29; 424/423, 93.7

See application file for complete search history.

(56) References Cited

U.S. PATENT DOCUMENTS

| | | | |
|---|---|---|---|
| 5,002,583 A | 3/1991 | Pitaru et al. ............ 623/66 |
| 5,521,087 A | 5/1996 | Lee et al. ............ 435/174 X |
| 5,676,698 A | 10/1997 | Janzen et al. ............ 623/8 |
| 5,863,531 A * | 1/1999 | Naughton et al. ......... 424/93.7 |
| 6,371,992 B1 * | 4/2002 | Tanagho et al. ......... 623/23.72 |
| 6,652,872 B1 * | 11/2003 | Nevo et al. ............ 424/423 |

* cited by examiner

*Primary Examiner*—David M. Naff
(74) *Attorney, Agent, or Firm*—Troutman Sanders LLP

(57) ABSTRACT

The present invention is directed to devices for repair, replacement or augmentation of soft tissues in an organism. The devices comprise cellular compositions comprising cells and preferably, structural proteins such as collagen or elastin. The devices can also be used in methods for testing the effects of agents on soft tissues.

15 Claims, 37 Drawing Sheets

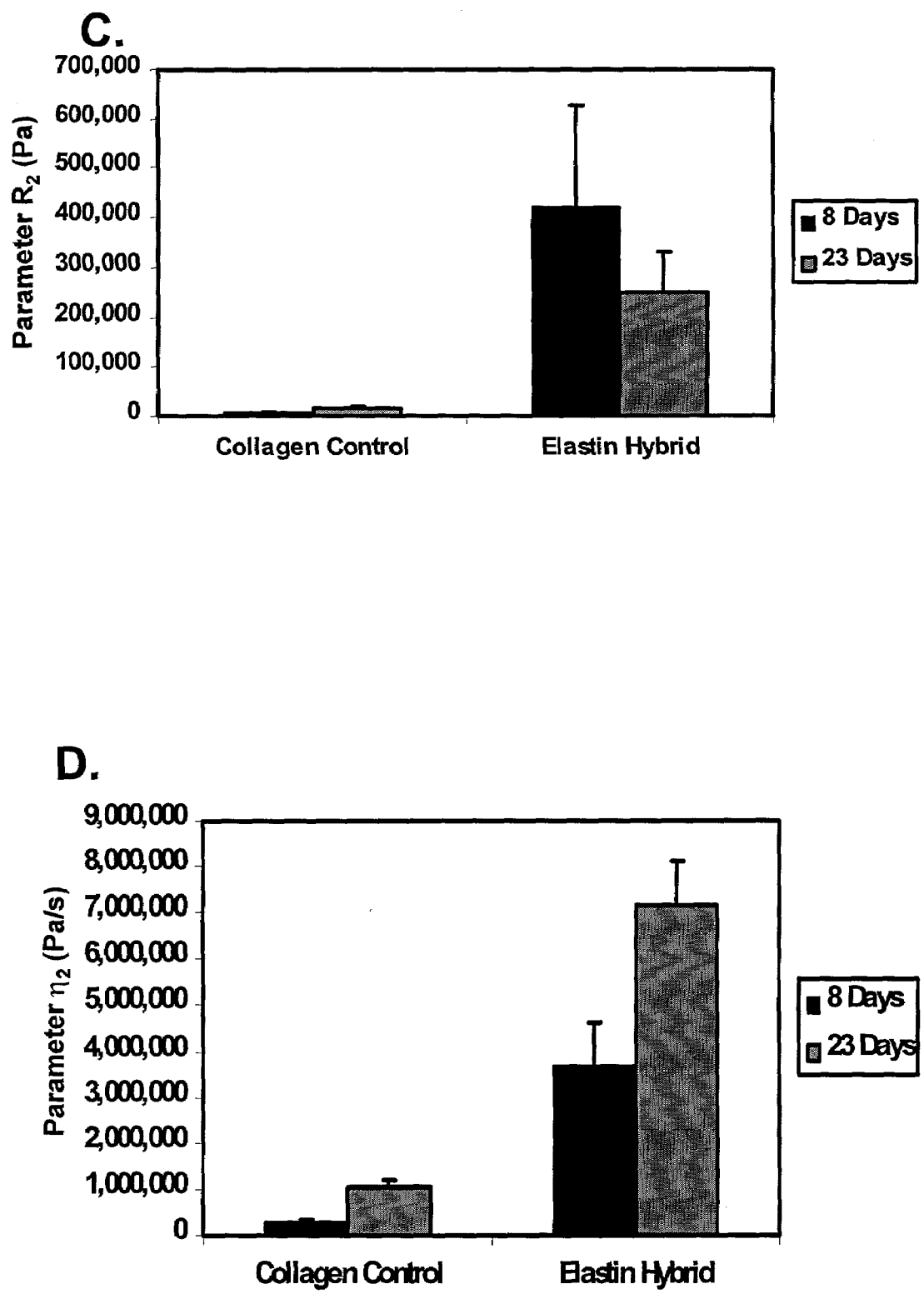
Figure 15 Con't

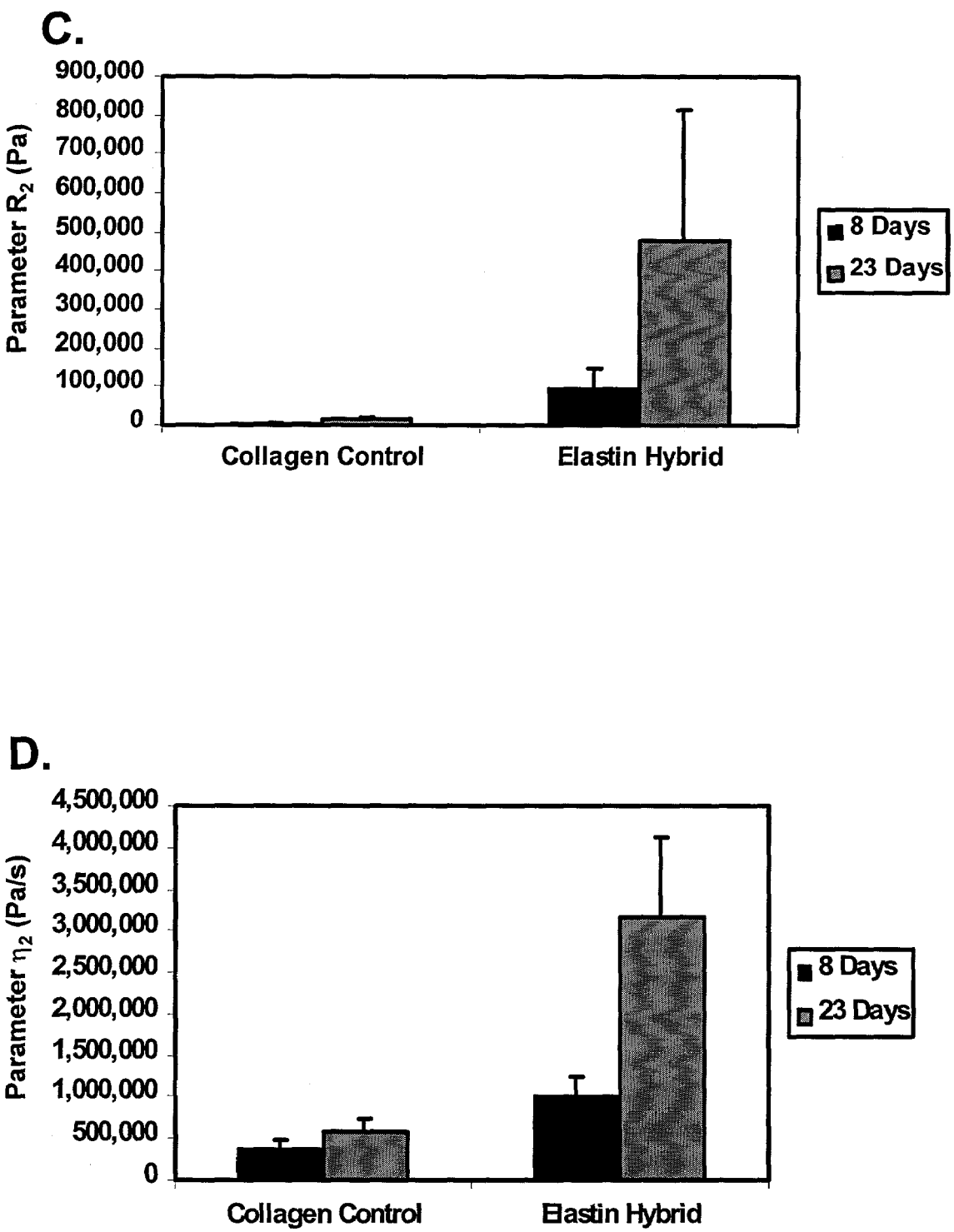
Figure 17 Con't

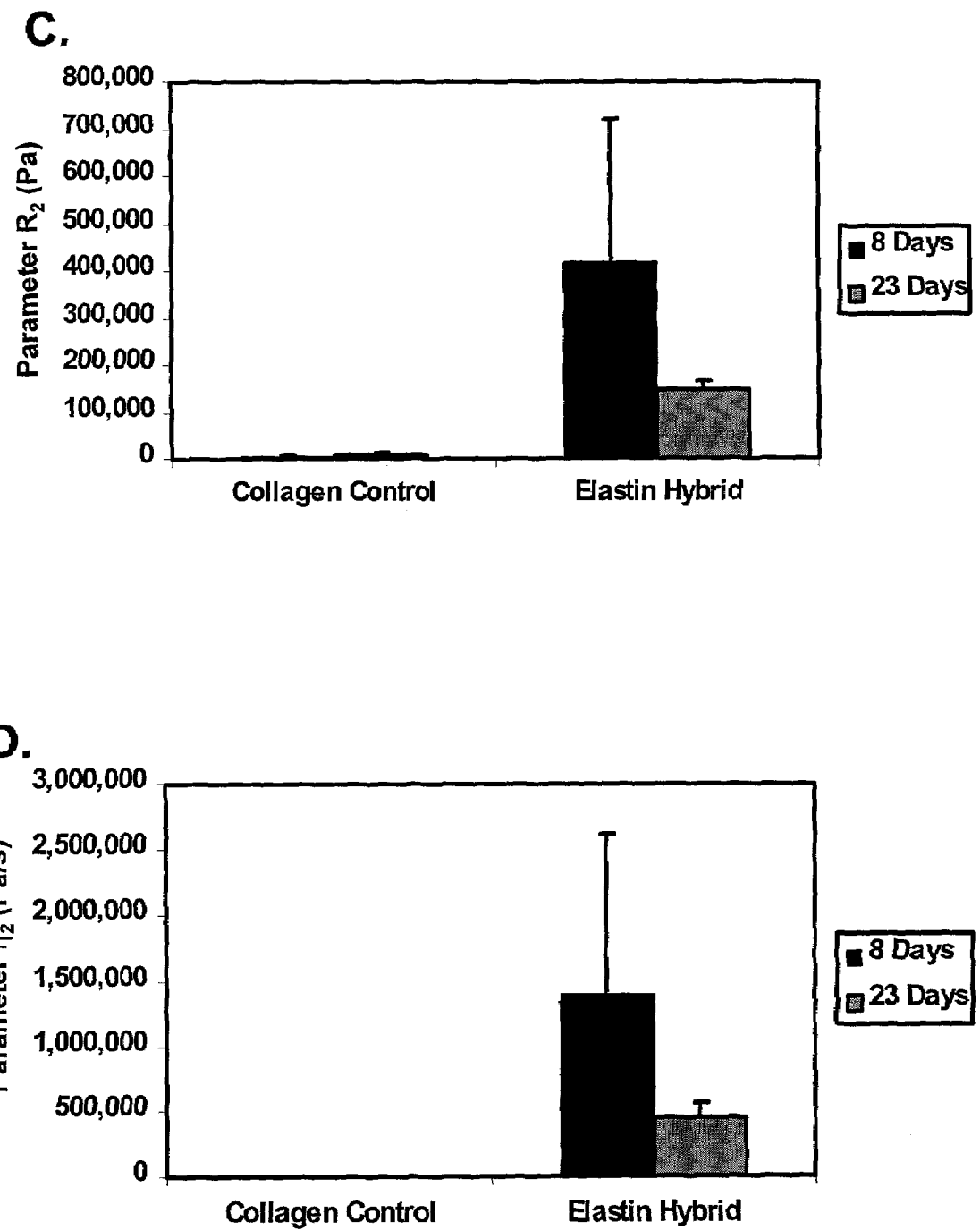
Figure 25 Con't

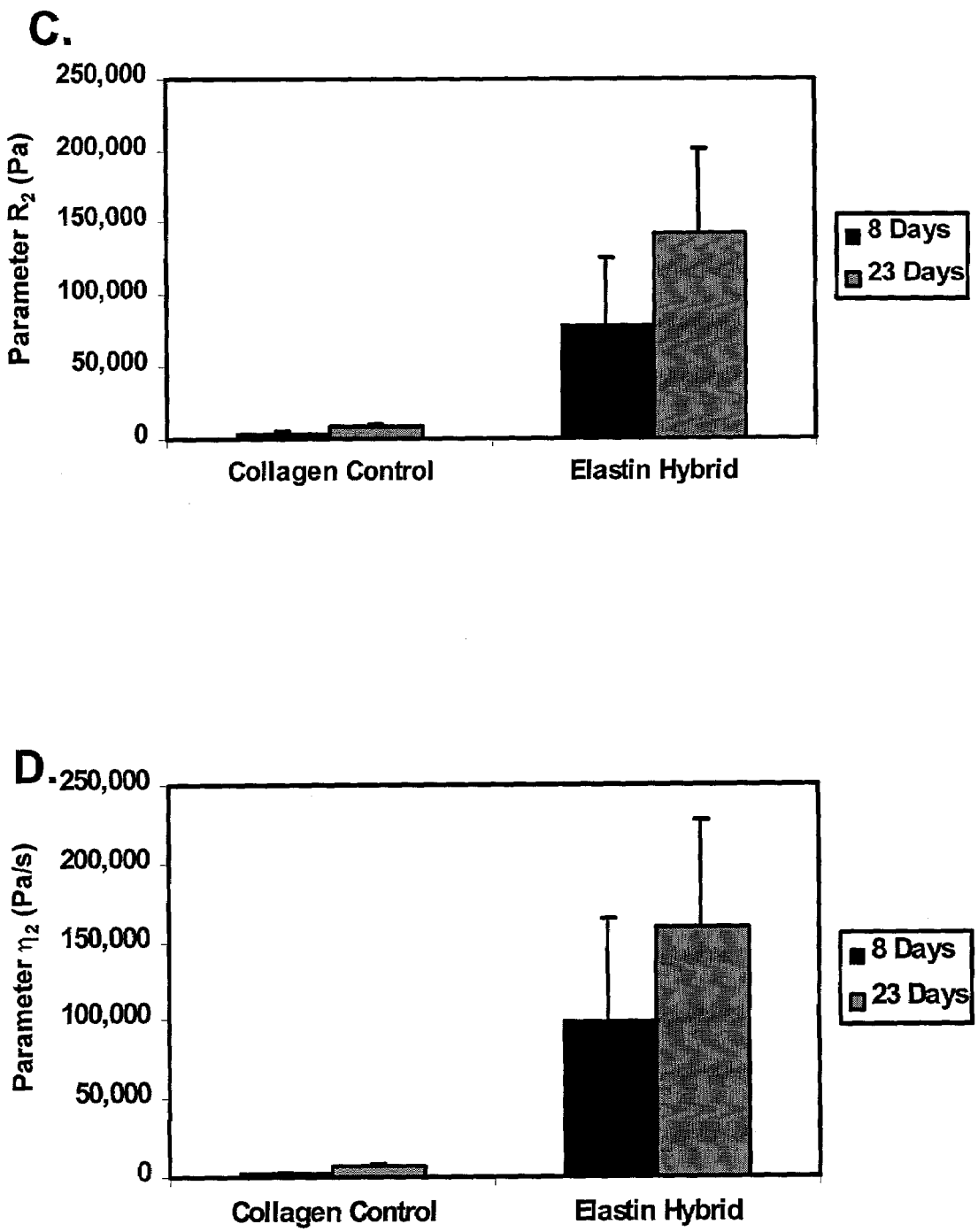
Figure 26 Con't

A.

B.

TUBULAR CONSTRUCT FOR IMPLANTATION

RELATED APPLICATIONS

This application claims priority to Provisional Application Ser. No. 60/289,961 filed on May 10, 2001.

FIELD OF THE INVENTION

The present invention relates to devices made from combinations of biological materials and methods of making and using such devices. In general, the present invention relates to methods of making soft tissue medical devices for uses in repair of damaged tissues and therapeutic agent determinations.

BACKGROUND OF THE INVENTION

In the United States alone, surgeons perform approximately 600,000 by-pass operations every year to provide repair to diseased arteries and restore blood flow to the heart. While autologous saphenous veins and internal mammary arteries have typically been utilized as conduits for these operations, there are a number of complications associated with these grafts. One complication arises when the patient cannot provide autologous tissues. The symptoms of vascular disease are frequently systemic causing many of these periphery vessels to be unsuitable for vascular replacement. Even when they are usable, donor site pain and morbidity complicate the operation. Furthermore, these grafts often slowly occlude due to intimal hyperplasia necessitating subsequent surgical interventions.

Ten to twenty percent of coronary artery by-pass patients require a second operation within ten years, and frequently even patients who could provide vessels initially do not have adequate vessels for follow-up operations. Although a number of attempts have been made to develop a synthetic small-caliber vessel, the demanding, low flow environment of the vasculature typically leads to thrombosis and occlusion shortly after implantation.

Soft tissue injuries or pathological conditions are often hard to treat because replacement tissues are not available or by adding a rigid member device to the soft tissue area only creates a more dysfunctional organ. For example, damaged lung tissue is generally not repaired, but is excised by surgery. Addition of a rigid material to the lung, in an effort to repair the lung would only further comprise the lung and gas exchange functions.

What is needed are devices that are capable of providing repair for soft tissues. Ideally, these devices would be immune-compatible alternatives to autologous tissues, possess suitable properties for surgical implantation, and function in the native environment of the repaired soft tissue. Additionally, what is needed are devices that mimic soft tissue that can be used, either in vivo or in vitro, in testing agents to determine the agents effects on native soft tissue. Such devices can be used for diagnostic or therapeutic purposes, as can agents that are determined to be effective.

SUMMARY OF THE INVENTION

The present invention comprises devices that are capable of being used in soft tissue environments. In particular, the devices comprise a support structure in combination with a cellular composition. For example, methods of making such a device comprise combining compositions of cells with a scaffold material to create a prosthesis capable of mimicking the function of native soft tissue.

A preferred embodiment of the present invention comprises methods to make hybrid material, small diameter tissue engineered devices such as blood vessels. A preferred blood vessel device comprises an isolated elastin scaffold support structure and a cellular composition comprising a protein gel composition such as collagen or fibrin, or mixtures thereof, and cells. Another preferred embodiment comprises a support structure and a cellular composition of protein gel composition wherein the cells have been altered. Alterations include transfection and expression of DNA constructs, for example, to provide proteins. The devices may also comprise agents that have effects on the device or the environment or that provide detection capability to the device.

Devices of the present invention can be made using synthetic or natural materials, or combinations of natural and synthetic materials. The natural materials can be provided by the same individual in whom the device will be used, or can be provided by others of the same or different species. The materials used in the devices may also be derived or altered using molecular biological techniques, such as gene manipulation, cloning, gene therapy or other methods known to those skilled in the art.

Methods of using the soft tissue devices of the present invention comprise methods for treatment of pathologies or disease states of soft tissues, found in organisms such as humans or animals. In particular, there are many applications for treatments of cardiovascular disease, such as coronary artery bypass and other small diameter vascular replacement procedures. Repair or replacement of any soft tissues is contemplated by the present invention including, but not limited to, bladder, lungs and vocal cords.

Other methods of using the devices of the present invention comprise using the device in a controlled environment as an assay system for determining the effects of agents on biological tissues. Use of the devices in an environment can also be for determinations of in situ measurements of the environment. For example, implantation of a vascular device can be used to determine the hemodynamic effects on vessels in healthy or pathological states. Additionally, the devices of the present invention can be used to provide agents to soft tissue structures. For example, a device implanted in the bladder could provide both tissue repair and through controlled release, provide therapeutic agents to prevent the growth of cancerous cells or attachment of bacteria.

DETAILED DESCRIPTION

Figure 1:
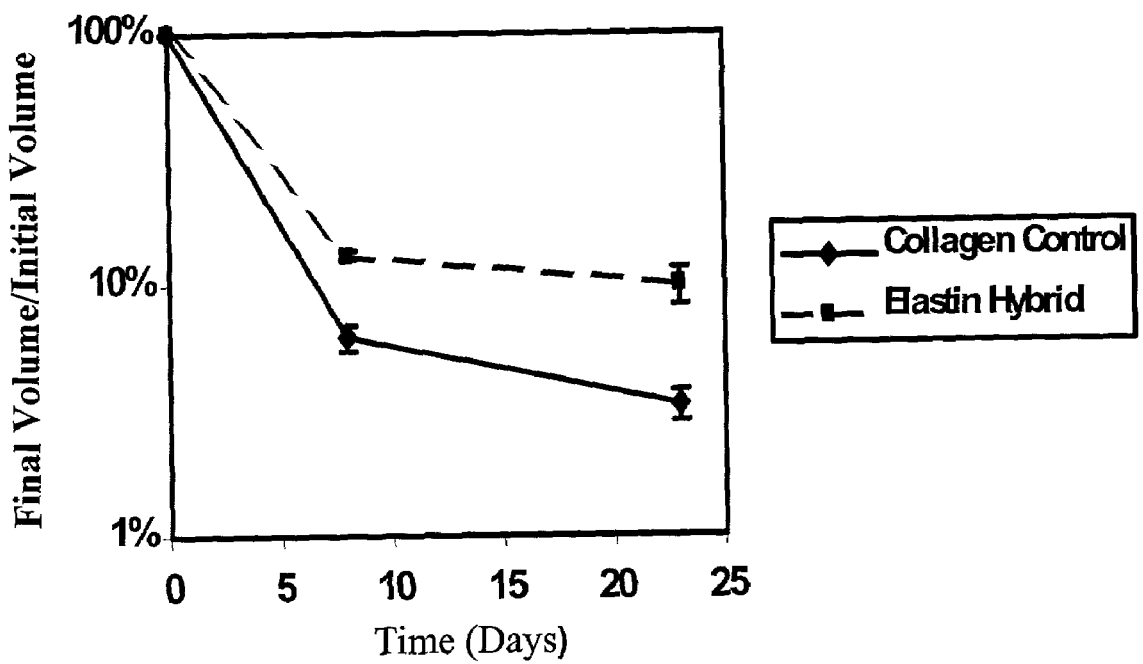
FIG. 1 is graph showing gel compaction in HDF constructs.

The present invention is directed to devices derived from biological materials for replacement of repair of tissues found in living organisms. Preferably, the devices have the mechanical, bioactive and biocompatible properties similar to the tissue being repaired or replaced. The present invention comprises soft tissue devices comprising a natural or synthetic support structure and cells. The present invention also comprises compositions for making the support structures and for treatment or maintenance of the cells. It is preferred that the devices comprise compositions of living cells so that cellular activities, such as remodeling of incorporated materials, continue in the device. In this sense, the soft tissue devices of the present invention are considered to be living tissue or alive, and thus, can function more like tissue found in a living organism.

Much of the description focuses on compositions and methods for making and using soft tissue devices that are used as vascular implants. The invention is in no way to be limited to such compositions, devices or methods of use, but is provided for illustrative purposes. It is contemplated by the present invention that soft tissue devices can be made using biological materials found in any type of soft tissue of living organisms and may or may not use cells derived from that particular soft tissue. Nonlimiting examples of soft tissues of living organisms include integument tissues other than hard bone, skin, membranes, mucosal membranes, organ linings or coverings such a meninges, periodontal material such as gum tissue, vocal cords, organs such as bladders, including but not limited to urinary or gall bladder, diaphragm, blood vessels, including large vessels to capillaries. It is contemplated that the devices of the present invention be used to repair or replace damaged tissues, and also that structures not normally found in the living organism be provided to add function or repair to the body. For example, if the urinary bladder of an organism is too diseased or damaged from trauma to be repaired by adding devices of the present invention to that organ, it is contemplated that repair also include providing a separate soft tissue device of the present invention that provides bladder function that works with or instead of the original bladder. The organism would then have two bladders, the minimally functioning original bladder and bladder functions provided by the soft tissue device. Additionally, the original organ's functions may be entirely replaced by the soft tissue devices of the present invention.

In general, the soft tissue devices of the present invention are living grafts that consist of biological materials and provide several benefits. The grafts interact with the physiological environment to elicit regenerative wound healing responses and to evoke both short-term and long-term remodeling adaptations. In vascular devices or grafts, the potential for low thrombogenicity properties allows these grafts to replace small diameter vessels and maintain patency in areas of low and even oscillatory blood velocity. When composed of autologous tissue, the soft tissue devices elicit a more mild immune reaction than that observed in the foreign body responses associated with other types implanted devices. Living devices or grafts also exhibit bioactivity and resistance to infection.

In addition to providing replacement and repair functions for living organisms, the present invention can also be used a living laboratory for studying physiological parameters and for identifying agents that effect soft tissues. As an example of vascular studies, a soft tissue device may provide scientists with a controlled system which could be used to study hemodynamics, atherosclerosis, and other cardiovascular pathologies. Agents can be administered to such soft tissue devices, incorporating cells and materials found in tissues of living organisms, to determine the effects of the agents on such tissues. The agents are administered to the devices in vitro or in vivo environments.

Many approaches to tissue engineering biological implant devices have focused on collagen-based strategies as collagen induces minimal immunological responses and sustains a majority of the mechanical load in many tissues. While these devices exhibit many desirable characteristics, they typically possess inadequate mechanical properties for implantation.

Although there are many properties that are desired in a successful soft tissue device, one to be considered is the mechanical properties of the device. For example, if a vascular soft tissue device is unable to withstand large interluminal pressures and harsh shear environment, it will ultimately fail. Likewise, a vascular soft tissue device is unsuitable for implantation if it is unable to withstand the millions of cyclic pulses that it encounters during its lifetime. Structural integrity, elasticity, and durability are characteristics to be considered in provided an adequate implant or replacement soft tissue device.

Significant efforts have been made to identify stimuli, such as cyclic stretching and ribose-mediated glycation, to augment the strengths of prior art collagen-based vascular grafts. Despite some favorable findings, the prior art grafts still possessed little elasticity and extensive development periods are required for many of these stimuli to take effect. These prior art collagen grafts did not include other biological materials found in soft tissues, such as elastin. Pathological conditions in living bodies result from elastin deficiencies such as aneurysms and other pathological vascular conditions.

In addition to collagen, elastin plays a major role in determining mechanical performance of native vessels. Elastin fibers can extend 50–70% under physiological loads, and depending on the location of the vessel, elastin content can range from 33–200% that of collagen. In spite of its role in maintaining proper vessel function, elastin had not been successfully used in vascular graft matrices prior to the present invention. Furthermore, the majority of attempts to assay for elastin production from cells in non-elastin-based grafts had detected little to no elastin.

Devices of the present invention preferably contain materials that provide functional and/or mechanical characteristics that mimic or at least are an adequate replacement for the original tissue found in the living organism. These materials may be naturally found in the original tissue or may be materials found in other tissues that provide adequate functional and/or mechanical characteristics for the tissue to be treated, replaced or studied. For the vascular soft tissue devices provided as illustration below, elastin is a material that provides functional and/or mechanical characteristics to the soft tissue device that is an adequate replacement for the original vascular tissue. In these examples, elastin that is naturally found in vascular tissue is provided in some embodiments and elastin that is provided from artificial sources is provided in other embodiments. In soft tissue devices used for other body tissues, the same or different materials can be provided as elastin is provided in these vascular embodiments.

A preferred embodiment of the present invention comprises a soft tissue device comprising a support structure and exogenous elastin proteins, fragments or combinations of proteins and fragments. Methods comprising addition of fragments of elastin into soft tissue devices provide high degrees of flexibility in the fabrication processes. By allowing the elastin to be added along with the other ECM (extracellular matrix) proteins, it is possible to control both the amount of protein inserted and the overall dimensions of the devices.

The exogenous elastins are added to the support structure compositions comprising the base material, such as collagen, and cells. An example how to make a support structure comprising collagen and cells is given in Example 2. In general, in making a support structure, collagen compositions are mixed with a desired cell population, which may be homogeneous or a heterogeneous cell population, i.e., the same or different types of cells, and allowed to form the desired shape. In these embodiments, collagen functions as an initial or base structural material, but it is contemplated that any natural or synthetic material can provide this initial or base structural material. In these embodiments, the cellular composition comprises collagen, elastin or similar material as the scaffold material, and the cells. In other embodiments described herein, the scaffold material is a natural or synthetic support structure, such as an elastin scaffold, and the cellular composition comprises collagen, elastin or similar material and cells.

The methods of making these exogenous elastin devices comprise methods of incorporating elastin into collagen-based vascular grafts. These methods are allowfor the amount and type of elastin incorporated to be easily adjusted and the methods can be modified to make other embodiments of soft tissue devices.

Soft tissue devices comprising exogenous elastins can be made in any desired shape necessary to provide for the repair, replacement or investigation. For example, in vascular devices, tubular shapes are preferred. In general, a vascular device comprises tubular-shaped devices seeded with HDFs and cultured as shown in Example 3. Gel compaction, histological staining, and mechanical testing can be conducted to determine if the device has the needed characteristics.

Any type of exogenous elastin can be added to the support structure composition. Elastin that is insoluble, soluble, peptides or fragments of elastin can be used. The elastin can be purified by methods known to those skilled in the art, including but not limited to, neutral extraction, alkaline extraction, or through non-degradative processes. Enzymes or proteases such as elastase can be used to form peptides or peptides can be formed through mechanical or chemical methods. Exogenous elastin can be added in any amount necessary to provide the needed mechanical or functional characteristics. Ranges of elastin concentration in the device comprise 0.0001 mg/ml to 50 mg/ml, preferably 0.001 to 50 mg/ml, more preferably 0.01 to 25 mg/ml, and most preferably 0.1 to 20 mg/ml. The amounts of collagen or other base material can be constant or can vary. The amount of collagen used can range from 0.0001 mg/ml to 50 mg/ml, preferably 0.001 to 50 mg/ml, more preferably 0.01 to 25 mg/ml, and most preferably 0.1 to 20 mg/ml. The cell type and initial concentration of cells added is determined by the type of device and function thereof. The concentrations of cells added as an initial amount to the cell composition range from $0.001 \times 10^6$ cells/ml to $100 \times 10^6$ cells/ml, preferably $0.01 \times 10^6$ cells/ml to $50 \times 10^6$ cells/ml, more preferably $0.01 \times 10^6$ cells/ml to $10 \times 10^6$ cells/ml, most preferably, $1.0 \times 10^6$ cells/ml.

Other embodiments contemplated by the present invention comprise chemical modifications of the elastin particles. Chemical domains, such as the fibronectin RGD amino acid binding sequence, induce cell-matrix binding. Once attached to the elastin fragments, the cells deposit their secreted ECM to form a functional network between the elastin components. Other embodiments comprise the introduction of crosslinking sequences which could then directly link the elastin fragments with the surrounding ECM. Rabaud et al. have patented an elastin-based product which covalently binds elastin to fibrin monomers in artificial biomaterial support structures (Rabaud, Lefebure Clement et al. 1993).

Though not wishing to be bound by any particular theory, it is theorized that following incorporation into collagen-based gels, the cells quickly remodel their surrounding matrices. It has been found in some embodiments, that incorporation of elastin fragments into the devices affects the degree of matrix compaction attained by the cells. In many embodiments, devices comprising exogenous elastin are thicker or have more bulk than similarly shaped devices without elastin. It is preferred that some cells incorporated in the devices remain alive, in a range of about greater than 10%, preferably greater than 25%, more preferably greater than 45%, most preferably greater than 51%. Histological and immunofluorescent staining, live-dead analyses and total DNA assays or other methods known to those skilled in the art are used to characterize the cells or other components in the devices and determine the viability of the cells. Mechanical tests, such as uniaxial tensile testing, ultimate stresses and linar moduli parameters, yield and failure energies, and other tests known to those skilled in the art can be used to determine the mechanical characteristics of the devices.

A preferred embodiment of the present invention comprises a composition comprising collagen, 2 mg/ml, exogenous elastin, 2 mg/ml, and HDF cells, $1 \times 10^6$ cells/ml. Methods for making such a composition is found in the Examples. The composition can be formed into any desired shape for use in repair, replacement and as an assay material.

A preferred embodiment of the present invention comprises devices comprising isolated natural scaffold materials or synthetic scaffold materials that mimic the characteristics of natural scaffolds. For example, a soft tissue vascular embodiment comprises isolation of intact elastin scaffolds from porcine carotid arteries. These scaffolds are combined with collagen gels and cells to provide hybrid elastin scaffold devices. By providing natural elastin scaffolds, a known quantity of elastic material is used, the fibers of the isolated scaffolds are organized and connected into functional structures as they would be in native arteries. While variability between donor animals produces slightly less control in terms of regulating the quantity and quality of the elastic scaffold, the mechanical performance characteristics are desirable for some applications. Additionally, these embodiments do not require cells to reorganize molecules or proteins to form the structure. Any shaped natural or synthetic scaffold is contemplated by the present device.

In a preferred method, natural elastin structures, such as arterial tissue, are isolated from an organism. An example of an isolation procedure is shown in Example 4, and such methods are known to those skilled in the art. The isolated natural structure is added to a cellular composition. Preferably, this cellular composition comprises one or more cell types. More preferably, the composition comprises one or more cell types and matrix materials such as collagen, fibrin, elastin, extracellular matrix materials or mixtures and combinations of matrix materials or fragments, polymers and peptides thereof. Ranges of collagen, elastin, fibrin or other base material can be constant or can vary and can include mixtures of several types of materials, including fragments, polymers, peptides, or modified fragments, polymers or peptides. The amount of these materials used can range from 0.0001 mg/ml to 50 mg/ml, preferably 0.001 to 50 mg/ml, more preferably 0.01 to 25 mg/ml, and most preferably 0.1 to 20 mg/ml. The cell type and initial concentration of cells added is determined by the type of device and function thereof. The concentrations of cells added as an initial amount to the cell composition range from $0.001 \times 10^6$ cells/ml to $100 \times 10^6$ cells/ml, preferably $0.01 \times 10^6$ cells/ml to $50 \times 10^6$ cells/ml, more preferably $0.01 \times 10^6$ cells/ml to $10 \times 10^6$ cells/ml, most preferably, $1.0 \times 10^6$ cells/ml. It is preferred that some cells incorporated in the devices remain alive, in a range of about greater than 10%, preferably greater than 25%, more preferably greater than 45%, most preferably greater than 51%. Histological and immunofluorescent staining, live-dead analyses and total DNA assays or other methods known to those skilled in the art are used to characterize the cells or other components in the devices and determine the viability of the cells. Mechanical tests, such as uniaxial tensile testing, ultimate stresses and linar moduli parameters, yield and failure energies, and other tests known to those skilled in the art can be used to determine the mechanical characteristics of the devices.

A preferred embodiment comprises a soft tissue device comprising an isolated elastin scaffold that has been incubated with a composition comprising collagen, 2 mg/ml and $1 \times 10^6$ HDF cells or RASM (rat aortic smooth muscle) cells. A method for making such a device is taught in Example 4.

Alternatively, the scaffold may be provided by a synthetic or manufactured structure, which would eliminate calcification or immunogenic problems. The synthetic structure may be made of natural or synthetic materials. A preferred soft tissue device comprises a synthetic structure made of Dacron that has been incubated with a composition comprising collagen and HDF cells or RASM cells. Further, the scaffold may be provided by collagen sleeves as described in Example 9. Such structures may have cross-linked components for further structural integrity. Methods of cross-linking materials is known in the art and includes treatments with glutaraldehyde, DHT and irridiation.

In yet another embodiment, the cellular composition comprises cells that have been modified or altered. A preferred modification is the transfection of the cells with recombinant DNA. Such transfection occurs by methods known to those skilled in the art using vectors of known types. Preferably, the expression products of such vectors include, but are not limited to, structural proteins, peptides or fragments such as elastin, collagen, fibrin, or ECM elements. In preferred embodiments, NIH/3T3 cells or primary human fibroblasts were transfected with DNA vectors comprising human tropoelastin cDNA which was under the control of the cytomegalovirus promoter. These cells can be used in addition to or as replacement for the embodiments of the devices described herein. It is further preferred that the cellular compositions comprising altered or modified cells comprise environmental factors, for example, that that help direct the formation of appropriate structures by the expressed proteins. For example, elastin fibers are found in a number of tissues throughout the body, but the structure and influence of the fibers differ significantly depending upon the specific location (Cleary and Gibson 1996). Concentric lamellar rings of elastic fibers are found in arteries, whereas elastic fibers in ligaments appear as solid, branching rod-like structures. In the cartilage of the ear and larynx, they appear as a mesh network of fine fibrils. Other tissues, such as the skin and the lungs, possess combinations of these structures.

During development, each of these tissues is exposed to a different environment where mechanical and biochemical cues direct the synthesis of the elastic fibers and other matrix components. Mechanical conditioning and other methods which induce circumferential alignment may also help to direct the assembly of elastic fibers towards the desired lamellar ring architecture. In the methods of making the devices comprising cellular compositions comprising altered or modified cells, it is also preferred that such methods comprise steps for simulating environmental conditions. For example, organization of expressed proteins may require a pulsatile mechanical motion for correct structural alignment of the fibers.

It is preferable that the modified or altered cells be capable of regulation so as to turn on or off the transcription, translation or expression of the exogenous DNA. Once sufficient quantities of the products of the exogenous DNA have been produced, it is preferable to down regulate or shut off recombinant expression. Failure to do so may result in a pathological state. In the case of recombinant expression, there are various methods that could be utilized to regulate production. For example, inducible plasmid systems could be employed to turn mRNA synthesis on and off based on chemical signals. The pMAM-neo vector uses a dexamethasone regulated MMTV promoter to control expression of target genes. Similarly, the Tet-on and Tet-off vectors are two alternative commercially available systems which have been reported to have high-level, regulated gene expression in response to varying concentrations of tetracycline (Clonetech, Palo Alto, Calif.).

A second method involves the use of a kill gene. Specific kill signals have been developed and can be engineered into the genetic makeup of recombinant cells. Once triggered, these systems will direct the transfected cells down the apoptotic pathway leading to cell death. After sufficient quantities of the expression product have been deposited into the vascular constructs, these kill systems could be employed.

Another method utilizes the natural down regulation of recombinant transcripts. When cells are transiently transfected with plasmid expression systems, the majority of recombinant DNA exists in the nucleus in the form of plasmids. As the cells divide, perfect replication and distribution of these plasmids to the progeny does not occur. Since unmodified cells typically divide quicker than their genetically altered counterparts, transfected cells are gradually overgrown and the level of recombinant expression drops. Even in the case of retroviral delivery systems, reduction in transcript production may occur over time. By timing the expression loss with the desired accumulation of products, regulated recombinant elastin production is achieved.

The present invention also contemplates cellular compositions comprising cells that normally express structural proteins or other desired products. For example, de novo elastin production could also be achieved using non-recombinant means. Various cell types such as bovine ligament fibroblasts (BLFs) and bovine ear chondrocytes have been shown to produce notable quantities of tropoelastin in culture. The tropoelastin from the ligament fibroblasts typically remains in its soluble form in the culture media while much of the elastin from the ear chondrocytes has been found to become incorporated into the extracellular matrix. Further methods comprise addition of growth factors and nutrient supplements for an upregulation of elastin production in cells. Insulin-like growth factor-1 (IGF-1) (Rich, Ewton et al. 1992) and transforming growth factor-β1 (TGF-β1) (Kahari, Olsen et al. 1992) induce an upregulation in elastin expression of cultured cells. Copper ions are necessary for proper lysyl oxidase activity and crosslinking of the elastin fibers.

The devices and compositions of the present invention may optionally comprise one or more agents. The agents may be biologically active agents that can be used in therapeutic applications or the agents may be agents that are useful in detection methods. In preferred embodiments, one or more agents are incorporated into the scaffold structure or alternatively, incorporated in the cellular composition. For example, a device of the present invention may incorporate an opaque substance so that after implantation to device can be monitored with noninvasive methods. Agents for treatments of biological conditions, including, but not limited to, chronic and acute diseases, maintenance and control of the immune system and other biological systems, infectious diseases, vaccinations, and hormonal maintenance and control. The agents contemplated by the present invention can be any compound, chemical, therapeutic agent, pharmaceutical agent, drug, biological factors, fragments of biological molecules such as antibodies, proteins, lipids, nucleic acids or carbohydrates; nucleic acids, antibodies, proteins, lipids, nutrients, cofactors, nutriceuticals, anesthetic, detection agents or an agent that has an effect in the body. Such detection and therapeutic agents and their activities are known to those of ordinary skill in the art.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

The articles and patents cited herein and in the priority application, and the priority application, are herein incorporated in their entireties.

EXAMPLES

Example 1

Cell Culture

Several types of eukaryotic cells, including neonatal human dermal fibroblasts (HDFs), the murine NIH-3T3 fibroblast cell line, and rat aortic smooth muscle cells (RASMs) were used to investigate the effects of elastin in vascular grafts. All eukaryotic cells were cultured and maintained under sterile conditions in tissue culture treated dishes and T-flasks. Media changes, subculturing, and other manipulations were conducted in laminar flow Class IIA/B3 biological safety cabinets (Forma Scientific, Marietta, Ohio). Unless indicated, cells were maintained at 5% $CO_2$ and 37° C. in humidified, water-jacketed incubators (Forma Scientific).

Cell culture medium was selected based on the needs of individual cell types and was replaced every 2–3 days to replenish nutrients and to remove waste products. When cultures became 90–95% confluent cells were trypsinized and split. Following a brief rinse in Hank's Buffered Salt Solution (HBSS) or 0.05% trypsin-0.53 mM ethylenediaminetetracetic acid (EDTA) in HBSS (Mediatech, Herndon, Va.) to remove $Ca^{++}$ ions and serum proteins, the cells were incubated with approximately 50 μl of 0.25% trypsin-0.53 mM EDTA in HBSS (Mediatech) per cm of growth area at 37° C. for 2–4 minutes. The flasks were tapped lightly and examined under an inverted microscope to ensure that the cells had detached. The trypsin-EDTA was neutralized with excess complete culture media (at least three times the trypsin solution volume). Unless otherwise indicated, cell suspensions produced by trypsinization were typically subcultured using 1:3 to 1:4 split ratios, incorporated into 3-D constructs, or frozen down for cryopreservation.

Cell populations were assessed using either a hemacytometer or a Coulter Multisizer II cell counter (Beckman Coulter, Fullerton, Calif.). Long-term storage of cells was performed using liquid nitrogen cryopreservation.

Human Dermal Fibroblasts (HDFs)

Passage one normal neonatal HDFs were purchased from Clonetics-Biowhittaker, Inc. (Walkersville, Md.). They arrived frozen in screw cap cryovials (~500,000 cells/vial) and were stored under liquid nitrogen until ready for use. Prior to purchase, the manufacturer performed safety studies to screen for HIV-1, hepatitis-B and hepatitis-C and characterization studies to ensure a negative expression of Von Willebrand factor, cytokeratins 18 & 19, and smooth muscle alpha-actin. Supplementary descriptions outlining the cell isolation and characterization methods are available on the Clonetics web site.

As recommended by the supplier, the cells were subcultured twice using a 3,500 cells/cm$^2$ seeding density and preserved in liquid nitrogen storage. At the point of confluency (just before harvest), HDFs typically reached a density of 30–40,000 cells/cm$^2$. The cells were grown in either a fibroblast-specific growth medium with a series of growth factor supplements supplied by Clonetics, or an alternative media formulation Dulbecco's Modified Eagle's Media (DMEM) (Mediatech, #10-017-CM) containing glucose (4.5 g/L), L-glutamine (4 mM) was supplemented with 10% Fetal Bovine Serum (FBS) (Sigma), penicillin (100 IU/ml), and streptomycin (100 µg/ml) and used to culture the cells. Experiments involving HDFs were conducted between passages five and eight.

NIH/3T3 Fibroblasts

The NIH/3T3 murine fibroblast cell line was originally obtained from American Type Culture Collection (ATCC) (Manassas, Va.). The adherent, highly contact-inhibited cells were established from NIH Swiss mouse embryo cultures using the same techniques as the original randomly bred 3T3s.

Cells were cultured at 10% $CO_2$, 37° C. using DMEM containing glucose (4.5 g/L), L-glutamine (4 mM), 10% FBS, penicillin (100 IU/ml), and streptomycin (100 µg/ml). At the point of confluency (just prior to subculturing), the NIH/3T3's typically reached a density of 100,000 cells/cm$^2$. Experiments involving NIH/3T3's were conducted anywhere from passage four to passage seventeen.

Rat Aortic Smooth Muscle Cells (RASMs)

RASMs were isolated from the thoracic aortas of male Sprague-Dawley rats (~350 g). They were cultured to passage two and frozen in DMEM+40% FBS+10% DMSO cryopreservation media. Upon thawing, the RASMs were cultured at 10% $CO_2$, 37° C. using DMEM containing glucose (4.5 g/L), L-glutamine (0.584 g/L), 10% FBS, penicillin (100 IU/ml), and streptomycin (100 µg/ml). At the point of confluency, RASMs typically reached a density of 150,000 cells/cm$^2$. Experiments involving RASMs were conducted between passages six and nine.

Example 2

A Collagen Support Structure

The use of reconstituted collagen as a cell scaffold was first described by Bell et al. in 1979 (Bell, Ivarsson et al. 1979). By 1985, the fabrication techniques had been modified to produce small diameter vascular constructs (Weinberg and Bell 1986). The basic protocol to make standard collagen-based tubular construct is described in this Example.

Collagen support structures were constructed from acid digested, Type I rat-tail collagen which had been dissolved in 0.02 N acetic acid. The collagen was obtained from Collaborative Biomedical Products (Bedford, Mass.) and typically varied in concentration from 3.49 to 4.30 mg/ml depending on the lot. Neutralizing the collagen solutions with a weak base, such as 0.1 N NaOH, caused the acid-solubilized molecules to spontaneously aggregate to form polymeric chains in a process known as fibrillogenesis. The rate of this reaction is dependent upon both temperature and pH, and components used in the construct were kept on ice during fabrication to facilitate thorough mixing. Table 3.1 describes the calculations used to determine the quantities of each component used in the collagen gels. Five times concentrated (5×) DMEM was added to buffer the solution while FBS was added to help the cells survive the fabrication procedure. Additionally, a slight excess of heat sterilized NaOH was used as recommended by the manufacturer to ensure proper gelation.

TABLE 3.1

Calculations for Fabrication of Basic Collagen Support Structures.

| Number of Constructs Made | Volume per Construct (ml) | Total Volume (ml) (Note: 10% excess was used) |
|---|---|---|
| N | 5.0 | $V_{Total} = 5.5 * N$ |
| Component | Volume Utilized | Comments |
| Type I Rat Collagen (Isolated at $C_{Col}$ mg/ml) in Acetic Acid (0.02 N) | $V_{Col} = V_{Total} * 2/C_{Col}$ | Initial target concentration 2.0 mg/ml |
| Autoclaved NaOH (0.1 N) | $V_{NaOH} = 0.22 * V_{Col}$ | Slight excess used to ensure proper gelation |
| FBS | $V_{FBS} = 0.1 * V_{Total}$ | Target concentration 10% by volume |
| 5× DMEM | $V_{5xDMEM} = 0.2 * V_{Total}$ | 5× concentration reduced to ~1× during fabrication |
| Cell-DMEM Suspension | $V_{Cell} = V_{Total} - V_{Col} - V_{NaOH} - V_{FBS} - V_{5xDMEM}$ | Flexible volume accounts for variability in $C_{Col}$ |

The assembly of cell-populated collagen support structures was initiated following the trypsinization of the cells which were to be incorporated into the graft. Populations of cells were estimated as previously described, and depending on the desired initial concentration of cells in each construct, an appropriate volume of suspended cells was centrifuged at 1000 rpm (165 g) for 5 minutes to pellet the cells. Typically, 1×10$^6$ cells/ml initial seeding densities were targeted. The cell pellets were resuspended in 1×DMEM and combined with a premixed solution of FBS, NaOH, and 5×DMEM. The mixtures were then combined with the dissolved collagen in 50 ml centrifuge tubes and quickly transferred into glass test tubes. Glass mandrel assemblies consisting of glass capillary tubes outfitted with rubber end stoppers were then inserted into the glass test tube to form tubular geometries.

Once the collagen gel solutions were in the molds, the test tubes were sealed with ventilated caps and incubated at 37° C. for 30 minutes. After the tubular constructs had gelled, the caps of the assembly molds were removed and lumens of the capillary mandrels were threaded with a thin metal rod to break the suction which could potentially be created during removal of the constructs from the mold. The constructs were then gently pulled from the glass test tubes without damaging the gels. Using sterile forceps, constructs were placed in 150-mm suspension petri dishes filled with ~140 ml of prewarmed culture media. Tissue culture media were entirely replaced every 5–7 days. Typically, two constructs were grown in each petri dish.

On occasion, the constructs were examined in a disk configuration. In these instances, the collagen gel solutions were poured into six-well tissue culture plates (2 ml per well) rather than the test tube/mandrel assemblies. The solutions were gelled at 37° C. for 30 minutes and covered with 4 ml of culture media. Every twenty-four hours, the constructs were carefully released from the tissue culture plastic to permit free compaction. Tissue culture media were entirely replaced every two days.

Example 3

Exogenous Elastin Fragments

Five types of elastins and elastin fragments were purchased from Elastin Products Company, Inc. (EPC, Owensville, Mo.) to investigate the effects of elastin fragments on vascular constructs. Two of the three insoluble elastins studied were procured from bovine neck ligaments. One was purified using the neutral extraction method described by Partridge et al. (EPC, #E60) (Partridge, Davis et al. 1955). Briefly, minced bovine *ligamentum nuchae* were rinsed in a 1% (w/v) NaCl solution. The samples were treated with a series of autoclave cycles (1 ATM, 45 min/cycle) to remove collagen and mucopolysaccharides followed by ethanol or 50% (v/v) ethanol-ether washes to remove the lipids. These processes were repeated, and ultimately, the samples were milled and filtered using a fine-mesh sieve. The resulting insoluble elastins exhibited alterations in their dye-staining character and adsorptive capacity for proteolytic enzymes compared to alkaline-digested specimens (Partridge, Davis et al. 1955). Gotte et al. also found that elastins which had been purified using this neutral isolation process possessed more free α-amino groups than those purified in alkaline conditions for extended periods of time. This was attributed to decreased hydrolytic damage to the peptide bonds. Little to no change in the number of interchain covalent crosslinkages was observed with the neutral extraction process (Gotte, Stern et al. 1963).

Alkaline isolations were performed according to the extraction methods described by Lowry et al. (Lowry, Gilligan et al. 1941). In short, tissue was minced and placed in a solution of 0.1 N NaOH overnight. The NaOH solution was replaced and the tissue was incubated for an additional two hours. The pH was neutralized, and the tissue was incubated in a alcohol/ether solution (3:1 v:v). The tissue was autoclaved at 50 psi for four hours, ground, and incubated in a boiling 0.1 N NaOH bath for twenty minutes. The first half of the procedure was designed to isolate both collagen and elastin proteins while the boiling NaOH solution was the key step in the elastin extraction. Analysis of hydroxyproline and amino acids were used to monitor the purity both during and after preparation. The final product was free of fat, muscle, collagen, and connective tissue and was reported to contain less than 0.01% insoluble residue following elastolysis.

A third method used a non-degradative process described by Starcher et al (Starcher and Galione 1976) to purify insoluble bovine aortic elastin (EPC, #SB87). A portion of the neutrally extracted elastin was further processed with hot oxalic acid and dialyzed to form a soluble, salt-free material capable of forming a coacervate at pH 5.0 and 37° C. (EPC, #ES12). Some of the alkaline extracted elastin was hydrolyzed with porcine pancreatic elastase, boiled and filtered to form a highly soluble fifth material (EPC, #CB573). This product which contained desmosines, isodesmosines, and Val-Gly-Val-Ala-Pro-Gly repeating peptides, exhibited a molecular weight range from 1,000 to 60,000 with ca. 60% passing a 3000 MWCO hollow fiber at 6 psi (manufacturer's data). The three insoluble elastins, which were obtained in 37–149 μm particles, were designated as Neutral Extraction, Alkaline Extraction, or Non-Degradative Elastin depending on the preparation method utilized. Similarly, the two soluble elastins were designated as either Oxalic Acid or Peptide.

The non-degradative method described by Starcher et al. used reagents that were specifically chosen to minimize the peptide cleavage observed in alkaline isolations (Starcher and Galione 1976). In addition to the autoclave and ethanol treatments used in the neutral isolation methods, trypsin, cyanogen bromide (CNBr) and β-mercaptoethanol (β-ME) were employed to further digest the samples. Elastins are unaffected by trypsin and chymotrypsin protease digestion. Furthermore, their lack of methionine residues and low cysteine contents make reduction agents such as CNBr and β-ME attractive isolation treatment candidates.

Soluble elastins were prepared from the products of the neutral elastin extraction procedure described above. Bovine neck ligament elastins were solublized with a hot oxalic acid solution, clarified, dialyzed, and lyophilized. The products formed a salt-free water soluble particulate which coacervated at pH 5.0 and 37° C. Exogenous, soluble elastin peptides were prepared from the products of the alkaline-mediated isolation process described above. Isolated insoluble elastins were hydrolyzed completely using porcine pancreatic elastase, filtered, and lyophilized. The resulting material, which varied in molecular weight from 1,000–60,000 Da, contained both the Val-Gly-Val-Ala-Pro-Gly repeat peptide and the desmosine and isodesmosine crosslink moieties.

The fabrication methods described in Example 2 for collagen constructs were modified slightly to create cell-seeded constructs containing exogenous elastin fragments. Each exogenous elastin was massed in a sterile weigh boat and combined with the acid-soluble rat tail collagen in a 50 ml centrifuge tube to form either a 1:1 or 1:5 collagen-elastin mixture (i.e. $C_{Elast}$ equal to $1 \times C_{Col}$ or $5 \times C_{Col}$). Consequently, as the collagen concentrations were diluted to 2 mg/ml, the concentrations of elastin fragments were likewise diluted to final concentrations of either 2 or 10 mg/ml. The mixtures were vortexed and placed on a shaker plate at 4° C. for at least 18 hrs prior to being used to make constructs. The soluble elastins dissolved readily into the 0.2 N acetic acid. The insoluble elastins formed a cloudy precipitate which tended to settle out of solution. These particles were resuspended through vortexing and/or pipetting just before the collagen-elastin mixtures were added to the constructs. Other than the formation of the collagen-elastin solution, the vascular constructs were prepared as previously described.

Three insoluble and two soluble forms of elastin were investigated. As described above, the insoluble elastins were purified by either neutral extraction, alkaline extraction, or through non-degradative processes and will be referred to as "Neutral", "Alkaline", or "Non-Degradative/Aortic", respectively. Hot oxalic acid processing was utilized to form a soluble material which will be referred to as "Oxalic/Oxalic Acid". Elastase was also used to form a soluble Val-Gly-Val-Ala-Pro-Gly penta-peptide repeat sequence. This second soluble material will be referred to as "Peptide". Fragments of elastin were added to collagen to form either 2 mg/ml (Low) or 10 mg/ml (High) concentrations. Due to the cost of the material, experiments involving Non-Degradative and Oxalic elastin fragments were only performed at low concentrations. Collagen-based constructs fabricated without exogenous fragments of elastin will be referred to as "Control" or "Collagen Controls". The concentration of collagen was kept constant (2 mg/ml) throughout all sample types.

Gel Compaction Data

Following their incorporation into collagen-based gels, the HDFs quickly remodeled their surrounding matrices. Macroscopically, constructs containing low and high concentrations of soluble elastin looked similar to collagen controls. Constructs fabricated with insoluble elastins, however, acquired a coarse appearance after the eight day culturing period as the particles of elastin could be seen throughout the translucent collagen gel. This effect increased with elastin concentration as the high insoluble constructs took on a yellowish, granular appearance.

Quantitatively, incorporation of elastin fragments into the constructs affected the degree of matrix compaction attained by the cells. After eight days of culture, insoluble elastins elicited a reduced degree of compaction (Insoluble-High vs. Control, $p<0.0001$; Insoluble-Low vs. Control $p<0.49$) while soluble elastins had little to no observable impact on construct compaction (Soluble-High vs. Control, $p<0.988$; Soluble-Low vs. Control, $p<0.30$). Constructs containing neutrally isolated insoluble elastin at low and high concentrations occupied 144.6% ($p<0.677$) and 211% ($p<0.015$) of the volume occupied by control constructs, respectively. Neutral-High constructs took up 146.3% ($p<0.64$) of the space that Neutral-Low constructs occupied. On average, constructs containing alkaline insoluble elastin at low and high concentrations occupied 124.7% ($p<0.995$) and 184.2% ($p<0.126$) of the volume occupied by control constructs, respectively. Likewise, Alkaline-High constructs took up 147.8% ($p<0.74$) of the space occupied by Alkaline-Low constructs. At low concentrations, insoluble elastins isolated using non-degradative processes did not elicit a statistically significant change in construct gel compaction. Soluble elastin digested with oxalic acid also did not have a statistically significant impact on the degree of compaction. While constructs containing soluble elastin peptides at low concentrations occupied 168.5% ($p<0.35$) of the volume as control constructs, this percentage dropped to 110.3% ($p<0.999$) at the higher concentrations.

The thicknesses of the construct walls followed similar trends as the overall gel compaction data. All five exogenous elastin fragments resulted in increased observed mean wall thicknesses compared to control constructs. These effects reached statistical significance in the Neutral-High (100% increase, $p<0.0020$) and Alkaline-High (79% increase, $p<0.014$) samples. The wall thicknesses in the other elastin samples did not differ statistically from control samples. On average constructs containing insoluble elastins were significantly thicker than controls (Insoluble-High vs. Control, $p<0.0001$; Insoluble-Low vs. Control, $p<0.166$). Constructs containing soluble elastins were statistically equivalent to controls (Soluble-High vs. Control, $p<0.993$; Soluble-Low vs. Control, $p<0.999$).

Histology and Viability Staining

While gel compaction analysis provides some information regarding overall cellular function, it only relates to macroscopic behaviors. In order to identify subtle similarities and differences between constructs with and without exogenous elastins, microscopic staining strategies were combined with some relatively simple molecular biological assays. Histological and immunofluorescent staining of sectioned tissues was used to characterize cell and matrix organization throughout the constructs while live-dead analysis and total DNA assays were attempted to characterize cell viability and proliferation.

Histological examination of the constructs using Haematoxylin and Eosin Y staining (H&E) colored nuclei and other cellular components blue and the extracellular matrix pink. From these micrographs, it was seen that while cells are dispersed throughout the entire thickness of the constructs, a large concentration of cells has migrated to or proliferated on the outer wall. In both collagen controls and samples containing soluble elastins, the walls of the constructs were comprised of diffuse networks of fibers which had been colored faint pink. The samples containing insoluble elastins also exhibited the dense outer layer of cells surrounding a weakly stained network of fibers, but in addition to this, the elastin fragments presented as dark, geometric particles throughout the walls of the constructs. As the initial concentrations of insoluble elastin were increased from 2 to 10 mg/ml, the concentration of particles increased proportionally.

Immunostaining of sectioned tissues using a murine BA-4 monoclonal primary and a FITC-conjugated secondary was utilized to identify elastin components in the matrix. In constructs containing insoluble elastin fragments, non-uniform particles were evenly distributed throughout the wall of the construct and presented as a striking green. No staining was visible in either the samples containing soluble elastins or the collagen controls. Verhoff's stain, a histological marker that preferentially dyes elastin and elastic fibers, resulted in similar findings as in the immunofluorescent assays. Cellular components and the "crystalline-shaped" particles in the constructs containing insoluble elastin presented dark black while none of the soluble elastin in either the Oxalic or Peptide constructs was seen. These findings may indicate that the soluble elastins diffused out of the constructs during the course of the experiments or they may simply result from the fact that the processing steps involved in isolating the soluble elastins removed the antigen binding sites from the materials.

Cellular viability in constructs containing elastin fragments was assessed through live-dead staining. All constructs had a high ratio of viable (green) to nonviable (red) cells. In control constructs and constructs containing soluble elastins, the cells were distributed throughout the entire matrix. In constructs containing insoluble elastin fragments, irregularly-shaped regions were seen which did not contain any cells. The sizes and shapes of these voids were consistent with the particles visualized in the histological staining, and consequently they were supposed to be regions of insoluble elastin fragments which prevented cellular ingrowth. The outer edge of each construct contained a layer of viable cells as seen in the H&E stains.

In addition to its role in maintaining the mechanical integrity of blood vessels, elastin has also been shown to have biochemical effects on cell behavior. Ito et al. have shown that cells seeded in collagen gels containing soluble α-elastin components exhibit decreased migratory and proliferative capabilites (Ito, Ishimaru et al. 1997; Ito, Ishimaru et al. 1998). While no overt differences in overall cell populations were detected in the sectioned histological stains, a Hoescht total DNA assay was attempted to identify the number of cells in each type of construct. Control samples which did not contain exogenous elastins demonstrated an average increase in cell count over an eight day culturing period. When this assay was extended to constructs containing soluble and insoluble elastin fragments, the elastin materials elicited positive signal readings. Furthermore, since it was not possible to determine how much elastin diffused out of the constructs with culturing, the Hoescht DNA assay was not able to ascertain the number of cells present in each construct.

The findings described in this section demonstrate some of the potential biochemical effects that elastic fibers can have on vascular constructs. Although issues such as cell viability, cellular migration and proliferation, and ECM organization are important considerations to address when developing a tissue engineered blood vessel replacement, they were only a small part of the overall goals of these studies. While additional experiments and assays could be have been attempted to elucidate these effects, the bulk of the research efforts in these studies focused on exploring the interactions between elastin and the mechanical properties of the constructs.

Uniaxial Tensile Testing

Uniaxial tensile testing was conducted on ~5 mm ring samples to assess the overall strengths of constructs containing fragments of exogenous elastin. Both collagen control samples and samples containing elastin fragments exhibited similar general stress-strain profiles. They possessed a characteristic "toe-region", followed by a quasi-linear regime which eventually plateaued into a region of yielding and deformation before ultimate failure.

Ultimate Stresses and Linear Moduli

In general, insoluble elastins resulted in decreased ultimate tensile stresses (Insoluble-Low vs. Control, $p<0.72$; Insoluble-High, $p<0.009$) while soluble elastins did not (Soluble-Low vs. Control, $p<0.75$; Soluble-High, $p<0.201$). Constructs containing neutrally isolated insoluble elastin at high concentrations exhibited a 45.0% ($p<0.09$) decrease in the observed mean UTS compared to controls. Similarly, constructs containing alkaline-digested elastins at high concentrations exhibited a 48.2% ($p<0.07$) decrease in the UTS parameter. No other individual treatment levels approached statistical significance.

Unlike the UTS trends, the observed mean linear moduli tended to increase in the presence of insoluble elastins (Insoluble-Low vs. Control, $p<0.395$; Insoluble-High vs. Control, $p<0.62$) while giving mixed results in the presence of soluble elastins (Soluble-Low vs. Control, $p<0.62$; Soluble-High vs. Control, $p<0.999$). While the overall trends in the linear modulus may have directed upward, no statistically significant differences were observed in with any of the individual treatment levels or elastin groups.

It is likely that many of the observed trends would reach significance if the sizes of the sample sets were increased. Since the uniaxial tensile testing measurements were based on the original, unstressed dimensions of the samples, some decreases in peak stresses would be expected and could be attributed to the differences in the thicknesses of the sample walls. These explanations, however, would not account for all of the observations, such as the mixed trends observed with some of the soluble elastins. Still, it is important not to read too much into the data as most of the differences were not statistically significant.

Yield and Failure Energies

In order to obtain some further information regarding the effects of exogenous elastins on the overall strengths of the constructs, the areas under the uniaxial tensile test stress-strain curves were utilized to evaluate construct toughness. By normalizing the data by the length of sample tested, it was possible to estimate the amount of energy needed to be applied to each construct to bring it to the point of yielding and to the point of failure. The ratios of these yield and failure energies were used to identify the mode by which the samples failed.

In general, soluble and insoluble elastins did not have a statistically significant impact on either the yield or failure energies. Of all the treatment levels investigated, only the Peptide-Low ($p<0.81$) and Peptide-High ($p<0.13$) exhibited p-values less than 0.9 when the yield energies were compared with the collagen control samples. Similarly, only the Peptide-High ($p<0.76$) exhibited a p-value less than 0.9 when the failure energies were compared with the collagen control samples.

It was found that incorporating either soluble (Soluble-Low, $p<0.056$; Soluble-High, $p<0.93$) or insoluble (Insoluble-Low, $p<0.64$; Insoluble-High, $p<0.22$) exogenous elastins into the collagen constructs caused the observed mean ratio to increase. A larger ratio indicated a larger degree of plasticity. While none of the parameters reached statistical significance, the values tended to increase indicating that exogenous elastin fragments may cause the constructs or soft tissue devices to endure more plastic deformation prior to failure. As used herein throughout the specification, the terms construct and device are interchangeable.

Example 4

Intact Elastin Scaffold

Intact elastin scaffolds were procured from the arteries of adult pigs (3–5 mm ID). After the pigs were shocked, exsanguinated, and skinned, an incision was made from the top of the sternum to the chin using a scalpel. The tissue was separated with retractors and the left and right carotid arteries were removed using surgical scissors and forceps. Excess blood was washed off each vessel with a phosphate buffered saline (PBS) solution (pH 7.4) containing antibiotic-antimycotic (Gibco BRL, Gaithersburg, Md.). Saline was also infused through the lumen to remove any blood clots. Once cleaned, the arteries were immersed in fresh saline and stored on ice.

As summarized in Table 3.2, the elastin scaffolds were isolated from the porcine carotids using a series of enzymatic, chemical, and thermal treatments. Briefly, arteries were incubated in a pH neutral sodium phosphate buffer solution for three twenty-four hour cycles to thoroughly clean each vessel. Excess adventitia was then removed using surgical scissors and forceps, and the arteries were cut into 1.25" long segments and loaded onto the capillary tube mandrel assemblies. Arterial segments were then immersed in 100 ml of deionized (DI) water and autoclaved for sixty minutes at 17.4 PSI. Upon completion of each cycle, the water was removed while still hot and replaced. The arteries were then reautoclaved for a subsequent sixty minutes. A total of five autoclave cycles were conducted. Arterial segments were then placed in a 0.0133% trypsin-tris buffer solutions and incubated at 37° C. for 18 hrs.

Following the enzymatic digestion, the segments were incubated in a cyanogen bromide (CNBr)-formic acid reducing solution for six hours. Further digestion was performed overnight in a β-mercaptoethanol, urea solution. A twenty-four hour ethanol incubation was used to help remove contaminant lipids and to sterilize the scaffold segments. Upon the introduction of ethanol, the scaffolds were handled aseptically. Finally, three twenty-four hour washings were performed in sterile PBS at 4° C. to remove residual ethanol. At this point, the isolated elastin scaffolds were ready to be incorporated into TE vascular grafts.

TABLE 3.2

Isolation Procedure for Intact Elastin Scaffolds.

| Procedure | Duration | Comments |
|---|---|---|
| Sodium phosphate buffer washes (0.05 M, pH 7.6) | 3 × 24 hrs @ 4° C. | Slight agitation |
| Autoclave treatments (100 ml DI water/segment) | 5 × 60 min @ 17.4 PSI | DI water was replaced while hot (immediately after completion of cycle) |
| Trypsin-tris buffer digestion (0.1 M, pH 8.2) Containing 0.02 M $CaCl_2$ | 18 hrs @ 37° C. | 0.0133% trypsin (w:v) |
| DI water rinses | 3 × 5 min | |
| Cyanogen bromide-formic acid digestion | 6 hrs @ room temperature | 2% cyanogen bromide (w:v) Slight agitation |
| DI water rinses | 3 × 20 min | |
| β-mercaptoethanol-tris buffer digestion (0.05 M, pH 8.0) Containing 6 M urea | 18 hrs @ room temperature | 0.5% β-mercaptoethanol (v:v) Slight agitation |
| DI water rinses | 3 × 20 min | |
| Ethanol incubation | 24 hrs @ 4° C. | ~40 ml/segment Sterile conditions maintained from this point onward |
| PBS washes (pH 7.4) | 3 × 24 hrs | ~40 ml/segment Slight agitation |

As with the exogenous elastin fragments, the fabrication process described in Example 2 was modified to incorporate isolated elastin scaffolds into the collagen gels. Cell-seeded collagen gels were prepared and transferred into the tubular molds as previously described. The mandrels and isolated scaffolds were then inserted into the molds and elevated up and down to allow the collagen gel to infiltrate regions on both sides of the elastin scaffold. While the majority of the collagen gel resided on the outside of the elastin scaffold, small gaps between the elastin and mandrel permitted some collagen to infiltrate the inner lumen of the scaffold. Additional steps were performed as previously described.

Constructs fabricated with isolated elastin scaffolds were studied to examine the effects of known amounts of highly structurally organized elastic fibers on the properties and function of vascular grafts. Experiments investigating gel compaction, histological staining, and mechanical testing were conducted. The results described correspond to experiments performed on tubular constructs seeded with either HDFs or RASMs and cultured statically on 3-mm glass mandrels for either eight or twenty-three days. Constructs containing an isolated arterial elastin scaffold are generally referred to as "Elastin Hybrids" while those constructed without the elastin component are referred to as "Collagen Controls". While complete studies on both the rat and human cells were performed, the experiments were designed to explore effects between treatment levels and culturing periods rather than between cell types. Consequently, the HDF and RASM data in the subsequent sections are presented separately. Occasionally, when the results observed for the respective cell types were markedly different, cross-comparisons were noted to indicate behaviors in which the cell types may be functioning differently.

Elastin Scaffold Isolation Studies

It is desired that purification methods capable of removing ECM proteins and cellular debris from native arteries while leaving the elastin fiber network relatively intact. Approaches modified slightly from those originally described by Starcher et al. (Starcher and Galione 1976) were selected based on their ability to digest collagens, lipids, and proteoglycans without damaging the elastic matrix.

Rates of protein removal were assessed through a Bicinchoninic Acid (BCA) colorimetric assay (Pierce, Rockford, Ill.) on the processing/digestion solutions. Bovine serum albumin (BSA) was used as a standard. Substantial quantities of protein were removed in the first few sodium phosphate rinses as serum proteins and other clotted blood components were washed away. Similarly a substantial quantity of protein was removed in the initial autoclave cycle. Diminishing amounts of protein removal were observed in subsequent sodium phosphate rinses and autoclave incubations as the effects of the treatments decayed. While a third spike in protein removal was observed during the trypsin digestion, samples from the cyanogen bromide and β-mercaptoethanol digestions were not analyzed.

Weight loss during arterial processing was assessed to help determine the amount of ECM and cellular debris lost during each treatment step. After blotting scaffolds on piles of absorbant wipes (30 seconds each side) to remove excess fluid, each sample was weighed on balance and normalized to their original weight prior to the first autoclave cycle. Sample weight initially increased to 136% of the original values as the constructs swelled during the initial autoclave treatments. This was followed by a sharp decrease in weight as the constructs dropped to 27% of their original mass in subsequent autoclave cycles. Although it was not measured at each step, weight loss continued with additional treatments until the constructs eventually dipped below 15% of their original mass. As described earlier in Table 2.1, elastin comprises between 15 and 25% of the dry, defatted tissue in small diameter arteries. The water and fat in these tissues typically range from 65 to 75% of the total weight (Dobrin 1997). Since the isolated elastin matrices were not dehydrated prior to each weight measurement, it is difficult to make direct comparisons between the various treatments. Nevertheless, the values are similar enough so as to be roughly compatible with one another.

Macroscopically these isolated elastin scaffolds differed significantly from their undigested counterparts. When arterial sections were stained using BA-4 monoclonal anti-elastin antibodies, the elastic structures throughout the arterial wall could be visualized. A wavy internal elastic lamina surrounded by concentric lamellar ring structures were seen throughout the intima and media components of the artery. These structures were surrounded by a mesh of elastic fibers which extended into the adventitia. All of these structures remained intact following the elastin digestion procedure. Furthermore, the components presented more intensely as more antigen sites on the elastic fibers were presumably exposed to bind the antibody. This indicates that the digestion procedure was successful in isolating an intact elastin matrix. Attempts to stain for collagen remnants in the isolated matrix were unsuccessful.

The mechanical properties of the isolated elastin scaffolds as assessed through uniaxial tensile testing are summarized in Table 4.2. Although only preliminary testing was performed (One Batch, n=2), these data demonstrate that a considerable loss of strength occured during the digestion process. Furthermore, variations in the isolation process had little impact upon the resulting mechanical properties of the scaffolds.

It was observed that the uniaxial tensile parameters of the isolated elastin scaffolds are approximately an order of magnitude larger than those of unreinforced, collagen-based constructs.

TABLE 4.2

Uniaxial Tensile Mechanical Parameters of Isolated Elastin Scaffolds. Scaffolds were isolated from porcine carotid arteries. Ultimate tensile stresses and linear moduli are reported ± standard error. Data corresponds to n = 2.

| Isolation Process | Uniaxial Tensile Stress (kPa) | Linear Modulus (kPa) |
| --- | --- | --- |
| Undigested Native Artery | 1,980 ± 280 | 3,430 ± 58.8 |
| Full Digestion | 69.8 ± 20.6 | 106 ± 32.2 |
| No β-ME or CNBr | 55.2 ± 17.6 | 146 ± 5.5 |
| One Autoclave Cycle | 69.4 ± 9.2 | 114 ± 9.1 |

Gel Compaction Data

Figure 2:
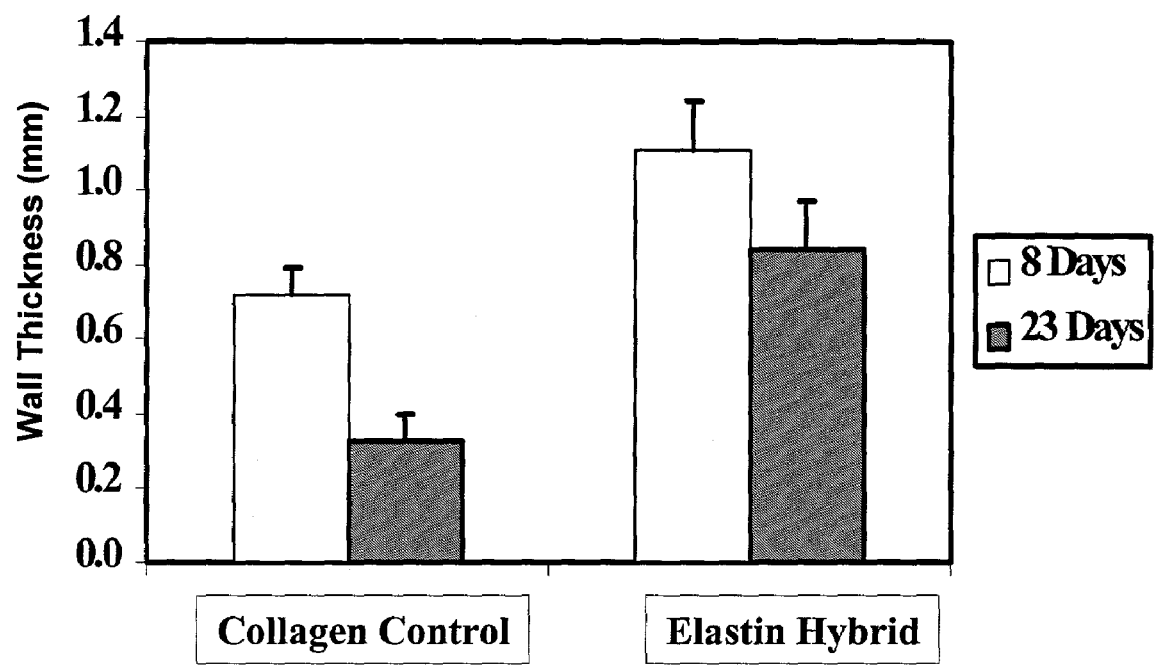
FIG. 2 is a chart showing wall thicknesses of HDF constructs.

Following the incorporation of a collagen gel cell composition about the elastin scaffold, the cells rapidly compacted their surrounding matrix. Illustrated in FIGS. 1 and 2, both the HDFs and RASMs exhibited similar compaction trends with and without the isolated elastin scaffold components. Differences between the elastin-hybrid constructs and the collagen-based controls mainly resulted from the elastin scaffold which was fairly resistant to cell-based reorganization and presented a physical barrier to compaction. While compaction rates were highest in the initial days following construct fabrication, collagen matrix remodeling and volume reduction continued to occur throughout the twenty-three days investigated.

HDFs were capable of high degrees of collagen gel compaction. After eight days of culture, the collagen-based gels contained only 6.2% of their original volumes. This behavior continued until only 3.3% of the original volume remained after twenty-three days of development ($p<0.07$ vs. Day 8). When scaffolds of isolated elastin were incorporated into the gels, compaction to 13.1% of the original construct volume was observed after eight days of culture ($p<0.0001$ vs. Collagen Control). After twenty-three days of culture, only 9.9% of the original elastin-hybrid construct volume remained ($p<0.16$ vs. Elastin Hybrid-Day 8; $p<0.0003$ vs. Collagen Control-Day 23).

Figure 3:
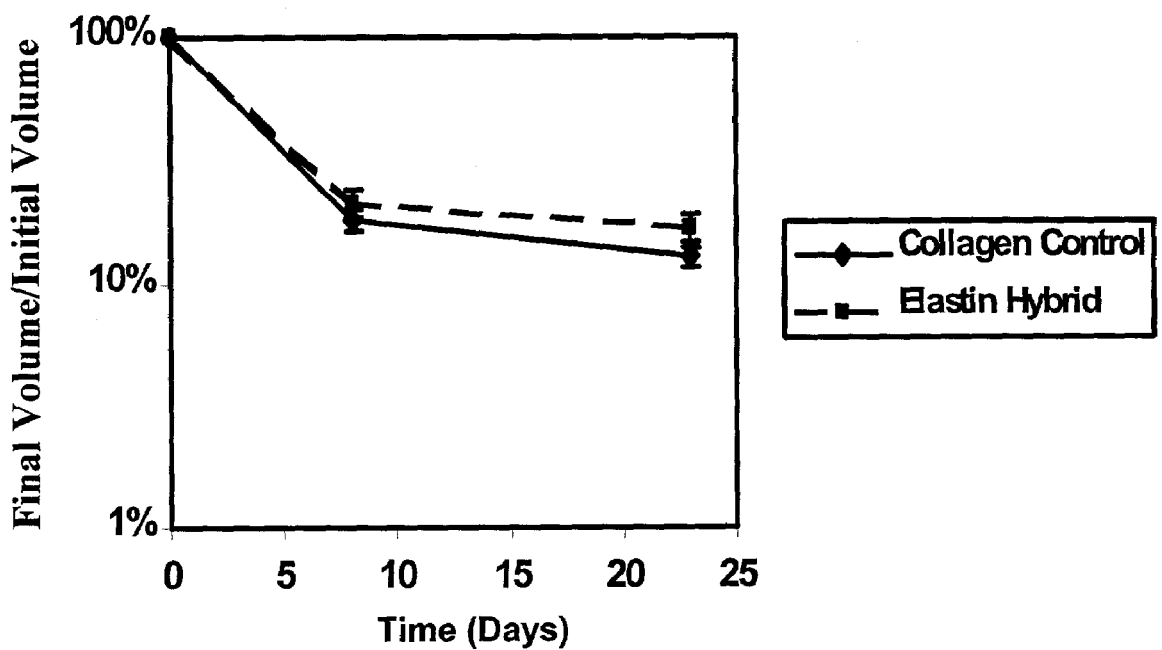
FIG. 3 is a graph showing compaction in RASM constructs.

Shown in FIG. 3, changes in the wall thicknesses of the HDF constructs mirrored the overall compaction trends. Following an eight day culturing period, the walls of elastin hybrid constructs seeded with HDFs were 1.5-fold thicker on average than in the collagen-based controls ($p<0.03$). By day twenty-three, this effect had increased to a 2.7-fold differential ($p<0.006$) as the collagen continued to compact while the dimensions of the elastin scaffold remained relatively unchanged.

Experiments using rat cells revealed slightly reduced RASM gel compaction capabilities compared to HDFs. After eight days of culture, collagen-based control constructs seeded with RASMs occupied 17.9% of their original volume ($p<0.001$ vs. HDF). Compaction in RASM constructs continued beyond the eight day observation point, and only 12.7% of the original construct volume remained after twenty-three days of culture ($p<0.27$ vs. Day 8; $p<0.001$ vs. HDF-Day 23). At day eight, hybrid scaffold constructs occupied 21.1% of their original volume ($p<0.72$ vs. HDF Hybrid, $p<0.59$ vs. RASM Control). At day twenty-three, hybrid scaffold constructs occupied 16.8% of their original volume ($p<0.35$ vs. RASM Hybrid-Day 8, $p<0.46$ vs. RASM Control-Day 23, $p<0.34$ vs. HDF Hybrid-Day 23)

Figure 4:
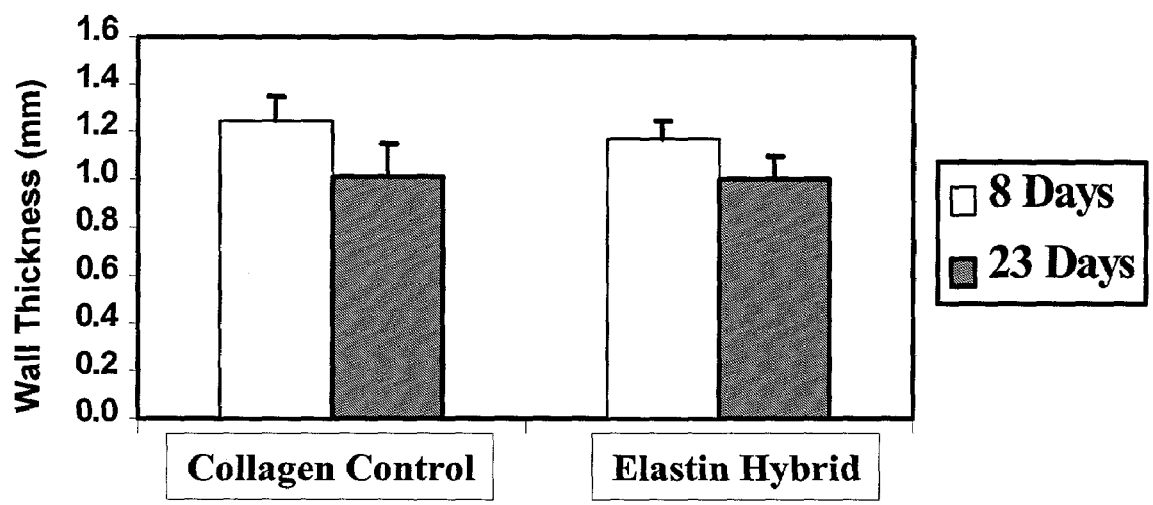
FIG. 4 is a chart showing wall thicknesses of RASM constructs.

Shown in FIG. 4, the changes in the thickness of the RASM construct walls followed the time-dependent compaction trends during the twenty-three days of culturing. From day eight to day twenty-three, the elastin hybrid constructs exhibited a 14% reduction in wall thickness ($p<0.57$). Likewise, the collagen control constructs exhibited a 19% reduction in wall thickness over the same time span ($p<0.31$). The effects of the elastin scaffold on wall thickness seen in the HDF experiments were not observed in the RASM constructs. A 6% decrease ($p<0.93$) was actually observed at day eight while only 1% increase ($p<0.9999$) was observed in mean thickness values between elastin hybrid and collagen control constructs at day twenty-three. Some of the differences observed between cell types can be attributed to the fact that RASMs do not remodel and compact their surrounding matrix as vigorously as HDFs. With the decreased overall compaction in RASM constructs, it is likely that the defined volume of the refractory elastin scaffold did not impact the overall construct dimensions as much as it did in the HDF constructs.

Histological Staining

Histological examination of the elastin hybrid constructs was performed using H&E staining. The elastin matrix presented darker than the fibers of the reconstituted collagen gel. The ECM of native arteries was colored much darker than either the elastin hybrid or collagen control samples when stained for equal time durations. As seen previously in the exogenous elastin fragment studies, the elastin hybrid and collagen control samples exhibited dense layers of cells along the outer walls of the constructs. Overall, however, the cell density in native arteries was higher than in the TE grafts.

The majority of collagen and cells in the elastin hybrids was located along the outer edge of the constructs. A thin layer of cell-seeded collagen could be seen along the inner lumen where the gel had formed between the elastin scaffold and glass mandrel. Although a few cells could be visualized inside the elastin structure, the vast majority of cells remained in the collagen components of the constructs.

Uniaxial Tensile Testing

Uniaxial tensile testing was conducted on ~5 mm ring samples to assess overall strengths of the constructs with and without an elastin scaffold supplement. The general profiles of the elastin hybrid and collagen control stress-strain relationships had some notable similarities and differences. Both types of constructs exhibited characteristic "toe-regions" at the onset of the stress-strain profiles as ECM components such as collagen and elastic fibers were recruited and oriented by the hooks of the mechanical testing apparatus.

The two types of constructs differed most notably in terms of the peak stresses attained prior to failure, but besides these differences in stress magnitudes, elastin scaffold constructs tended to exhibit more truly linear "linear modulus" regions which extended up to the point of peak stress. Following this point, some of the elastin scaffold constructs failed abruptly while others tore partially and exhibited secondary and tertiary linear stress-strain "saw tooth" regions before ultimately failing. The linear stress-strain region of the control constructs had a more gradual termination as the graded onset of plastic deformation resulted in steady decreases of the stress-strain modulus. This plastic deformation frequently spanned a 50% region of strain. As collagen fibril bundles tore and slid past one another, the stresses continued to increase initially but eventually decayed and dropped down to nominal levels.

Ultimate Stresses and Linear Moduli

Figure 5:
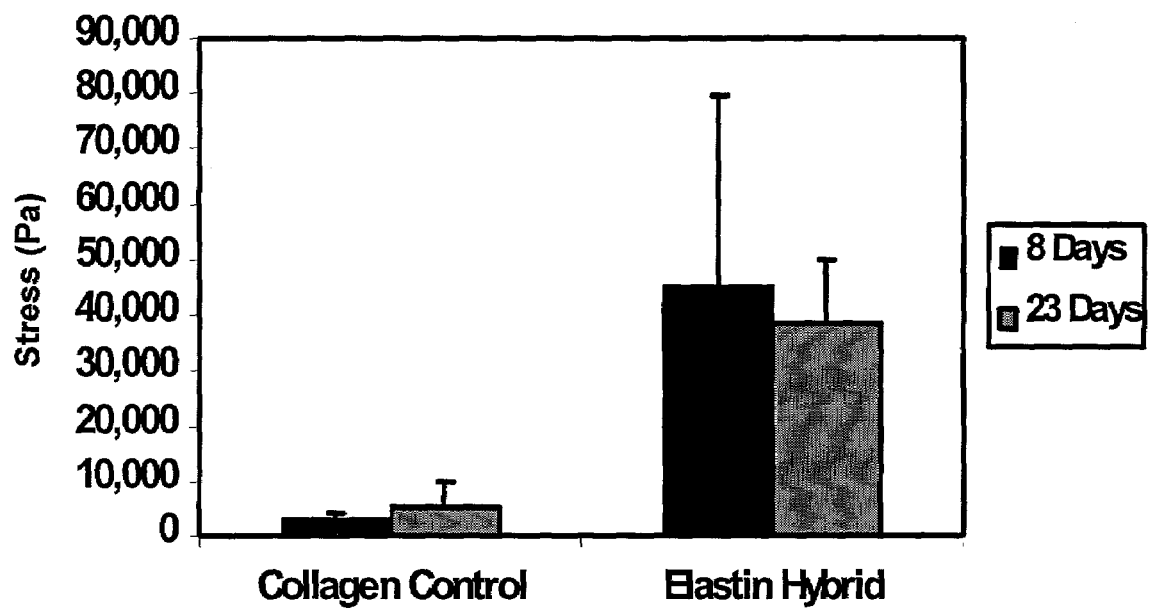
FIG. 5 is a chart showing ultimate tensile stresses of HDF constructs.
Figure 6:
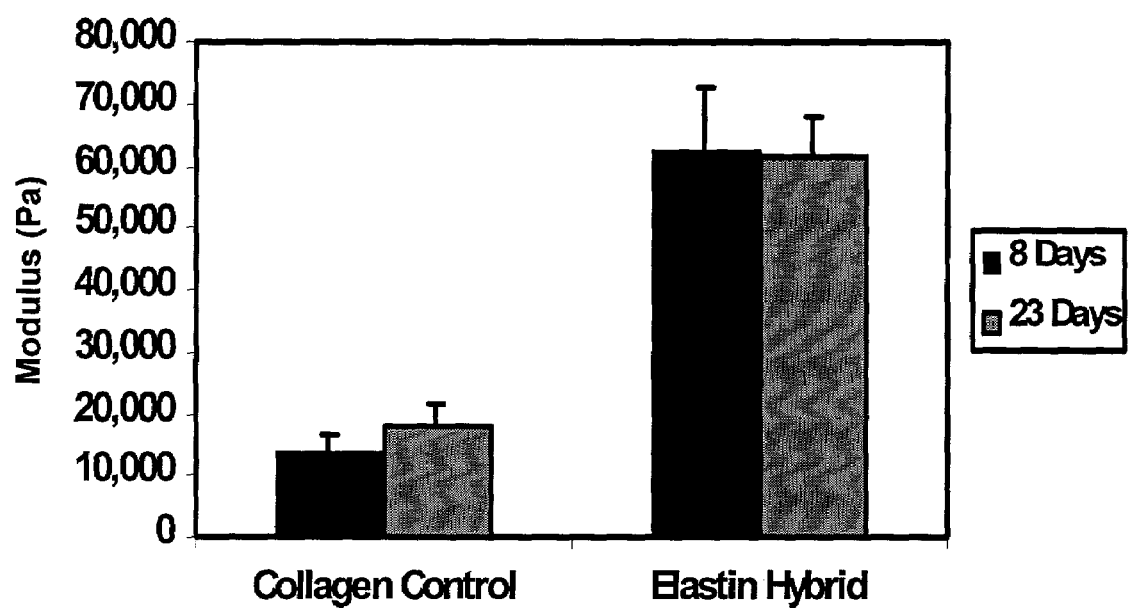
FIG. 6 is a chart linear moduli of HDF constructs.

The ultimate stress and linear modulus mechanical parameters of constructs seeded with HDFs are summarized in FIGS. 5 and 6. Elastin hybrid constructs cultured statically for eight days exhibited 14.1-fold higher mean ultimate stresses ($p<0.0001$) than unreinforced control constructs. After twenty-three days of culture, the UTS increase had dropped to 7.2-fold ($p<0.0001$). This was due primarily to the larger observed mean UTS exhibited by the collagen control constructs which rose 65% from 3.2 kPa at day eight to 5.3 kPa at day twenty-three ($p<0.45$). Elastin hybrid constructs, on the other hand, exhibited no change in UTS ($p<0.9995$) between the two time points investigated.

The linear moduli of the HDF constructs was also higher in the presence of elastin scaffolds. At day eight, the average linear modulus for the elastin hybrids was 4.6-fold higher than for the collagen controls ($p<0.0001$). At day twenty-three, the modulus was 3.4-fold higher ($p<0.0002$). Again, the observed decrease in influence was due primarily to modulus changes in the collagen control samples which rose 31% from 13.7 kPa to 18.0 kPa ($p<0.75$) while the same parameter in the elastin hybrid samples remained constant ($p<0.9999$) during the additional 15 days of culturing.

Figure 7:
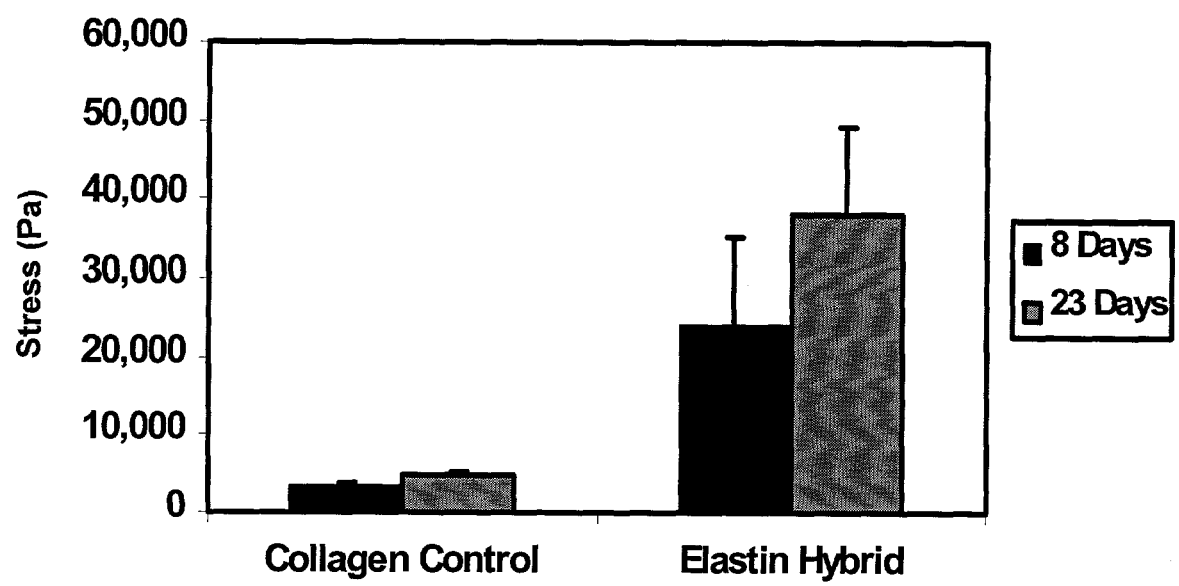
FIG. 7 is a chart showing ultimate tensile stresses of RASM constructs.
Figure 8:
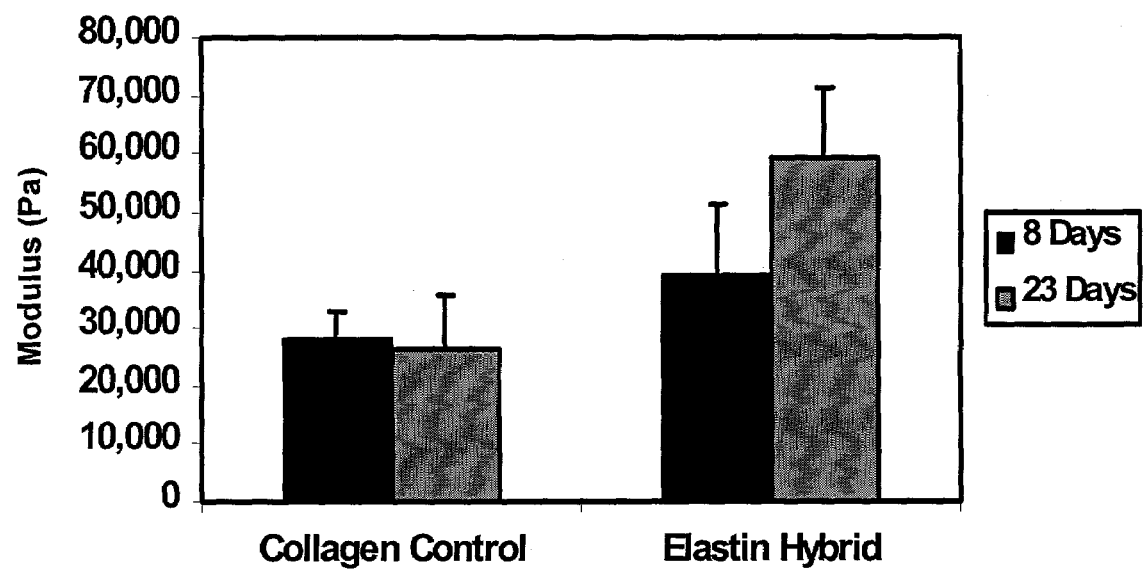
FIG. 8 is a chart showing linear moduli of RASM constructs.

The ultimate stress and linear modulus mechanical parameters of constructs seeded with RASMs are summarized in FIGS. 7 and 8. Elastin hybrid samples cultured statically for eight days exhibited a 7.2-fold larger mean UTS compared to collagen controls ($p<0.002$). Unlike HDF-seeded constructs, similar effects were observed after twenty-three days of culture as elastin hybrid UTS values were 8.0-fold higher than their collagen control counterparts ($p<0.0007$). As with the HDFs, observed mean ultimate stress values of RASM control samples rose 41% between days eight and twenty-three ($p<0.71$). Unlike the HDF samples, however, RASM elastin hybrid constructs exhibited a similar 57% larger UTS between at day twenty-three than at day eight ($p<0.32$) and consequently maintained the observed difference between hybrids and controls In general, the observed mean wall stiffnesses of the RASM constructs tended to be higher in the presence of the elastin scaffolds but did not result in statistically significant changes. At day eight, the linear modulus of the elastin hybrid constructs was, on average, 1.4-fold higher than in the collagen control constructs ($p<0.82$). At day twenty-three, the change had increased to a 2.2-fold difference for the two sample conditions ($p<0.093$). Control constructs seeded with RASMs exhibited no change in stiffness with culturing and possessed linear moduli of 28.1 kPa and 26.4 kPa at days eight and twenty-three respectively ($p<0.992$). Elastin hybrid constructs, on the other hand, exhibited a 1.5-fold increase in stiffness during the culturing period as their mean linear moduli rose from 39.4 kPa to 59.3 kPa ($p<0.47$).

In addition to affecting ultimate stress and construct stiffness parameters, the incorporation of an elastin scaffold also manifested in a larger degree of variance between samples. Much of this increased scatter could be attributed to sample to sample variability that took place between the isolated elastin scaffolds. Since the scaffolds were obtained from porcine carotid arteries, differences in size, diet, and genetic background of the pigs could result in changes in size, organization, and composition of their carotid arteries. This, coupled with variability introduced during the scaffold isolation and construct fabrication procedures, was most likely the cause for the large standard deviations observed.

At first glance, it would appear that the UTS increase in the collagen control samples would signify that the overall mechanical strengths of the constructs were increasing. While this is likely to be the case, it is important to note that some of the observed increases in stress values were the result of reductions in cross-sectional area caused by changes in the thicknesses of the sample walls. Eventually it would be desirable for the rate of cellular matrix synthesis to balance with the rate of matrix compaction and reorganization such that increases in ultimate stresses occur independent of the construct dimensions.

Yield and Failure Energies

Figure 9:
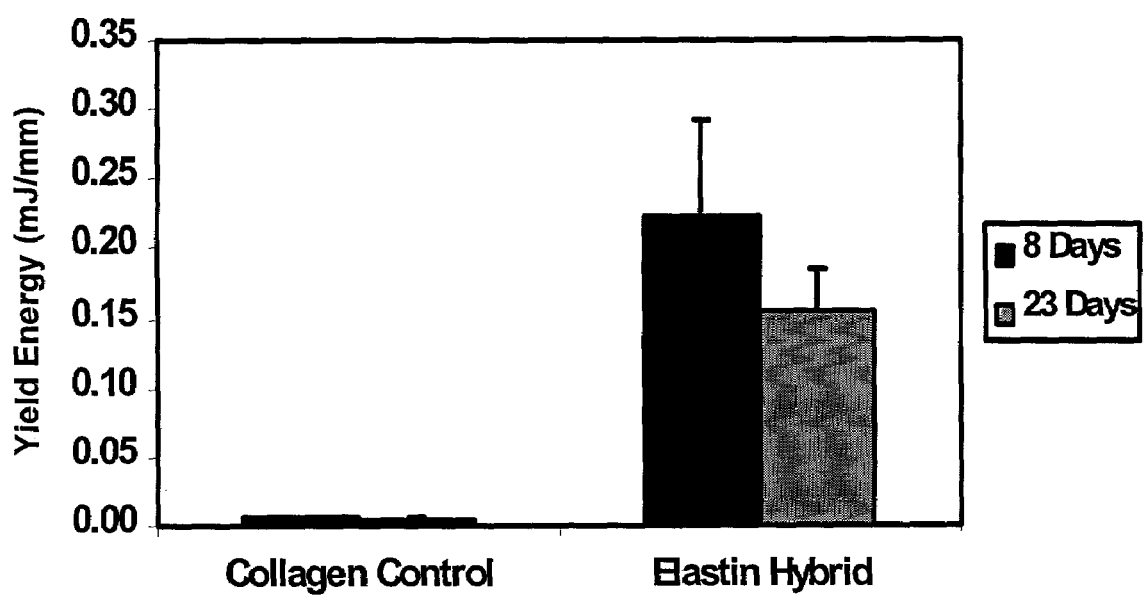
FIG. 9 is a chart showing yield energies of HDF constructs.
Figure 10:
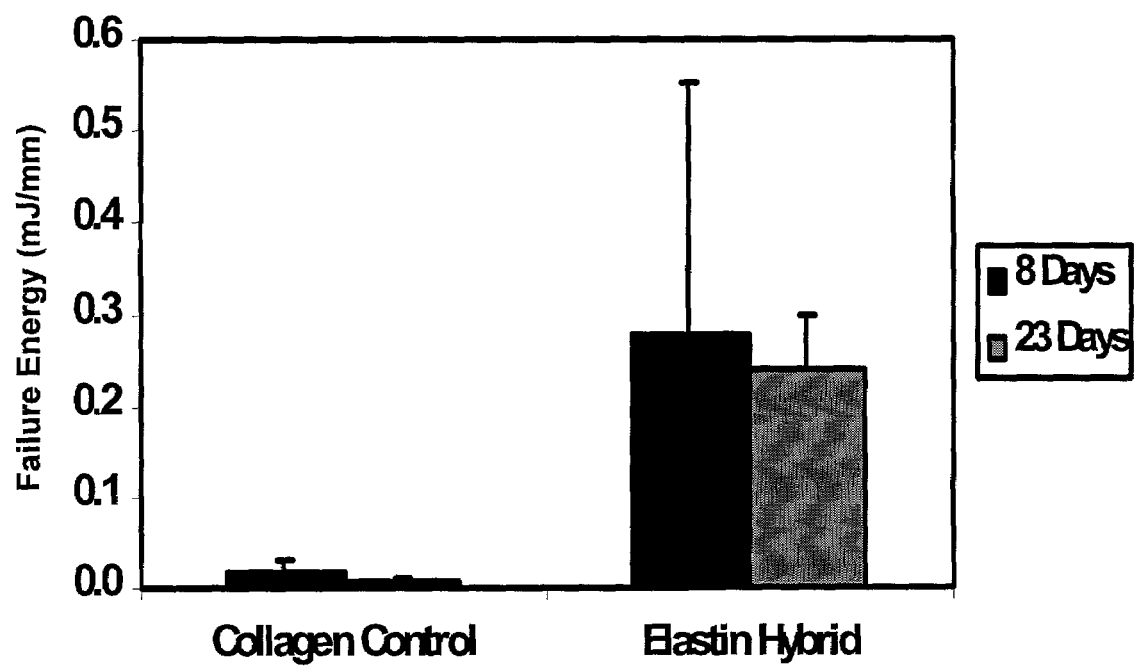
FIG. 10 is a chart showing failure energies of HDF constructs.

As described previously, the areas under the stress-strain curves can be utilized to give an idea of the degree of toughness in different construct samples. In the constructs populated with HDFs, summaries of the yield and failures energies can be seen in FIGS. 9 and 10. At day eight, constructs with an elastin scaffold possessed 41.0-fold ($p<0.0001$) and 17.1-fold ($p<0.0001$) larger yield and failure energies, respectively. These effects were mirrored at day twenty-three with 33.9-fold ($p<0.0001$) and 28.7-fold ($p<0.000\,1$) larger yield and failure energies with the incorporation of an elastin scaffold. In general, the energy parameters of the elastin hybrid and collagen control constructs did not change significantly with time in culture. The yield energies of the elastin hybrid constructs dropped 31% from 0.223 ml/mm to 0.154 mJ/mm ($p<0.93$) while in the collagen controls, the mean yield energies dropped from 0.0054 mJ/mm to 0.0045 mJ/mm ($p<0.59$). The observed mean failure energy of the elastin hybrid constructs dropped 13% from 0.276 mJ/mm to 0.241 mJ/mm ($p<0.99$) while the failure energies of the collagen controls dropped 48% from 0.0161 mJ/mm to 0.0084 mJ/mm ($p<0.12$).

Figure 11:
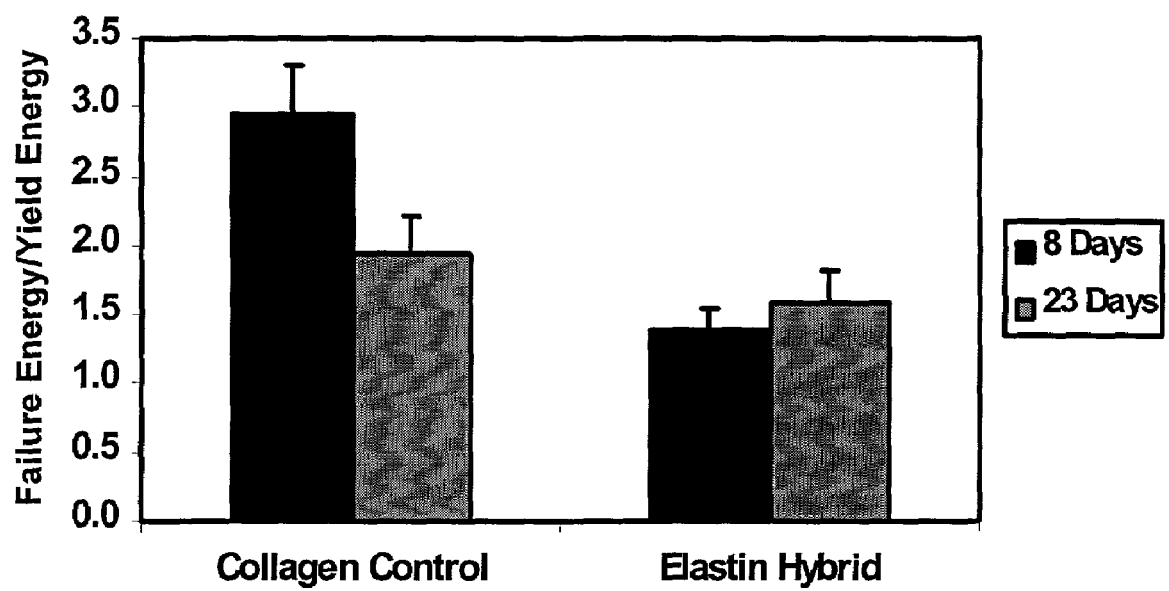
FIG. 11 is a chart showing failure/yield energy ratios of HDF constructs.

The ratios of yield energy to failure energy for constructs seeded with HDFs are shown in FIG. 11. These ratios were higher in control constructs at day eight (2.1-fold higher, $p<0.01$) but not day twenty-three (1.2-fold higher, $p<0.89$). This indicated that at day eight, the control constructs exhibited a substantial degree of plastic deformation prior to failure while the elastin hybrid constructs were prone to more sudden, "brittle" modes of failure. With culturing, the observed mean energy ratios of the collagen control samples dropped 35% ($p<0.08$) indicating that their failure mechanisms may have been changing to a more abrupt nature. The energy ratios of the elastin hybrid samples remained unchanged ($p<0.99$) indicating little to no change in the failure mechanisms.

Figure 12:
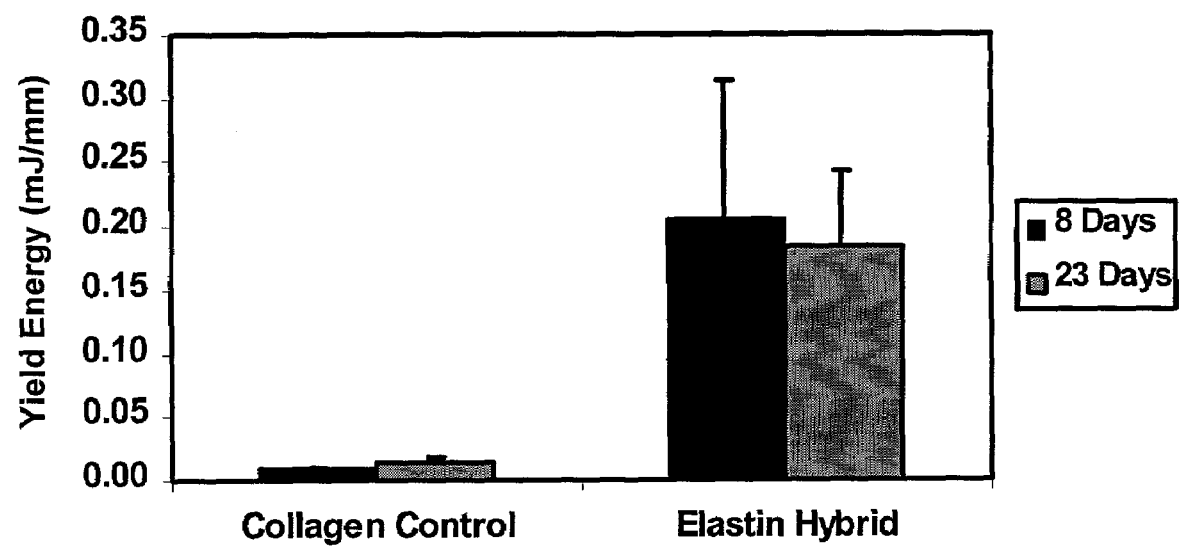
FIG. 12 is a chart showing yield energies of HDF constructs.
Figure 13:
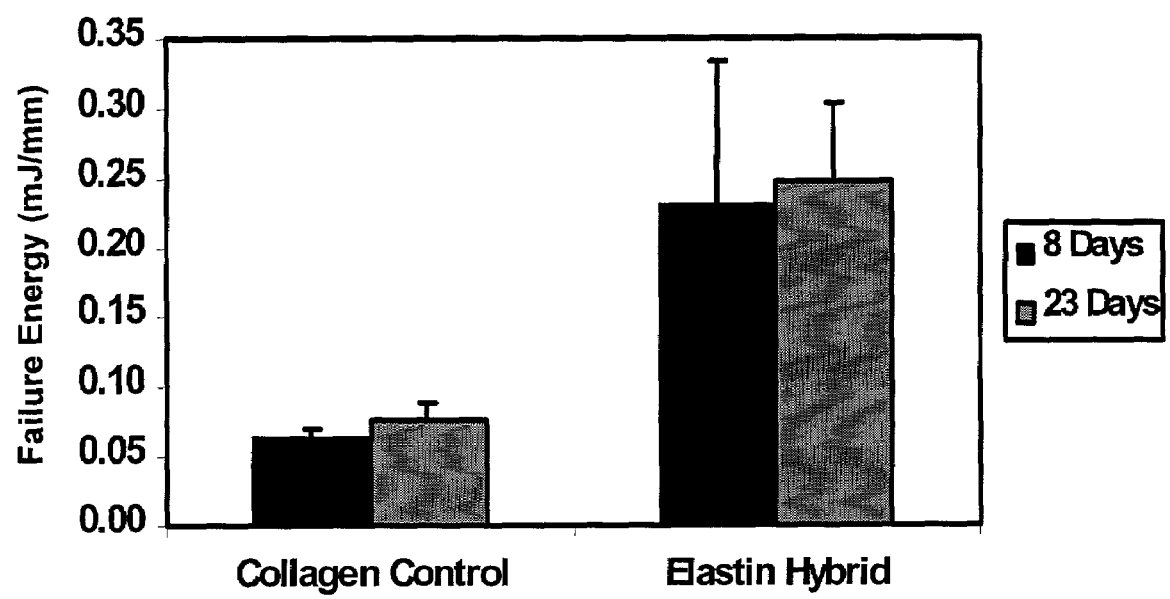
FIG. 13 is a chart showing failure energies of HDF constructs.

In the constructs populated with RASMs, summaries of the yield and failures energies can be seen in FIGS. 12 and 13. At day eight, constructs with an elastin scaffold demonstrated 22.2-fold ($p<0.002$) and 3.6-fold ($p<0.004$) larger yield and failure energies, respectively. These trends were mirrored at day twenty-three with 12.2-fold ($p<0.03$) and 3.2-fold ($p<0.03$) larger yield and failure energies with the incorporation of an elastin scaffold. The energy parameters of constructs seeded with RASMs did not necessarily decrease with culturing. While the mean yield energy of the elastin hybrid constructs dropped slightly from 0.205 mJ/mm to 0.183 mJ/mm ($p<0.26$), the yield energy values in the collagen controls rose 62% from 0.0092 mJ/mm to 0.0150 mJ/mm ($p<0.05$). The mean observed failure energy of the elastin hybrid constructs remained constant at 0.232 mJ/mm and 0.247 mJ/mm ($p<0.91$) while the failure energies of the collagen control samples rose 19% from 0.0635 mJ/mm to 0.0756 mJ/mm (p<0.40).

Figure 14:
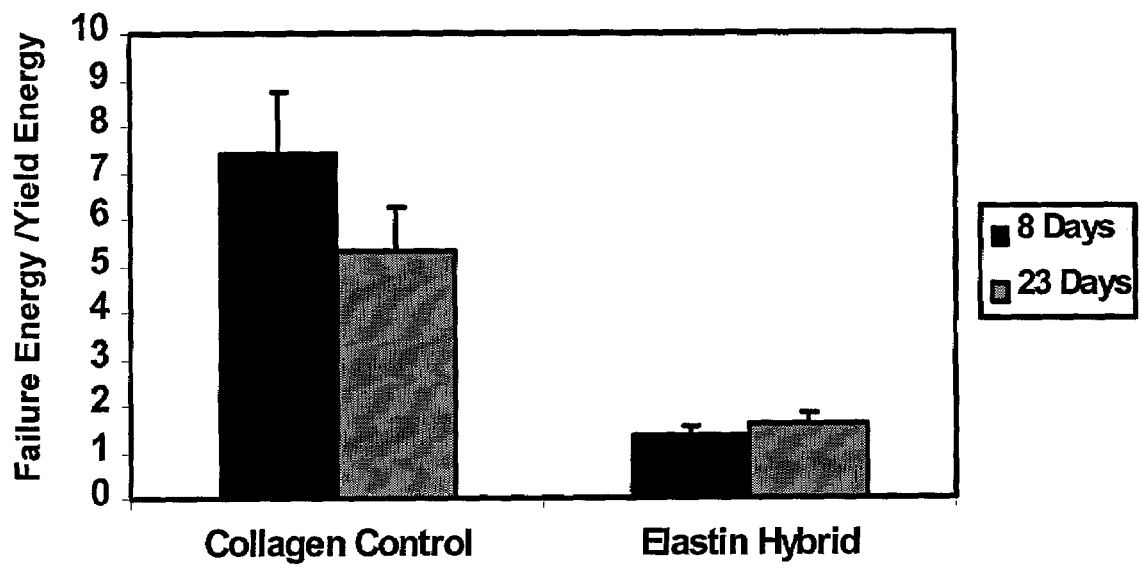
FIG. 14 is a chart showing failure/yield energy ratios of HDF constructs.

The ratios of yield energy to failure energy for constructs seeded with RASMs are shown in FIG. 14. These ratios were higher in control constructs both at day eight (5.4 fold higher, p<0.0001) and day twenty-three (3.3-fold higher, p<0.004) indicating that the control constructs exhibited a higher degree of plastic deformation prior to failure while the elastin hybrid constructs were more likely to fail through "brittle" failure modes. The energy ratios in both the collagen control samples (p<0.32) and elastin hybrid samples (p<0.996) remained essentially unchanged between the eight and twenty-three culturing time points.

Viscoelastic Testing

While conventional test-to-failure assays such as burst pressure and uniaxial tensile testing can provide important information in terms of the overall strength of a material, they fail to capture the time-dependent behaviors known as viscoelasticity. Although a majority of materials have historically been simplified down to their idealistic counterparts, no true material behaves completely like either a Hookean solid or a Newtonian fluid under all temperature, stress, and strain levels. Biological tissues, including ligaments, skin, and arteries, are good examples of materials that behave as both a viscous fluid and an elastic solid. Step stress relaxation and creep analysis were preformed in these experiments to characterize the viscoelastic properties of elastin hybrid and collagen control constructs seeded with either HDFs or RASMs. The extremely thin walls of the HDF control constructs after twenty-three days of culture complicated the viscoelastic characterization. Consequently, data was discarded in cases where these specimens were obviously damaged during sample preparation.

In the creep testing experiments, the applied mechanical load was set equal to one third of the estimated ultimate tensile stress of each construct. In the stepwise stress relaxation experiments, five discrete strain displacements were introduced to each sample at six minute intervals. Burger's four element mechanical model was fit to the data and used to elicit quantitative viscoelastic parameters.

Creep Analysis

Figure 15:
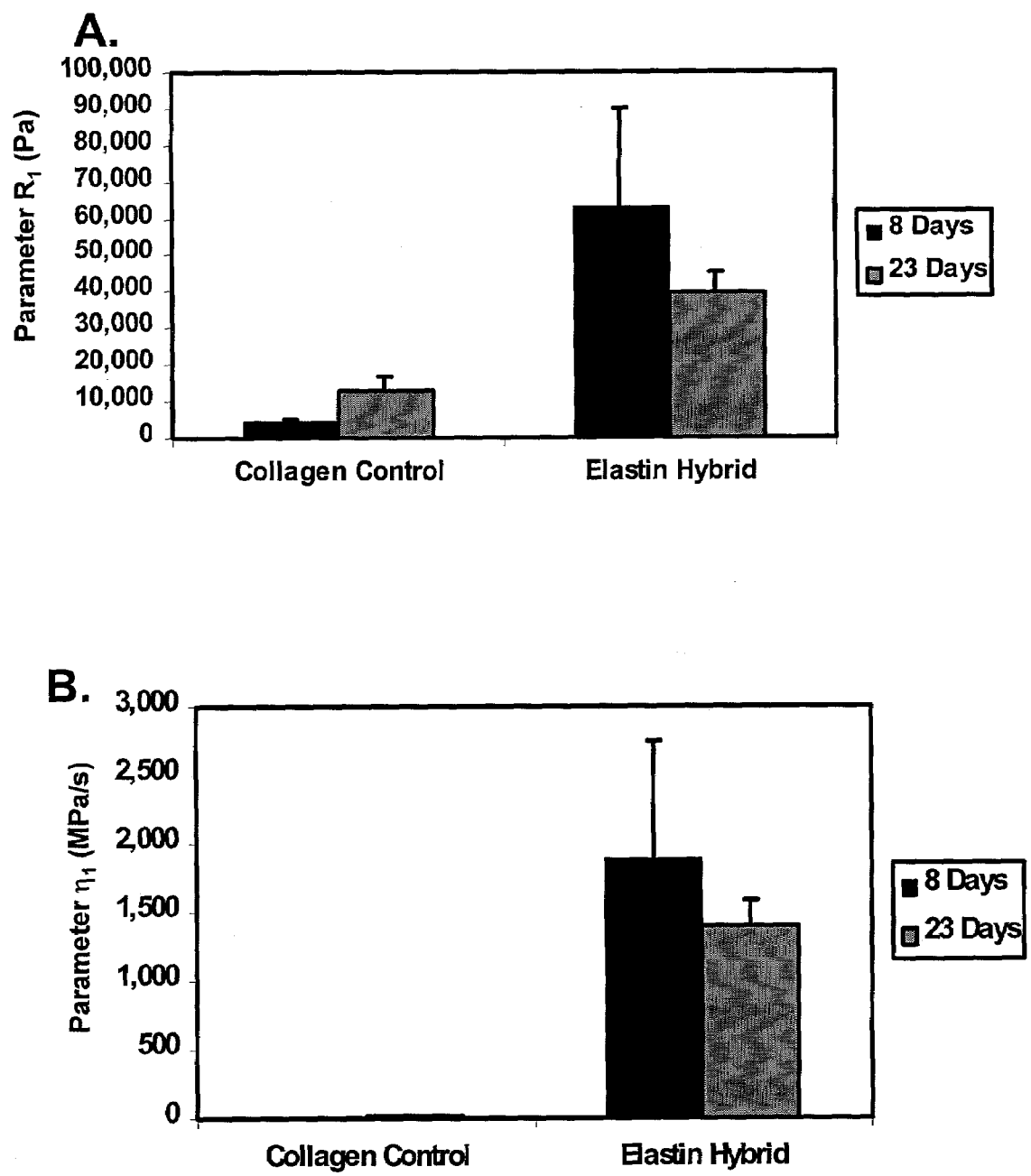
FIG. 15 is a graph showing characteristic creep profiles.

Typical creep behavior profiles for elastin hybrid and collagen control samples are illustrated in FIG. 15. Even under the larger mechanical loads, constructs containing an intact elastin scaffold experienced less overall strain than the collagen controls. Immediately following the introduction of the mechanical load, both sample types endured some degree of instantaneous strain which was followed by a transient region in which the rate of strain slowed to quasi-steady values. In the elastin hybrid samples, this transient decay occurred relatively quickly as the strain rates dropped to near zero values. The collagen control samples experienced longer transient regions which eventually declined to steady, non-negligible rates of strain. These steady strain rates were capable of deforming the samples until failure eventually occurred and occasionally resulted in the premature termination of the control creep experiments.

Figure 16:
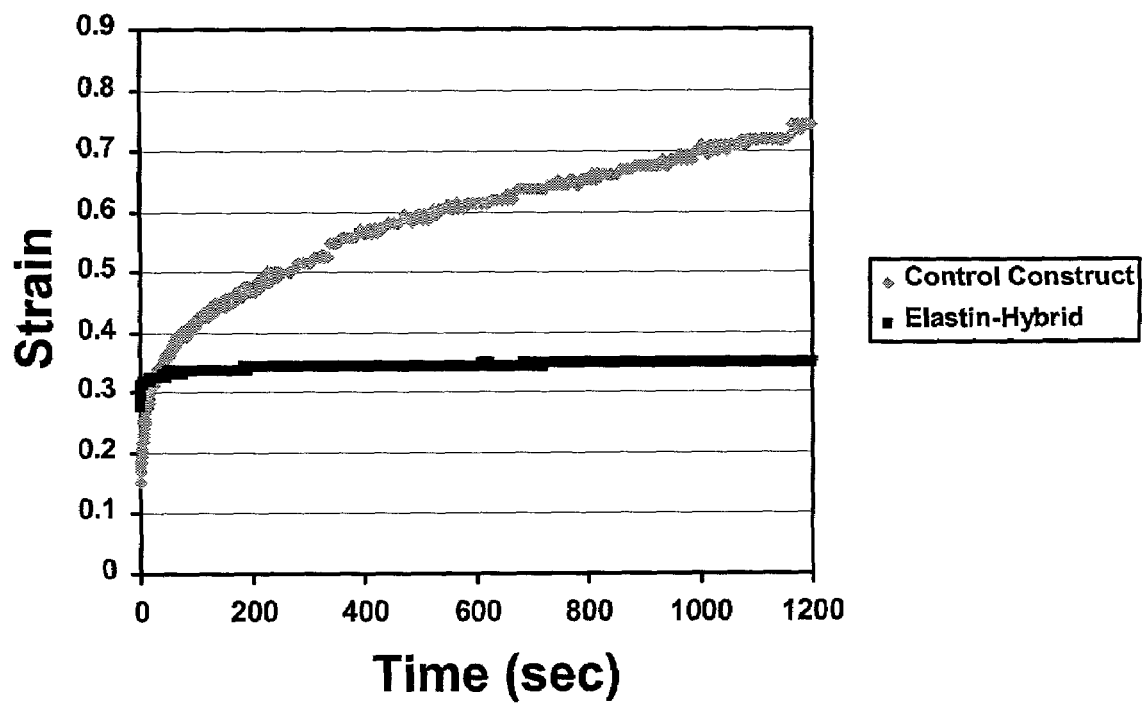
FIGS. 16A–D are charts showing Burger's Model Parameters of HDF constructs.

Burger's model provided a good fit of the creep behavior in both the elastin hybrid and collagen control samples seeded with HDFs with high average $R^2$ values of 0.871 and 0.984, respectively. The moduli of elasticity and coefficients of viscosity of the modeled HDF creep experiments are shown in FIG. 16. The elasticity parameter $R_1$ represents instantaneous deformations resulting from step load increases and was 15.0-fold (p<0.045) higher in elastin hybrid samples than collagen controls at day eight but showed no significant difference at day twenty-three (p<0.90). The elasticity parameter $R_2$ represents the degree of strain that occurs during the transient region and was 58.5-fold (p<0.0001) and 16.6-fold (p<0.015) higher in elastin hybrid samples after eight and twenty-three days of culturing, respectively. The elastin scaffold also affected the coefficient of viscosity $\eta_2$ which defines the length of the transient region. This parameter was 13.0-fold larger at day eight (p<0.0001) and 6.7-fold larger at day twenty-three (p<0.03) when elastin scaffolds were added to the constructs. The second coefficient of viscosity $\eta_1$ represents unrecoverable strain that occurs at long time points. Again, elastin hybrid samples exhibited higher $\eta_1$ coefficients with 504-fold (p<0.0001) and 83-fold (p<0.0001) larger values versus collagen control samples at days eight and twenty-three.

Figure 17:
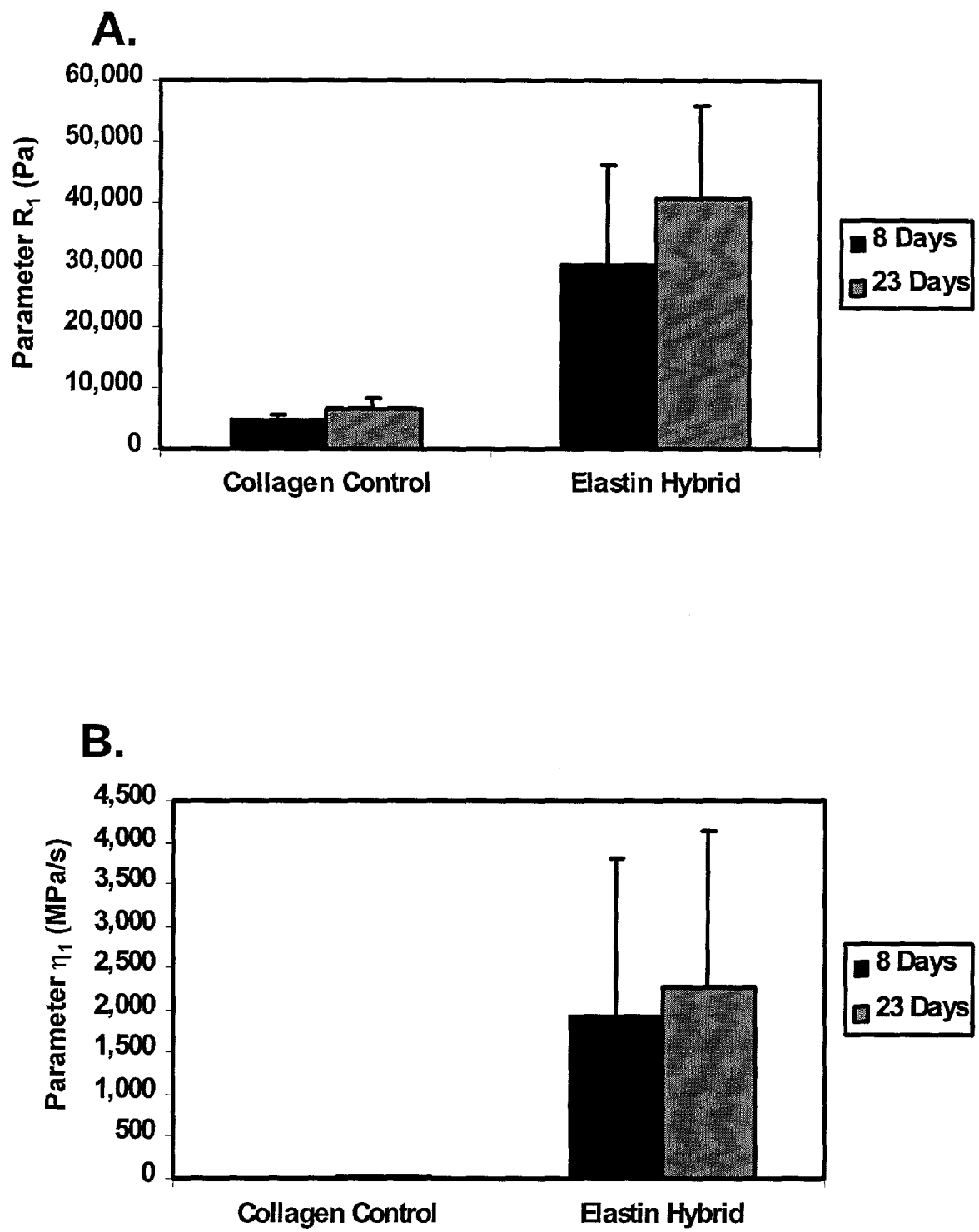
FIGS. 17A–D are charts showing Burger's Model Parameters of RASM constructs.

Burger's model also provided a good fit of the creep behavior in both the elastin hybrid and collagen control samples seeded with RASMs with average $R^2$ values of 0.879 and 0.976, respectively. The moduli of elasticity and coefficients of viscosity of the modeled RASM creep experiments are shown in FIG. 17. The elasticity parameter $R_1$ was statistically unchanged in elastin hybrid and collagen control samples after both eight (p<0.30) and twenty-three (p<0.15) days of culturing. The elasticity parameter $R_2$, on the other hand, was 16.2-fold (p<0.003) and 34.2-fold (p<0.0007) higher in elastin hybrid samples after eight and twenty-three days of culturing, respectively. Likewise, the coefficient of viscosity $\eta_2$ was generally higher (2.7-fold at Day 8, p<0.07 and 5.3-fold at Day 23, p<0.015) when elastin scaffolds were added to the constructs.

Finally, elastin hybrid samples exhibited higher $\eta_1$ coefficients with 239-fold (p<0.002) and 143-fold (p<0.002) higher values versus collagen control samples at days eight and twenty-three. This last parameter is especially important in that it describes long-term creep phenomena. As $\eta_1$ increases towards infinity, the constructs exhibit less and less sustained strain until the deformation becomes essentially negligible. At this point, the $\eta_1$ dashpot can be eliminated reducing Burger's viscoelastic fluid model to the Standard Viscoelastic Solid.

While the elastin scaffold treatment clearly had a significant impact on the viscoelastic creep parameters at almost every level, the length of culturing did not play as big a role in defining the creep behavior of the constructs. In the case of collagen control constructs seeded with HDFs, the p-values between the data collected at days eight and twenty-three were above 0.51 for $R_1$ and $R_2$ of Burger's model. The p-values of $\eta_1$ and $\eta_2$ were more notable—0.026 and 0.072, respectively. These differences are likely to be related to construct compaction which altered thickness of the construct walls between days eight and twenty-three. There were no statistical differences between the two time points in elastin hybrid constructs seeded with HDFs. With the exception of $\eta_2$ which had a value of 0.35, the remaining parameter p-values were all above 0.84. In control constructs containing RASMs, the p-values between the data sets collected at the eight and twenty-three time points exceeded 0.59 for all four Burger's model parameters. Similarly, the p-values between the data sets collected for elastin hybrid RASM samples at the two times were above 0.20 for $R_2$ and $\eta_2$ and above 0.79 for $R_1$ and $\eta_1$ of Burger's model.

Stress Relaxation Analysis

Figure 18:
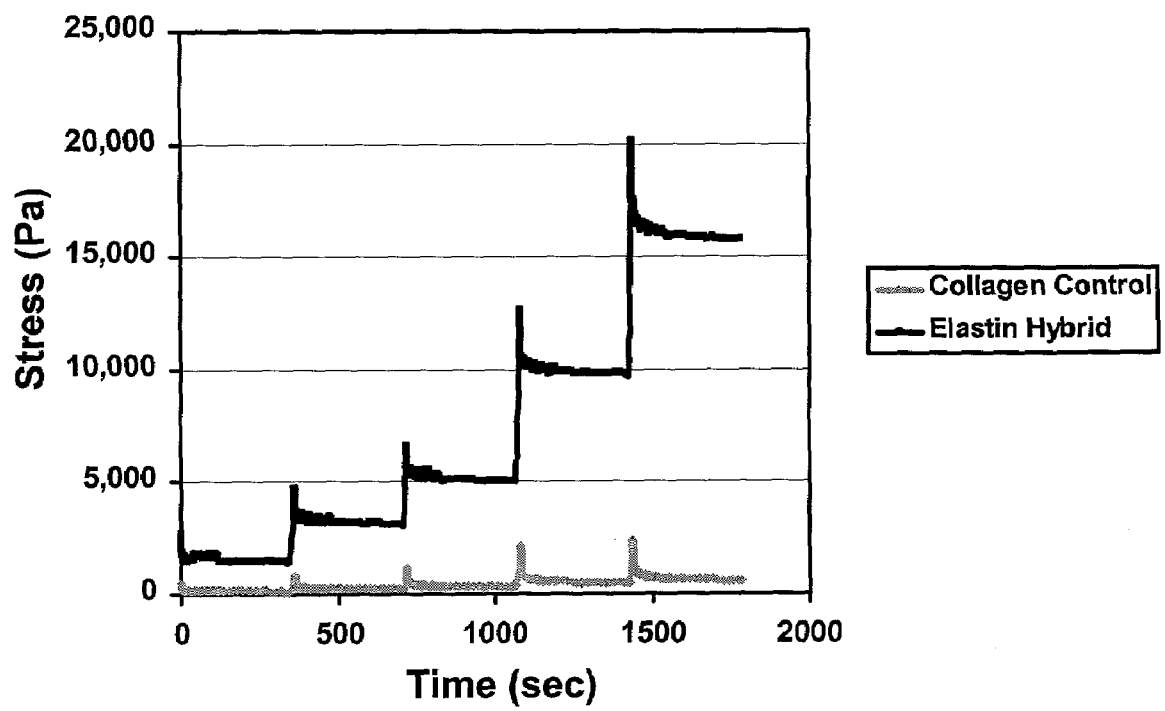
FIG. 18 is a graph showing relaxation profiles of constructs.

Stress relaxation characterization performs the inverse analysis of the creep tests and was used to complement the viscoelastic strudies. By examining the results of both the creep and stress relaxation tests, it was possible to identify any inconsistencies which may have resulted from anomalies introduced in the testing protocols or from selection of unsuitable mechanical models. The stress relaxation mechanical profiles were markedly different between collagen control and elastin hybrid samples as illustrated in FIG. 18. The relatively modest increases in stress which accompanied the step displacements of the control constructs rapidly decayed to approximately 25% of its original value. This remaining stress continued to decrease slowly over the subsequent six minutes at which point the test was repeated. The step displacements of the elastin hybrid constructs were accompanied by a more substantial jump in stress. Following the displacement, this stress dropped slightly to a steady-state, sustained level.

Initial stress relaxation moduli were calculated from stress-strain relationships of the ring samples immediately following each step displacement and were affected by both the viscous and elastic natures of the samples. Relaxed stress relaxation moduli were calculated from stress-strain data six minutes after each step displacement—just before the subsequent strain step. In these parameters, the transient viscous effects of the construct samples were assumed to have fully decayed leaving only the elastic components to bear the mechanical loads.

Figure 19:
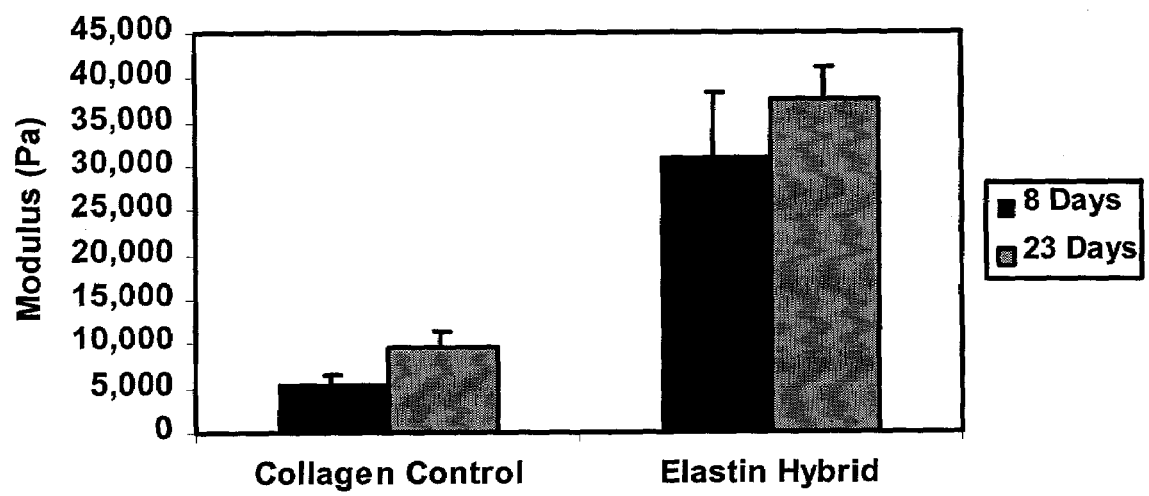
FIG. 19 is a chart showing initial moduli of HDF contructs.
Figure 20:
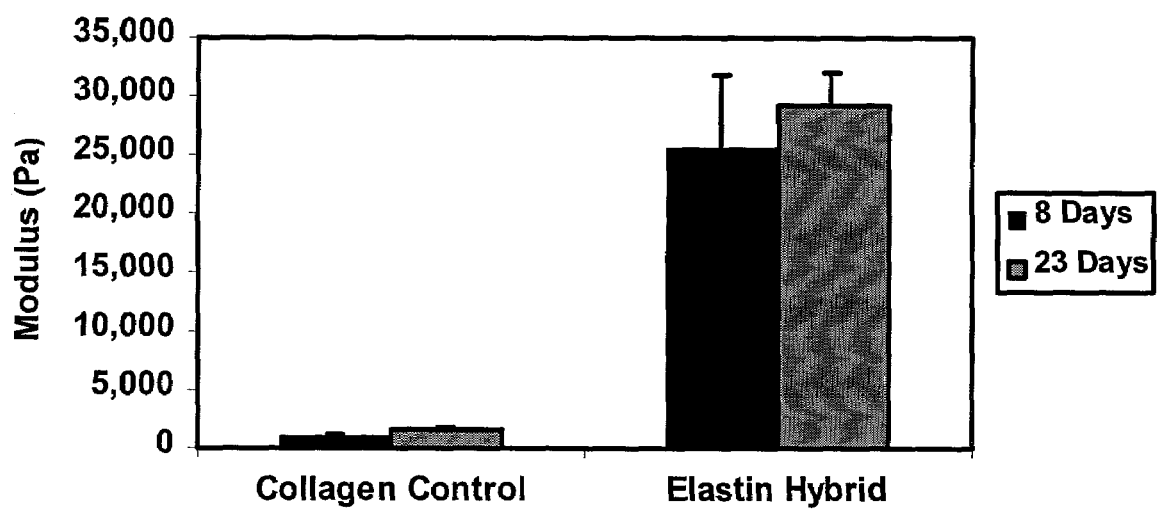
FIG. 20 is a chart showing relaxed moduli of HDF constructs.

In constructs seeded with HDFs, the initial moduli jumped 5.6-fold ($p<0.0001$) when collagen control samples were reinforced with elastin scaffold supports and cultured for eight days and 3.9-fold ($p<0.0002$) when cultured for twenty-three days as shown in FIG. 19. These findings are consistent with the uniaxial tensile test data presented previously which found higher moduli in elastin hybrid constructs than in collagen control constructs. The differences between the relaxed parameters, shown in FIG. 20, were even larger as inclusion of an elastin scaffold elicited 26.0-fold $p<0.0001$) and 17.6-fold ($p<0.0001$) increases in the relaxed moduli at days eight and twenty-three respectively.

Figure 21:
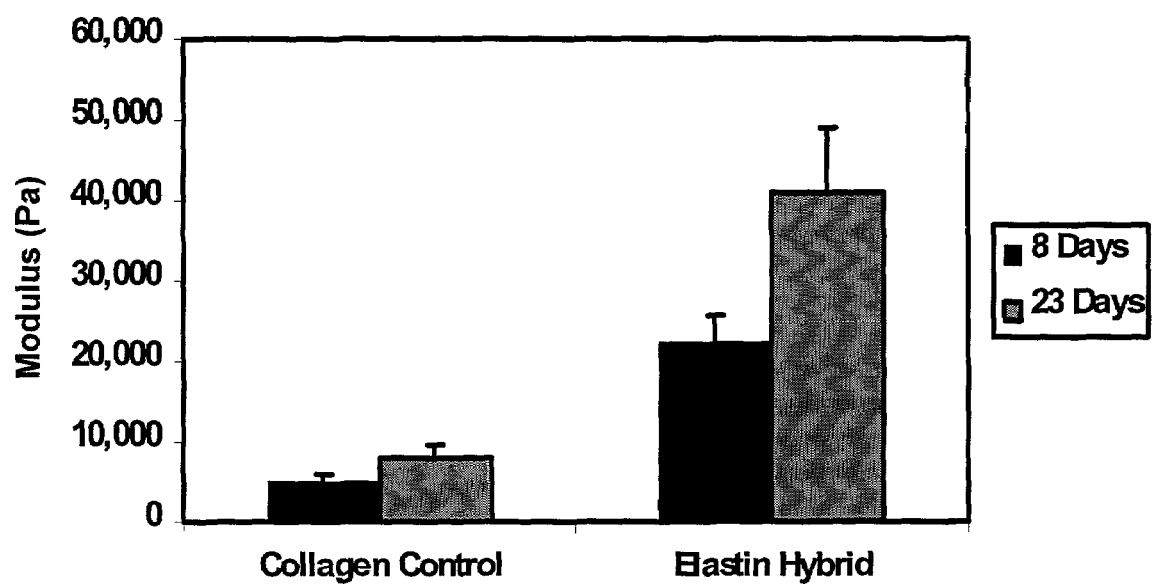
FIG. 21 is a chart showing initial moduli of RASM contructs.
Figure 22:
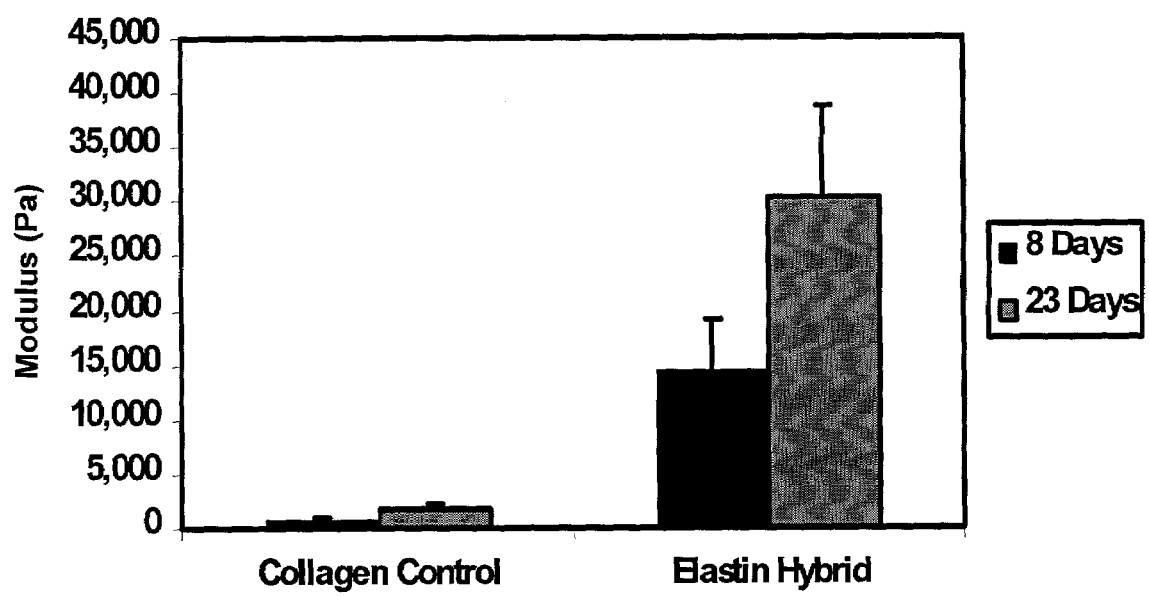
FIG. 22 is a chart showing relaxed moduli of RASM constructs.

Again, constructs seeded with RASMs had similar stress relaxation behaviors as those described for the HDFs. See FIGS. 21 and 22. When intact elastin scaffolds were incorporated into the constructs, the initial moduli jumped 4.5-fold ($p<0.0005$) and 5.1-fold ($p<0.006$) at days eight and twenty-three, respectively. The relaxed modulus increased even further as elastin hybrid samples containing RASMs were 16.7-fold ($p<0.013$) and 17.8-fold ($p<0.015$) stiffer than control samples after eight and twenty-three days of static culture, respectively.

Figure 23:
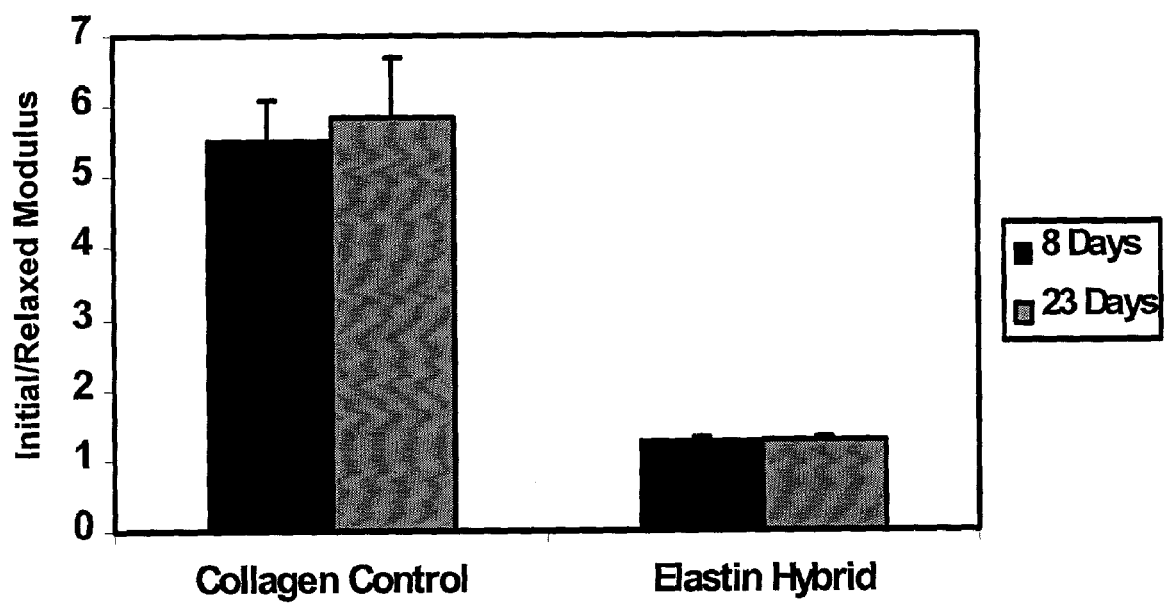
FIG. 23 is a chart showing initial/relaxed ratios of HDF constructs.
Figure 24:
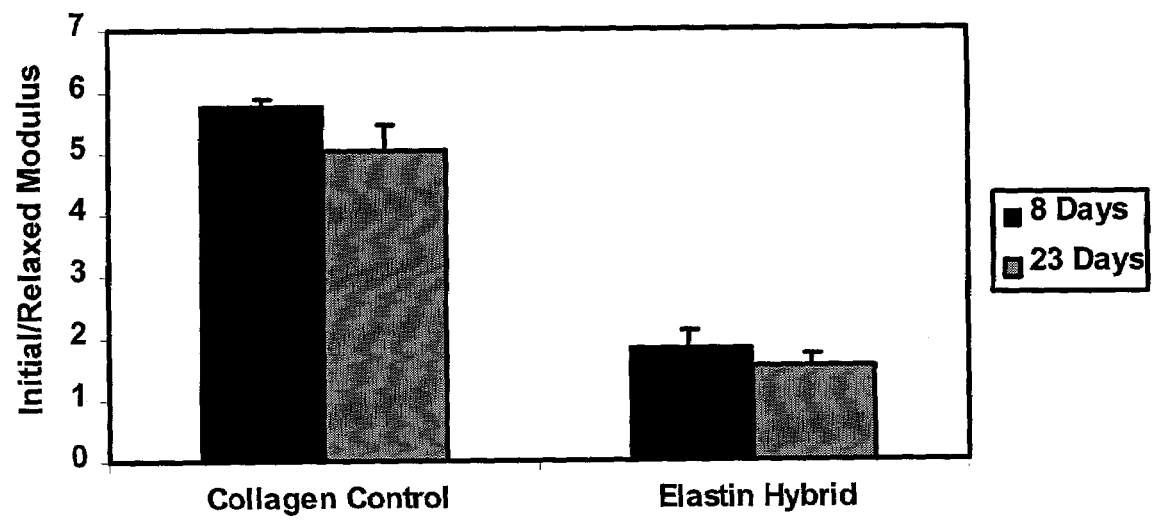
FIG. 24 is a chart showing initial/relaxed ratios of RASM constructs.

Ratios of the two stress relaxation moduli were used to help identify the nature of the mechanical properties that each construct possessed. As seen in FIGS. 23 and 24, the high ratios of the initial modulus to relaxed modulus in collagen control constructs indicated that the majority of their resistance to deformation stemmed from their highly viscous fluid-like natures. Conversely, the initial to relaxed modulus ratios of the elastin hybrid constructs were close to one indicating that their mechanical properties tended to result from their elastic natures. In every case examined, collagen control constructs had higher ratios of stress relaxation moduli than the elastin hybrid constructs (HDF: 4.4-fold higher, $p<0.0001$ at Day 8; 4.6-fold higher, $p<0.0001$ at Day 23; RASM: 3.1-fold higher, $p<0.0001$ at Day 8; 3.3-fold higher, $p<0.0001$ at Day 23).

As in the creep analysis, differences in the stress relaxation behaviors between the elastin hybrid and collagen control samples were much greater than differences that took place with the duration of culturing or between cell types. The p-values comparing the initial and relaxed moduli data sets of HDF-seeded elastin hybrids at eight and twenty-three days were 0.405 and 0.555, respectively. The equivalent values were 0.084 and 0.161 for RASM-seeded elastin hybrids. For collagen control constructs containing HDFs, the p-values were 0.044 and 0.005. Similarly, they were 0.109 and 0.084 for RASM collagen control samples. With the exception of HDF collagen control constructs, these differences did not achieve statistical significance.

Although the initial and relaxed moduli are excellent indicators of important stress relaxation behaviors of these vascular grafts, the time dependent stress-strain data can also be fit to mechanical models to obtain quantitative viscoelastic descriptions over the entire range of testing. The remainder of this section describes the stress relaxation behavior of the elastin hybrid and collagen control constructs utilizing the Burger's four element model. While the model simulated the stress relaxation data reasonably well, the fits were not as good as in the creep experiments. Although satisfactory solutions were identified which matched the requirements of the model, the fits generally did not extend to the stress levels immediately following the step displacement. Likewise, the models stress predictions dropped towards the zero level somewhat ahead of the experimental data. The overall fit, however was relatively good and it is likely that one would need to move to a model with additional or nonlinear parameters to obtain more accurate representations of the data.

Figure 25:
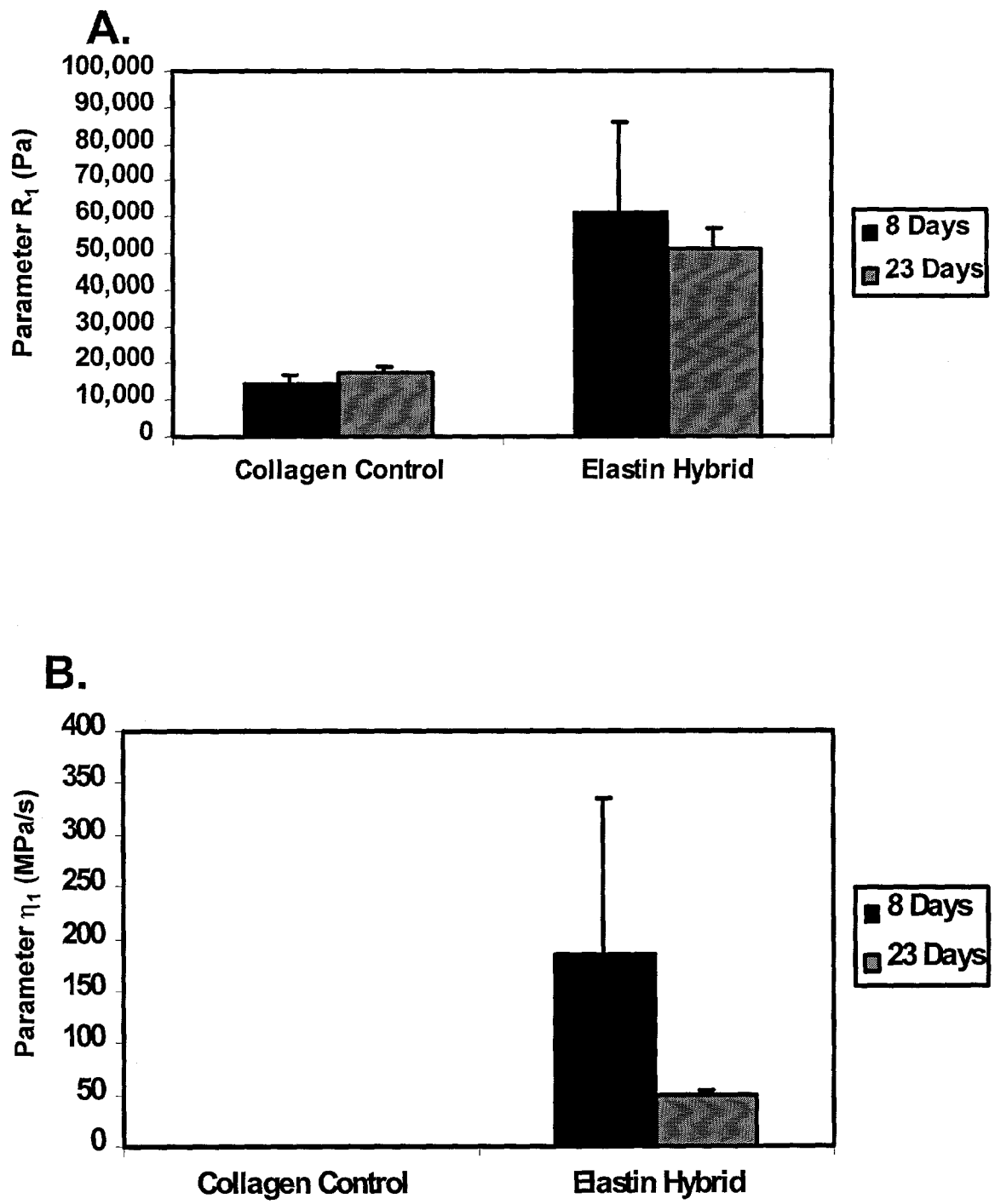
FIGS. 25A–D are charts showing Burger's Model parameters of HDF constructs.
Figure 26:
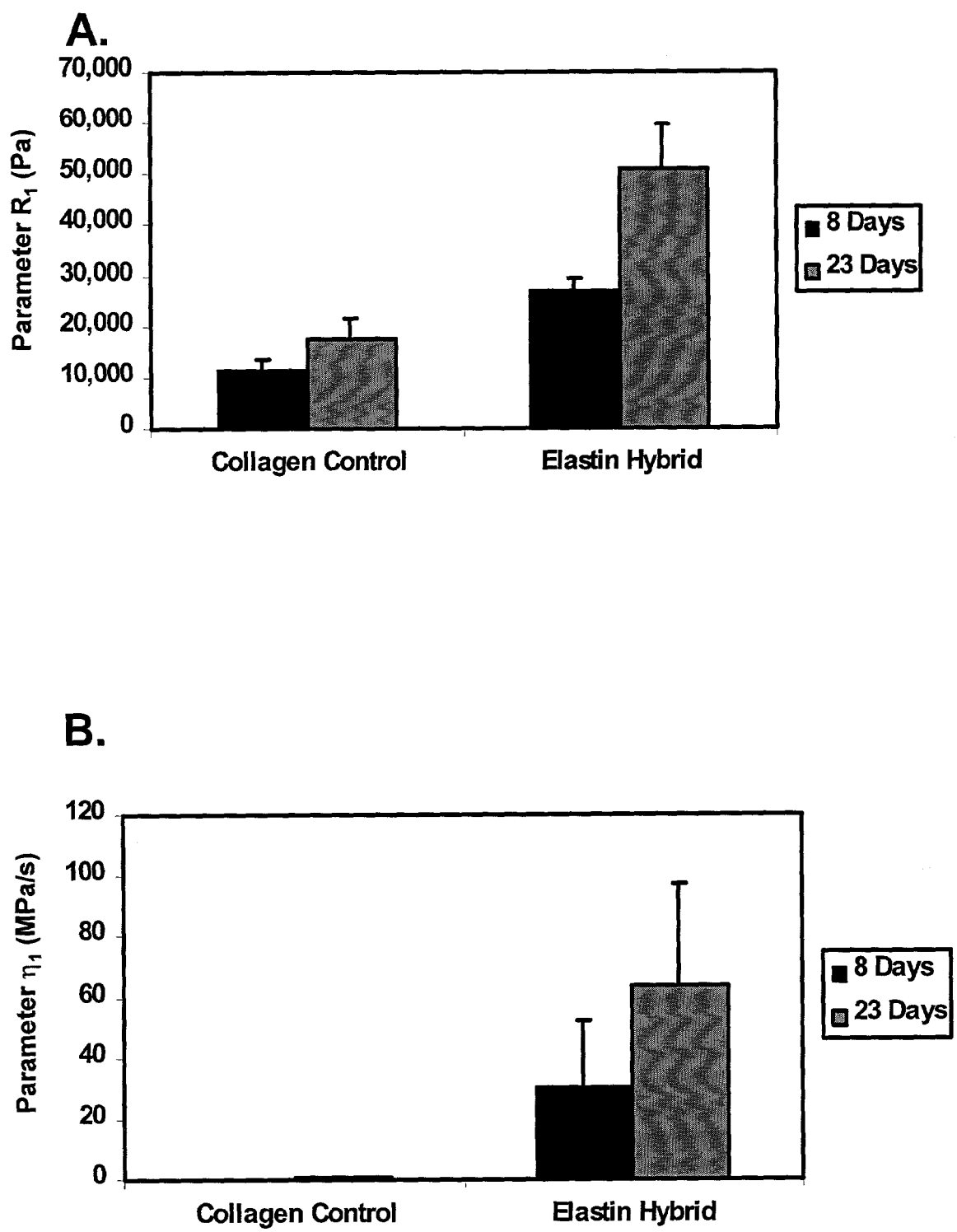
FIGS. 26A–D are charts showing Burger's Model parameters of RASM constructs.

The moduli of elasticity and coefficients of viscosity for constructs containing HDFs and RASMs as described using Burger's model are illustrated in FIGS. 25 and 26, respectively. The mean observed $R_1$ elasticity parameters which represents the stress resulting from the instantaneous strain steps were 4.2-fold ($p<0.025$) and 2.9-fold ($p<0.14$) higher in HDF elastin hybrid samples and 2.3-fold ($p<0.28$) and 2.9-fold ($p<0.005$) higher in RASM elastin hybrid samples than collagen controls after eight and twenty-three days of culturing, respectively. The elasticity parameter $R_2$ which represents the drop in stress levels in the time shortly following each strain jump was 64.0-fold ($p<0.0001$) and 13.7-fold ($p<0.0001$) higher in elastin hybrid samples containing HDFs and 16.2-fold ($p<0.0007$) and 17.0-fold ($p<0.0003$) higher samples containing RASMs after eight and twenty-three days of culturing, respectively. The elastin scaffold also affected the $\eta_2$ coefficient of viscosity which helps define the length of the region during which rapid relaxation of stress occurs. The $\eta_2$ of constructs seeded with HDFs increased 324-fold at day eight ($p<0.0001$) and 73-fold at day twenty-three ($p<0.0001$) when elastin scaffolds were added. The $\eta_2$ of constructs seeded with RASMs increased 37.8-fold at day eight ($p<0.0006$) and 24.8-fold at day twenty-three ($p<0.0003$) when elastin scaffolds were added. The $\eta_1$ coefficient of viscosity describes the rate the stress decays to zero once after the transient drops have ended. Again, elastin hybrid samples exhibited higher $\eta_1$ coefficients with 784-fold ($p<0.0001$) and 91-fold ($p<0.0001$) increases for HDFs and 110-fold ($p<0.0001$) and 95-fold ($p<0.0001$) increases for RASMs at days eight and twenty-three.

The duration of culturing did not have a large effect on the viscoelastic parameters of the constructs. There were no statistically significant differences between the eight and twenty-three day data sets in collagen control constructs seeded with HDFs. While the p-values for $\eta_1$ and $R_2$ were 0.38 and 0.68, respectively, the values for the other two parameters were greater than 0.90. Elastin hybrid constructs seeded with HDFs exhibited similar behaviors with p-values for all four mechanical parameters greater than 0.90. In control constructs containing RASMs, the p-values between the data sets collected at the eight and twenty-three time points exceeded 0.59 for all four Burger's model parameters. Similarly, the p-values between the data sets collected for elastin hybrid RASM samples at the two time points were above 0.4 for $\eta_1$, $R_2$, and $\eta_2$. In the case of $R_1$, the p-value parameter was 0.037 though it is not obvious why the parameter was so low.

Constructs that mimic native arterial structure and physiology will be more successful in maintaining long-term vascular function. Pericellular biochemical signals between the SMC and endothelial cells helps to regulate vasodilation and intima behavior. Additionally, significant ingrowth and integration of the elastin and collagen layers are necessary to ensure that the multi-component system will function as a single, intact composite structure. This integration will proceed as cells infiltrate the elastin scaffold and deposit new matrix between the lamellar layers.

Minimal cell ingrowth into the elastin layers, however, was observed in the isolated scaffold experiments. This could be due in part to low permeability of the elastic structures. Since elastin exists predominantly as concentric, lamellar sheets, cells must circumnavigate around the plies in order to infiltrate the structure. While this may present a seemingly sizable obstacle, nutrient diffusion gradients are another likely cause for the lack of observed ingrowth. Cell proliferation and migration has been linked to concentration gradients of oxygen, nutrients, and growth factors. Since the constructs were cultured upon an impermeable glass mandrel, the nutrient supply predominantly came from the outside. Consequently, it is not surprising that the highest cell densities were seen concentrated on the outermost layer of the constructs and cells on the inside of the constructs may have died of starvation. It may be possible to reduce or even reverse the outward migration by feeding the cells from both sides of the construct wall. Doping the lumenal media with excess serum or chemotactic factors may further augment these effects. An alternative solution could directly seed cells between the elastin layers using a syringe or similar device. Once placed in the desired locations, the cells should be able to synthesize matrix proteins and enhance the levels and rates of integration between the components of the hybrid constructs.

Calcification has been associated with elastin and elastic fibers and is often implicated in impaired performance of aortic and heart valve tissues. Some recent studies have indicated that microfibrillar proteins and not elastin itself may be responsible for calcium formation since the deposits typically form near the outside of the elastic fibers. Increases in calcium contents often coincide with high concentrations of acidic and polar amino acids. Glutamic acid and aspartic acid residues, which are frequently linked with calcification, constitute up to 10% of the fibrillin protein. Furthermore, fibrillin contains forty-three calcium-binding consensus sequences. If the microfibrillar proteins and not elastin are responsible for calcification of elastic fibers, then a digestion procedure which removes all non-elastin proteins from the matrix (like the one used in these isolated elastin scaffold studies) may reduce calcification in the tissue.

Species Heterogeniety

The species heterogeneity between the matrices and cells used in these isolated elastin scaffold experiments created an additional issue. While tissue engineered devices possess theoretical advantages over synthetic approaches which will typically elicit some degree of foreign body responses, allogenic and xenogenic materials introduce the potential for immunological responses. In general, extracellular matrix proteins are likely to elicit fewer immune rejection responses than cells and cellular components which contain major histocompatibility complex (MHC) molecules. Bovine and rat collagens have been used clinically in cosmetic applications with relatively few immunological complications. The site of the implantation, however, may play an important role in the resulting immune response. While xenogenic collagen may perform acceptably in the subcutaneous regions of the face, it is unclear whether the collagen can function in the hostile environment of the vasculature. If it does turn out that allogenic collagen is necessary for success in vascular grafts, human collagen can be isolated from human cells growing in culture. Isolated elastin scaffolds, on the other hand, may not be as suited for allogenic therapies. While some cadaveral arteries are likely to be available from tissue donors, shortages similar to those experienced with organ transplantation can limit large-scale production. Fortunately, while some differences between human and porcine elastins exist, the overall homology between the proteins is relatively high.

Cells present a larger challenge to implantation from an immunological perspective. Of the various cell types found in native arteries, fibroblasts are the most immune compatible and have been successfully used in allogenic skin graft products such as Dermagraft (Advanced Tissue Sciences, LaJolla, Calif.). Smooth muscle cells evoke somewhat moderate responses, but endothelial cells are extremely immunogenic. Use of autologous endothelial cells has been reported. Potential autogenic strategies include ECs from the microvasculature of adipose tissue or circulating ECs isolated from blood samples. Stem cells, both mesenchymal and embryonic, have also been proposed as alternative sources for immunocompatible endothelial cells. A final strategy attempts to modify privileged cells to mimic cells in the endothelium. The current theories are that allogenic SMC and fibroblasts should be acceptable while one of the strategies outlined for EC sourcing will hopefully be successful.

Example 5

De Novo Elastin Studies

One strategy used to explore the effects of elastin on vascular constructs utilized de novo elastin expression. Genetic manipulation of cells with no or low native expression levels were additional methods of stimulating elastin production. The following Examples describe the methods used to genetically engineer recombinant elastin expression and some of the experiments conducted using these and native expressing cells in two dimensional monolayers and three dimensional constructs.

In this method, cells are selected based upon their ability to express high levels of a target protein or based upon their capacity for genetic modification and recombinant overexpression. This method provides pericellular deposition of a matrix which could then be assembled on a cellular level.

Experiments involving de novo elastin production were studied to ascertain some of the possibilities and limitations of this approach. Plasmid expression vectors were constructed and transfected into NIH/3T3 murine fibroblasts and HDFs for recombinant elastin production. Rates of elastin synthesis were evaluated at the mRNA and tropoelastin levels on cells growing in monolayers and three-dimensional collagen constructs. Some additional studies involving cell proliferation and construct compaction were performed to identify potential secondary effects of genetic modification on cellular function. pIRES-Elastin Vector

Figure 27:
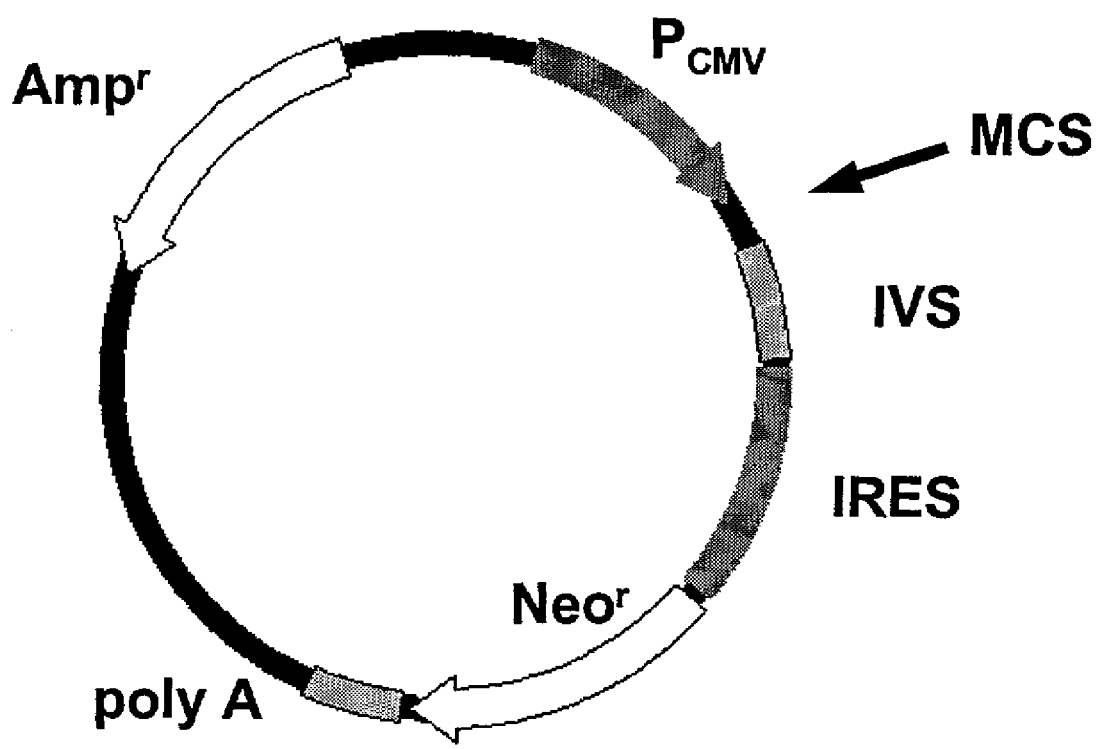
FIG. 27 is a graphic illustration of pIRES-1neo plasmid.

The pIRES-elastin expression vectors were constructed to induce overproduction of elastin in genetically modified cultured cells. A plasmid containing the cDNA for human tropoelastin was obtained from Dr. Joel Rosenbloom at the University of Pennsylvania Restriction enzyme mapping revealed the gene to be a ~2.2 kb molecule with EcoRI and NcoI sites at the 5' end and EcoRI and XbaI sites at the 3' end. The pIRES-1neo plasmid, shown in FIG. 27, (Clontech, Palo Alto, Calif.), has a single EcoRI site in its multicloning site (MCS) just downstream of a human cytomegalovirus promoter ($P_{CMV}$) and was selected as a bicistronic expression vector for elastin production.

Plasmid Construction

Figure 28:
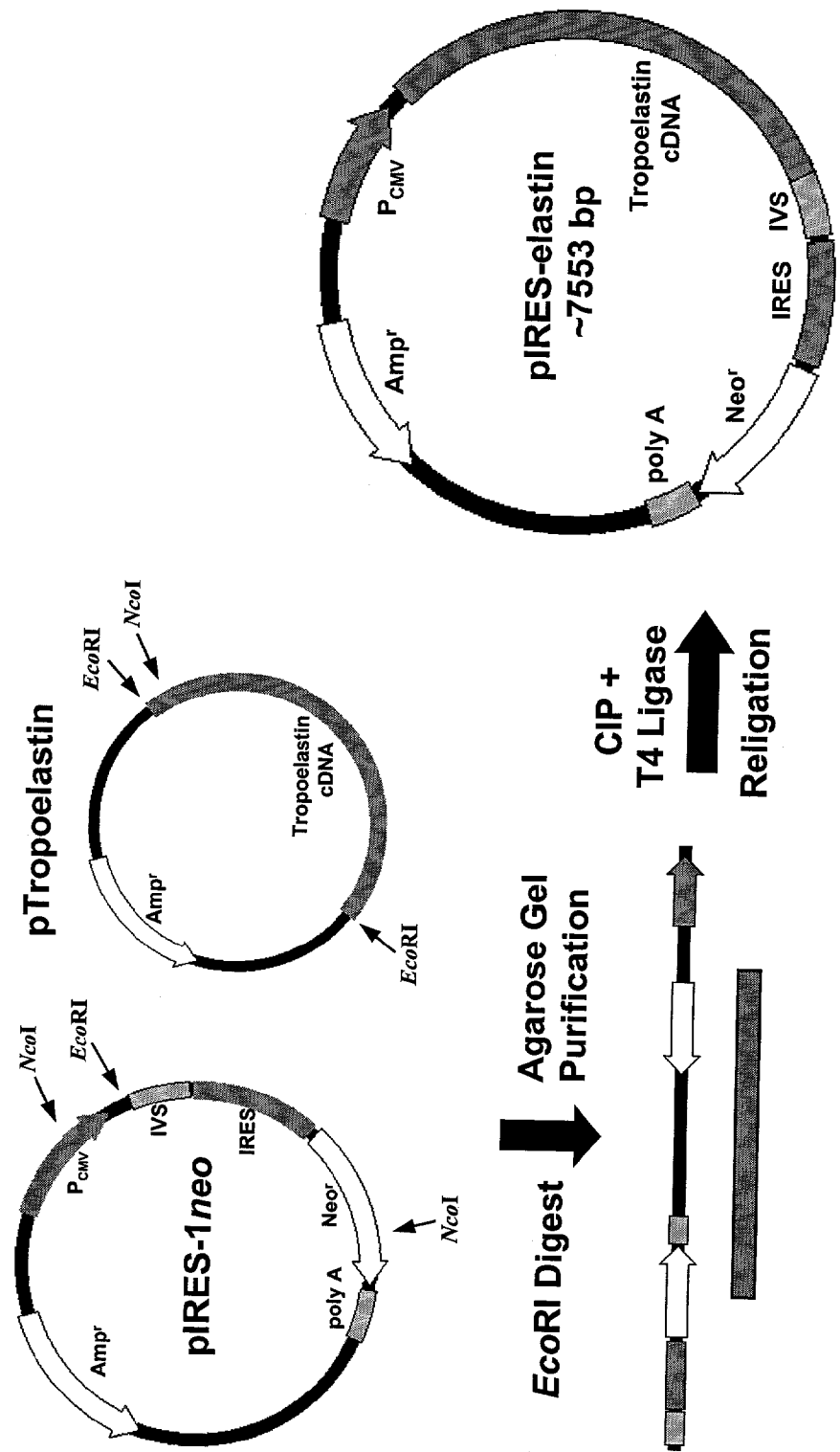
FIG. 28 is a schematic of the construction of pIRES-elastin plasmid.

The pIRES-elastin vector, shown in FIG. 28, was constructed using restriction enzyme digestion, agarose gel electrophoresis separation, and religation procedures. Human tropoelastin cDNA and pIRES-1neo expression plasmids were transformed into competent jm109 *E. coli* bacteria. Plasmid DNA was isolated from transformed bacteria using a Sephaglas™ FP purification kit (Amersham Pharmacia Biotech, Peapack, N.J.) and stored at −20° C. To construct the pIRES-elastin constitutive expression plasmid, the tropoelastin cDNA plasmids were digested with EcoRI restriction enzymes (New England Biolabs, Beverly, Mass.) at 37° C. for 60 min. Bromophenol loading buffer was added to the tropoelastin digest, and the cDNA was electrophoresed in a 1% low melting point SeaPlaque GTG agarose gel (Cambrex Corporation, East Rutherford, N.J.) containing 0.5 µg/ml ethidium bromide. The gels were run in a horizontal electrophoresis apparatus (Gibco BRL) using a low-EDTA Tris-acetate (TAE) buffer. As the samples were visualized under an UV transilluminator, the band corresponding to tropoelastin cDNA was cut out with a flame-sterilized blade. The agarose embedded DNA was melted at 65° C. for 15 min and digested in β-agarase (New England Biolabs) according to the manufacture's recommendations. The pIRES-1neo plasmid was also digested with EcoRI restriction enzymes followed by incubation in calf intestinal alkaline phosphatase (CIP) to remove the 5' phosphate groups thus preventing self-ligation. The pIRES-1neo plasmid was combined with the tropoelastin cDNA and ligated with high concentration T4 DNA Ligase (New England Biolabs) overnight in a cold water bath to create the pIRES-elastin expression plasmid.

*E. Coli* Transformation and Plasmid Amplification

Plasmid DNA was transformed into competent jm109 *E. coli* bacteria for selection and amplification. Bacteria cultures in the state of active growth were made competent with transformation buffer (TFB) and stored on ice for up to 72 hours before being used. Plasmid DNA was added to the competent cells in a 1:20 (v:v) ratio, and the solution was stored on ice for 20 to 30 minutes. The solution was heat shocked in a 42° C. water bath for exactly 90 seconds and then chilled on ice for 2 minutes. Luria-Bertani (LB) media was added to the bacteria solution in a 4:1 (v:v) ratio, and the cultures were incubated at 37° C. for an hour to allow the bacteria to recover and express the ampicillin resistance marker. The transformant cell solution was then spread over the surface of LB agar culture plates containing 100 µg/ml ampicillin. After 24 hours incubation at 37° C., newly formed colonies growing on the agar plates were isolated and regrown in LB media containing ampicillin (100 µg/ml) for plasmid analysis. Competent cells receiving known quantities of a standard plasmid solution and blank DNA-free solutions were used as positive and negative controls for each experiment. High quality reagents and meticulously cleaned glassware were used to help maximize the competency of the bacteria cultures.

Plasmid Analysis and Gene Sequencing

Plasmids isolated from transformed bacteria using a DNA purification kit (Amersham Pharmacia Biotech) were assessed by restriction enzyme mapping to screen transfected colonies. Purified plasmids were added to individual and multiple combinations of restriction enzymes (New England Biolabs) buffered according to the manufacturer's recommendations and incubated in a 37° C. water bath for 90 min. After the addition of bromophenol loading buffer, the enzyme digests were loaded into an agarose/ethidium bromide gel and run in TAE buffer at 120 V for 60 min. An UV transilluminator was used to visualize the DNA bands, and images were captured on Polaroid film or digitally via a CCD camera. Once a plasmid had been determined to contain the elastin cDNA gene in the correct orientation, the plasmid was sequenced to test for mutations and misincorporated nucleotides.

Example 6

Introduction of DNA into Mammalian Cells

The pIRES-elastin plasmids were transfected into the nuclei of eukaryotic cells using liposomal-mediated and lipid-based delivery systems. Murine NIH/3T3 fibroblasts were transfected using LipofectAMINE cationic liposomes (Clontech) and cultured under geneticin selective pressure to produce stable clones. HDFs were transfected via the FuGENE™ 6 lipid delivery reagent (Roche Diagnostics Corporation, Indianapolis, Ind.) and cultured without selective pressure to produce transiently modified cells.

NIH/3T3s were cultured in supplemented DMEM to 75% confluency on tissue culture plastic as previously described. Liposomes were constructed by combining 100 µg of LipofectAMINE transfection reagent with ~60 µg of pIRES-elastin plasmid DNA in 30 ml of serum-free DMEM media. Cells were rinsed in PBS to remove serum proteins which can interfere with the transfection and incubated in the liposome/DNA media for 2 to 4 hours to ensure plasmid uptake. They were then rinsed again in PBS to remove the liposome complexes which could eventually cause cytotoxicity and returned to standard culturing conditions for recovery. Geneticin antibiotic (G418) (Gibco BRL) was added to the media at a concentration of 500 µg/ml twenty-four to seventy-two hours following the transfection to select for stable transformants. G418 interferes with a cell's ability to express proteins and consequently kills any cell which has not properly incorporated the plasmid DNA encoding for antibiotic resistance into its genetic structure.

HDFs were cultured in supplemented DMEM to 75% confluency on tissue culture plastic as previously described. Transfection complexes were formed by adding plasmid DNA (1 µg per 3 µl FuGENE reagent) to a 3% FuGENE 6, serum-free DMEM solution (v:v) in a sterile microcentrifuge tube. The contents of the tube were gently mixed and incubated at room temperature for 20–25 minutes. The complex mixtures were then added dropwise to the cell culture flasks (0.125 µg DNA per $cm^2$ growth area) and incubated for 24–48 hrs. One of the advantages associated with using this lipid delivery system was the ability to use serum protein supplements during the transfection process. This decreased cytotoxicity complications and allowed for extended transfection complex incubations. Following the incubations, the growth media was replaced. Transfected HDFs were typically evaluated under transient expression culture conditions 2–5 days following transfection.

Example 7

De Novo Expression Experiments

Monolayer experiments were employed to investigate levels of elastin expression in native and genetically modified cells. Unless indicated otherwise, cells were cultured on treated tissue culture plastic. When growth factors were utilized, they were administered as soluble constituents in the culture media. Two dimensional investigations were generally conducted as destructive experiments at fixed end points.

Three dimensional experiments were employed to investigate the production rates and structural orgarization of elastin in collagen-based constructs. When genetically modified cells were used, they were generally transfected while still in monolayer culture. Following transfection, the cells were suspended distributed into collagen gels as previously described. This provided for increased control in determining cell populations, regulating growth phases, and standardizing transport delivery rates. Specific assays were used to characterize cell and construct functionality.

As described previously, the cDNA encoding the human tropoelastin gene was incorporated into pIRES-1neo bicistronic mammalian expression vector for recombinant elastin production. Following EcoRI digestion and agarose gel electrophoresis purification, the ~2.2 kb tropoelastin segments were ligated into dephosphorylated EcoRI sites in the MCS of the expression plasmid. Dephosphorylation was used to reduce the chances of religation in the pIRES-1neo plasmids. Following the construction of the pIRES-elastin plasmids, jm109 E. coli bacteria were transformed with the newly made vectors and grown into distinct colonies on agar plates under ampicillin selective pressure. The ampicillin eliminated all bacteria that were not properly transformed with an intact vector but did not distinguish between the plasmids which contained the target gene and those that did not.

Figure 29:
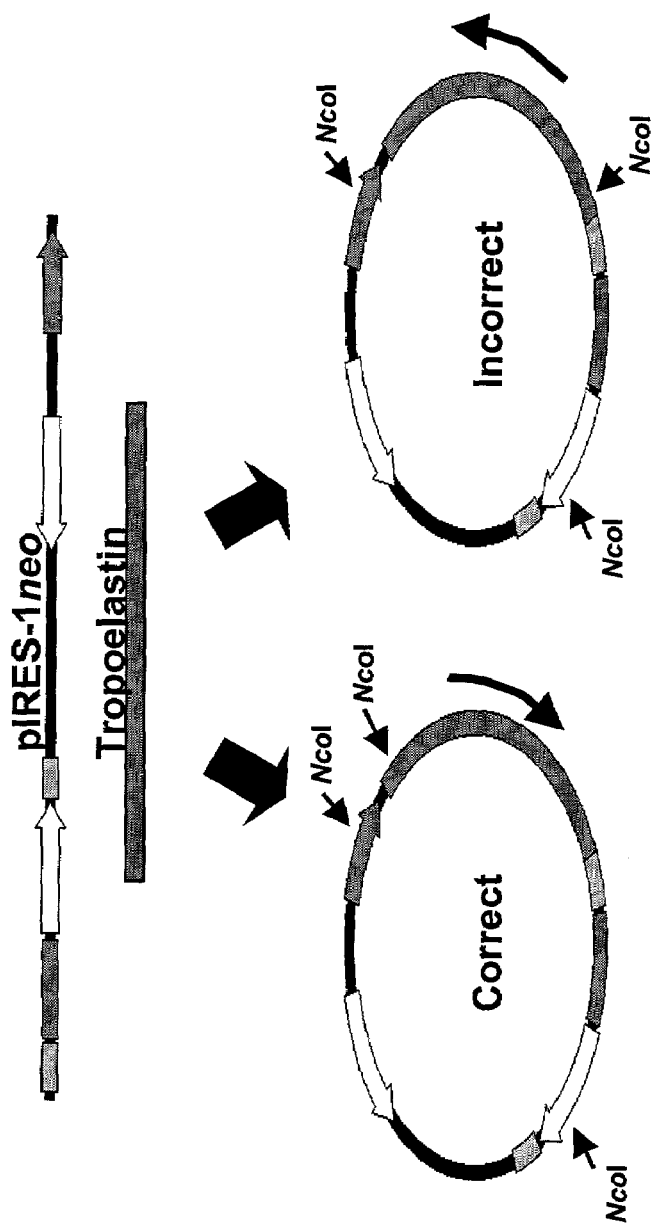
FIG. 29 is a schematic of the incorporation of tropoelastin cDNA into pIRES-1neo.

Since EcoRI sites existed at both the 5' and 3' ends of the tropoelastin cDNA, the gene was able to ligate into the pIRES-1neo vector in either the forward or reverse directions, as shown in FIG. 29. When plasmid vectors containing tropoelastin DNA in the correct orientation were digested with NcoI restriction enzymes, three segments with lengths of 324, 3388, and 3741 basepairs formed. When plasmid vectors containing tropoelastin DNA in the incorrect orientation were digested with NcoI restriction enzymes, three segments with lengths of 1541, 2524, and 3388 basepairs formed. Individual jm109 colonies growing on the agar plates were screened via NcoI restriction enzyme mapping to identify colonies producing pIRES-elastin plasmids with the proper gene orientation. Based on restriction enzyme digestion, the colonies in lanes five, six, and seven appear to have incorporated the tropoelastin cDNA in the incorrect orientation. Similarly, the colonies in lanes three and four appear to have incorporated the cDNA into the plasmid in the correct orientation. Lanes one and two contain NcoI digests of pElastin and pIRES-1neo plasmids which were used as controls. The Lambda-BstEII molecular weight ladder (New England Biolabs) was run in lane eight. Plasmid DNA was collected from the two colonies with the correct tropoelastin orientation and sequenced at Loftstrand Labs using the Sanger method and at the Emory DNA Sequencing Facility using dye terminator cycle sequencing methods with fluorescently tagged nucleotides.

As described, pIRES-elastin plasmids were transfected into NIH/3T3 fibroblasts and passage 5–7 HDFs using cationic liposome-mediated and lipid-based transfection delivery systems, respectively. Transfected NIH/3T3s were cultured in DMEM supplemented with 10% calf serum and 500 µg/ml G418 antibiotic to select cells displaying stable plasmid expression. The concentration of G418 was determined using a dose response curve. At levels above 300 µg/ml, all unmodified 3T3s died within 72 hrs following the introduction of the antibiotic. When grown under 500 µg/ml G418 selective pressure, the majority of transfected NIH/3T3s died off within six to seven days. This indicated that a fairly low percentage of cells had incorporated the plasmid. Over the next few weeks, fifteen transfected pIRES-elastin NIH/3T3 colonies were isolated. The antibiotic resistance in these cells indicated that they had incorporated the plasmids into their chromosomal DNA.

Recombinant HDFs were cultured under transient conditions in the standard FBS supplemented DMEM media described previously. By using a lipid-based delivery system which remains functional in the presence of serum proteins, it was possible to minimize cytotoxicity. Additionally, the lipid-based system did not appear to adversely affect the HDF transfection efficiency compared to the cationic liposme-mediated system as demonstrated by slightly elevated reporter enzyme activity levels when cells were transfected with the pGL3-Control luciferase vector. Transient expression in recombinant HDFs was utilized to minimize cell passaging effects which would have accompanied the stable clone selection process. Analogous populations of untransfected cells and cells transfected with the unmodified pIRES-1neo plasmid were examined for comparison.

Competitive RT-PCR analysis revealed a marked increase in tropoelastin mRNA levels in cells transfected with pIRES-elastin as compared to untransfected or pIRES-1neo transfected controls. All of the fifteen NIH/3T3 colonies examined exhibited a strong band following PCR indicating that they were producing tropoelastin mRNA. No bands for tropoelastin could be visualized in NIH/3T3 control samples after 28 PCR cycles. While basal levels of tropoelastin mRNA were discernible in unmodified nHDF, transfection with the pIRES-elastin vector was able to increase the mRNA production level by several orders of magnitude.

Figure 30:
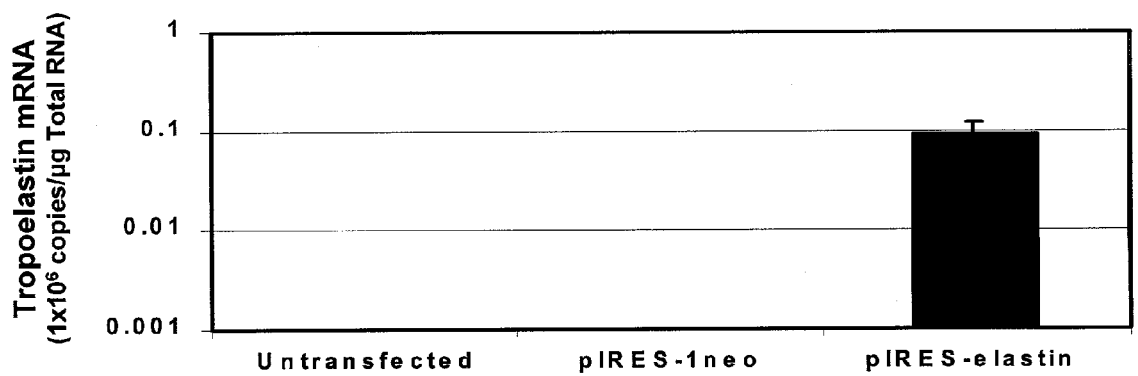
FIG. 30 is a chart showing tropoelastin mRNA expression.
Figure 30:
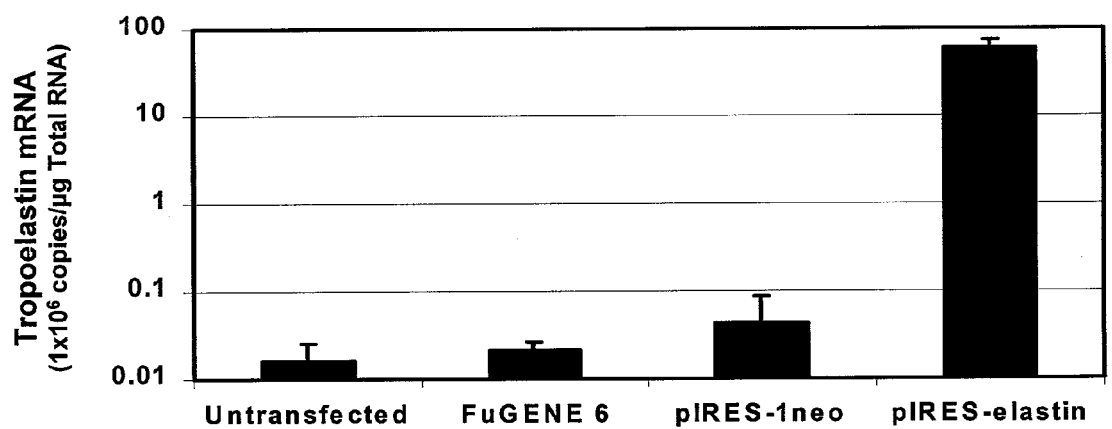

Monolayers of NIH/3T3s jumped from undetectable levels of mRNA expression to 92,500 copies/µg total RNA following stable transfection, see FIG. 30. Similarly, tropoelastin mRNA expression in transiently transfected monolayers of HDFs increased from below 18,000 to 58,000,000 copies/µg total RNA ($p<0.001$ vs. Untransfected HDFs, $p<0.001$ vs. FuGENE-6 Mock-transfected HDFs, $p<0.001$ vs. pIRES-1neo Mock-transfected HDFs) forty-eight to seventy-two hours following transfection.

Cellular Function of Transfected NIH/3T3s and HDFs

Various types of cellular functionality were assessed on transfected NIH/3T3s and HDFs grown in both monolayer and three dimensional collagen structures to identify possible secondary effects associated with genetic recombination. NIH/3T3s were characterized for cell proliferation and construct gel compaction. HDFs were characterized for construct gel compaction and expression stability.

Analysis of NIH/3T3 monolayers indicated that cells transfected with pIRES-elastin divided at slower rates and were less likely to grow in multiple layers than their untransfected counterparts. When seeded at subconfluent conditions, transfected fibroblasts in G418 supplemented media grew slower compared to unmodified cells (Transfected w/G418—47.1 hr/doubling vs. Untransfected—19.1 hr/doubling, $p<0.0001$). The division time of the transfected cells dropped to 36.6 hr/doubling when the antibiotic selective pressure was removed ($p<0.08$ vs. Transfected w/G418) but still remained significantly lower than in the unmodified controls ($p<0.0001$ vs. Untransfected). Populations of both transfected and untransfected cells seeded under highly confluent conditions showed little or no division and may have even decreased slightly in number over the course of seven days.

Figure 31:
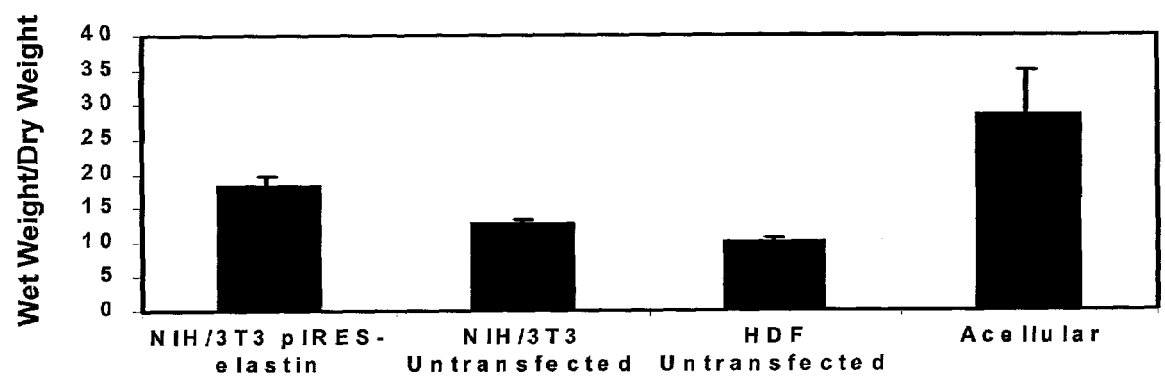
FIG. 31 is a chart showing the gel compaction of disk constructs.

Genetic modification also affected the abilities of NIH/3T3s to compact collagen gels. When seeded into 2 ml disk constructs at $1\times10^6$ cells/ml and cultured for eleven days, unmodified NIH/3T3s were able to remodel and compact their surrounding matrix, but to a lesser extent than unmodified HDFs. This capacity for gel compaction decreased even further when the NIH/3T3s were transfected with the pIRES-elastin plasmid. FIG. 31 shows the gel compaction data as assessed by the ratio of wet weight to dry weight. As the constructs developed, the edges of the disk compacting gels frequently curled up. This made an estimation of compaction using dimensional analysis difficult.

Since the combined dry weight of the collagen matrix and cellular components remained relatively constant throughout the eleven days of culturing while the wet weight was determined primarily by the fluid contained in the gel, this ratio could be used to estimate the volume of each disk construct regardless of its geometry. The wet weight to dry weight of unmodified NIH/3T3s was 1.27-fold higher than in HDFs ($p<0.001$). The same ratio in stably transfected cells was 1.81-fold higher than in HDFs ($p<0.001$) and 1.42-fold higher than in unmodified NIH/3T3s ($p<0.001$). All cell types, however, elicited statistically significant gel compaction compared to acellular constructs ($p<0.02$ vs. Transfected NIH/3T3s, $p<0.003$ vs. Unmodified NIH/3T3s, $p<0.002$ vs. HDFs).

Figure 32:
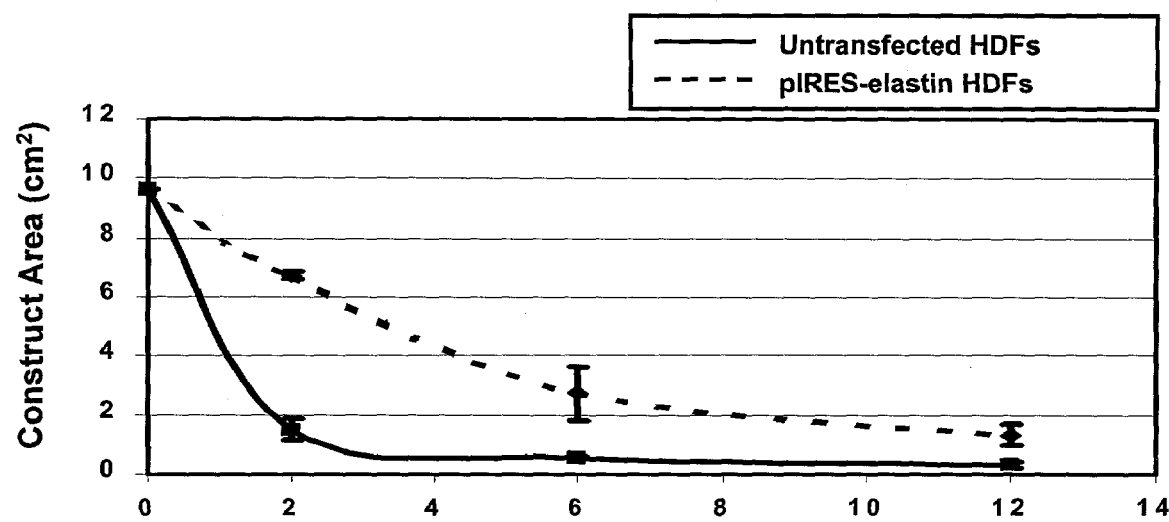
FIG. 32 is a chart showing the gel compaction of disk constructs containing HDFs.

Cellular function in transiently transfected HDFs incorporated into collagen disk constructs forty-eight hours following transfection was also affected by genetic modification. Shown in FIG. 32, the degree and rate of gel compaction in the transfected constructs was less vigorous than in the control constructs. While unmodified cells produced large degrees of compaction in the initial hours following construct fabrication, the rate of change in area dropped off in ensuing days. Recombinant cells, on the other hand, compacted their surrounding matrices more slowly at first but gradually caught up with subsequent culturing.

Figure 33:
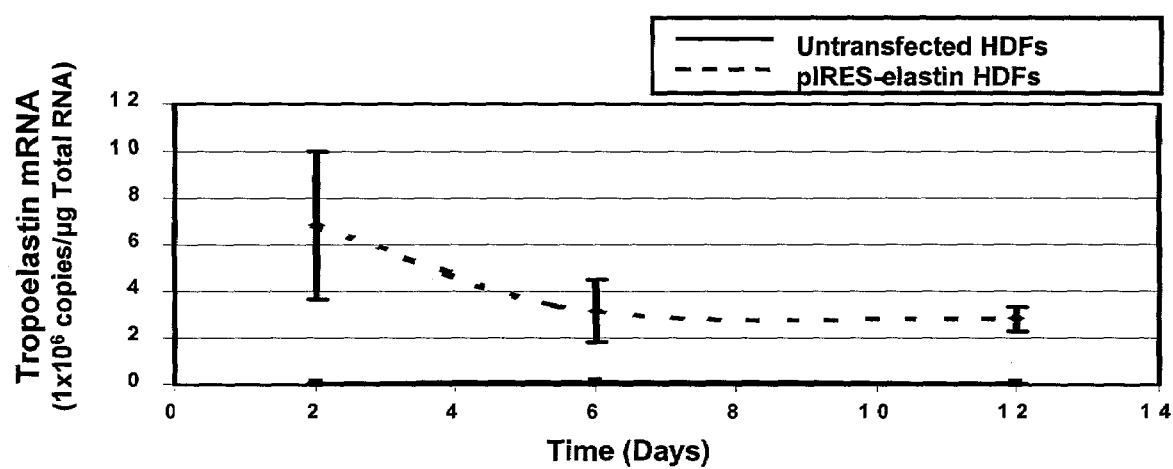
FIG. 33 is a graph of tropoelastin mRNA expression.

Stability of the plasmid expression in disk constructs seeded with transiently transfected HDFs is shown in FIG. 33. During the twelve days of culturing, the observed mean tropoelastin mRNA levels dropped from $6.8\times10^6$ to $3.2\times10^6$ copies/μg total RNA. While this change did not reach statistical significance ($p<0.08$), the trend indicated that some expression loss may be taking place. Even with the drop, however, the expression in recombinant HDFs remained 40.5-fold higher than in untransfected control constructs after twelve days of culturing ($p<0.00 1$)

Example 8

Fibrin-Based Constructs

Fibrin and fibrin-collagen constructs were prepared. Briefly, fibrinogen and ε-amino caproic acid (ACA) were combined with thrombin and FBS and RASMs in DMEM culture media containing penicillin (100 IU/ml) and streptomycin (100 μg/ml) to form fibrin gels. These gels were constructed in the same tubular molds as the standard collagen-based constructs and initially contained 2 mg/ml fibrinogen, 2 mg/ml ACA, and 0.2 U/ml thrombin. The tubular molds were sealed with ventilated caps and incubated at 37° C. for 30 minutes. Once the fibrin had polymerized, the gels were removed from the molds and cultured in complete DMEM growth media containing 2 mg/ml ACA and an additional 0.292 mg/mL (2 mM) L-glutamine. ACA was added as an inhibitor of the Lys-Plasmin and Glu-Plasmin enzymes that are released by the cells and can degrade fibrin. L-glutamine is an energy and carbon source used by most cells (Freshney 2000) and was a standard additive in Cummings' experiments that was used to supplement the 4 mM L-glutamine present in the DMEM.

Mixed Gels

Mixed gels containing combinations of fibrin and collagen were also examined as scaffold matrices. These constructs were constructed to contain equivalent initial concentrations of fibrin (2 mg/ml) and collagen (2 mg/ml). All constructs were statically cultured six days prior to analysis on adherent silicon tubes. The silicon tubes provided a distensible inner barrier which could be cyclically inflated during experiments involving mechanical conditioning.

Example 9

Collagen-Based Construct Sleeve Hybrids

The present invention can be made with synthetic support structures such as Dacron sleeves to provide mechanical integrity to collagen gel constructs, this embodiment uses collagen-based support structures. Crosslinking was also investigated as a means of further augmenting the mechanical strength and stability of the constructs.

Sleeve Fabrication

Acellular, biological support sleeves were fabricated using the glass capillary tube mandrel assemblies previously described. Rat collagen, DMEM, sodium hydroxide, and PBS (pH 7.4) were combined on ice to produce a solution with a 2.0 mg/ml final collagen concentration. The solutions were poured into the glass test tube molds and transferred to a 37° C. incubator and incubated for 1 hr to ensure gelation of the collagen fibers. The acellular constructs were then carefully removed from the test tubes and dehydrated overnight on a rotating metal rod. The rotation was necessary to ensure uniform drying of the sleeve. Sleeves were either used as such, i.e. uncrosslinked (UnXL), or following one of the crosslinking treatments described below.

Glutaraldehyde Crosslinking (Glut)

Sleeves were rinsed briefly in PBS to remove excess DMEM salts and amino acids and submerged in a PBS solution containing 0.5% glutaraldehyde (Sigma). Samples were incubated under gentle agitation overnight at 4° C. to ensure uniform crosslinking throughout the sample. The sleeves were then rinsed 3× in PBS followed by two 24 hr PBS washes at 4° C. to remove residual glutaraldehyde.

Dehydrothermal Crosslinking

Sleeves subjected to dehydrothermal crosslinking (DHT) were placed in test tubes and crosslinked in a silica gel desiccator. Air was evacuated from the chamber with a Gast laboratory pump, (Gast Manufacturing, Benton Harbor, Mich.) and the desiccator was heated at 120° C. in an Econotherm Precision Scientific Laboratory Oven (Model 1025) (Winchester, Va.)for either one (DHT-1 d) or five (DHT-5 d) days.

Ultraviolet Crosslinking

Sleeves subjected to ultraviolet crosslinking (UV) were irradiated in a Fisher Biotech™ Oven (FB-UVXL-1000, Fisher, Pittsburgh, Pa.) under a bank of five 8-watt UV lights operating at 254 nm. Samples were placed on sheets of aluminum foil and exposed for 60 min (UV-60m) or 120 min (UV-120 m). Each sleeve was rotated 90 degrees every 15 min to facilitate uniform crosslinking.

Hybrid Construct Formation

The formation of the CSH was accomplished using a modified version of the protocol described in Section 3.1.2. Acellular sleeves were washed briefly in PBS while still on the mandrel to remove excess DMEM salts and amino acids. Suspensions of HDFs and rat collagen were created as previously described and poured into the test tube molds. The mandrel assemblies containing the support sleeves were inserted, and the suspensions were gelled at 37° C. for 45 minutes. Once gelled, the CSHs were removed from the molds and cultured statically in suspension petri dishes for 8 or 23 days prior to analysis. As the cells remodeled their matrix, the cellular component of the CSH compacted about the inner support sleeve. Unreinforced constructs constructed without support sleeves were used as controls throughout the experiments.

Collagen-Based Construct-Sleeve Hybrids (CSHs)

The CSH grafts investigated consisted of dehydrated, crosslinked acellular sleeves surrounded by layers of collagen embedded cells. The sleeves took advantage of findings that linked the density of collagen and crosslinking treatment with increase strength. Glutaraldehyde incubation (Glut), dehydrothermal treatment (DHT), and ultraviolet irradiation (UV) were selected to identify appropriate methods of crosslinking the acellular sleeves. HDFs embedded in Type I rat collagen were used to fabricate the CSHs. CSH grafts were analyzed through collagen gel compaction assessment, histological and viability staining, and mechanical testing.

Acellular Collagen Support Sleeves

Acellular sleeves were first examined without the cell-seeded components to determine which crosslinking treatments might be most effective to use in the CSHs. During the dehydration process, the acellular collagen structures transformed from three-dimensional, 3.75 mm thick hydrogels into thin paper-like sleeves which were approximately 50 μm thick. As the moisture was removed, the gels experienced a 99.7% reduction in weight. By allowing the ends of the gels to remain adherent to the mandrel stoppers, it was possible to induce essentially unidirectional radial compaction thus creating sleeves with predictable final dimensions. Upon reintroduction to aqueous environments, the sleeves swelled slightly but maintained their macroscopic geometries even after extended incubation periods (>6 weeks).

While the various crosslinking treatments did not evoke statistically significant changes in the dimensions of the dehydrated sleeves, some alterations in physical appearance occurred. Both glutaraldehyde and DHT elicited a slight yellow discoloration of the collagen. The effects of UV treatment were more subtle as no observable changes were evident.

Stress-strain profiles of all sample types revealed that the sleeves exhibit relatively linear behaviors in the circumferential orientation up to the point of catastrophic failure. Samples typically strained between 15–20% prior to reaching their peak stresses. Crosslinking treatment augmented the mechanical properties of the support sleeves.

Circumferential peak failure stresses of all crosslinked specimens were significantly higher than those of their uncrosslinked counterparts. The mean UTS of Glut sleeves increased 3.4-fold ($p<0.002$) versus control. UV-60 m and UV-120 m sleeves increased 2.0-fold ($p<0.03$) and 2.1-fold ($p<0.03$) from control levels, respectively. DHT-1 and DHT-5 sleeves increased 2.8-fold ($p<0.03$) and 2.9-fold ($p<0.006$), respectively. The linear moduli stiffness parameter increased in all crosslinking treatment groups. The mean modulus of Glut sleeves increased 3.3-fold ($p<0.005$) compared to untreated controls. UV-60 m and UV-120 m sleeves increased 2.3-fold ($p<0.002$) and 3.3-fold ($p<0.01$), respectively. DHT-1 and DHT-5 sleeves increased 3.1-fold ($p<0.02$) and 3.7-fold ($p<0.001$), respectively. While extending the duration of UV and DHT crosslinking tended to increase the mechanical parameters, variations within the UV and DHT treatment groups were not statistically significant.

The direction the samples were oriented during analysis also affected the outcomes of the uniaxial tensile tests. When in a longitudinal (L) orientation, peak stresses of uncrosslinked (UnXL) support sleeves were 3.6-fold higher than the corresponding stresses of samples in a circumferential (C) orientation (C→3.0 MPa vs. L→10.8 MPa, $p<0.03$). Likewise, linear moduli were 4.6-fold higher in the longitudinal direction than in the circumferential orientation (C→17.9 MPa vs. L→81.9 MPa, $p<0.01$). While the statistical correlations were not as strong, sleeves crosslinked with glutaraldehyde displayed similar trends with respect to axis orientation: Peak stresses (C→10.2 MPa vs. L→14.9 MPa, $p<0.10$); Linear moduli (C→59.8 MPa vs. L→181.1 MPa, $p<0.01$). These results indicate that preferential alignment of collagen fibers takes place as the sleeve supports dehydrate on the glass mandrel. Additionally, it suggested that the mechanical properties may be further enhanced by controlling and optimizing the fiber orientation during sleeve formation.

Based on the results of the sleeve support studies, glutaraldehyde crosslinking was selected as a model treatment method for the subsequent CSH experiments. While all of the methods showed promise, the effects of glutaraldehyde were the most profound and consequently, could help to determine the upper limitations of a CSH approach to tissue engineering a vascular graft.

Gel Compaction Data

Following the addition of the second cell-seeded layer, the CSHs compacted rapidly in both the radial and longitudinal directions. After eight days of culture, uncrosslinked CSHs occupied less than 6% of their original volume. This remodeling process continued with time until only 3.2% of the original volume remained at day twenty-three. Crosslinking the sleeves with glutaraldehyde resulted in a significant decrease in compaction at day eight (Glut→7.4% vs. UnXL→5.6%, $p<0.02$), but by day twenty-three the compaction levels were statistically indiscernible (Glut→3.8% vs. UnXL→3.2%, $p<0.63$). The wall thicknesses of the Glut and UnXL CSHs were analogous at both measured time points (Day 8: Glut⇒0.75 mm vs. UnXL⇒0.75 mm, p<0.999; Day 23: Glut⇒0.44 mm vs. UnXL⇒0.47 mm, p<0.999).

Histological and Viability Staining

Histological examination was used to assess the distribution of cells and matrix proteins throughout the constructs and to evaluate the levels of integration between the layers of the CSHs. H&E staining revealed that the support sleeves could be easily distinguished from the cell seeded sections at both the eight and twenty-three day time points. Sleeves treated with glutaraldehyde crosslinking presented a vivid red while uncrosslinked sleeves were stained a bright, but less intense, pink. Only faint staining of the reconstituted collagen was observed in the cell seeded layers. While the majority of cells were localized about the outer surface of the construct, regions of cell infiltration into the sleeve supports were observed indicating that integration had started to occur.

Live-dead examination of the CSHs showed that incorporation of a support sleeve had no noticeable effect on cell viability in cell seeded layer. Cells tended to migrate/proliferate on the outer construct surface as the nutrient supply was provided from the media surrounding the constructs. Consequently, few cells were found on the sleeve supports. Cells found on uncrosslinked sleeves tended to present green indicating viability while many of the cells found on glutaraldehyde crosslinked sleeves were stained red indicating cell death. All constructs exhibited greater than 95% overall cell viabilities.

Endothelial Cell Seeding

Endothelial cell seeding studies were performed to investigate whether these cells would adhere to the CSH lumens. Endothelial cells seed well onto the support sleeves. In the uncrosslinked samples, protruding cell membrane extensions could be clearly visualized indicating that the cells were healthy and fully spread across the surface. While the endothelial cells seeded on glutaraldehyde treated sleeves continued to appear healthy, their membrane protrusions were not as apparent as in the UnXL sleeves. This could have been due in part to signal loss in the background noise created in the glutaraldehyde crosslinking process.

Uniaxial Tensile Testing

The CSH approach dramatically alters the mechanical behaviors of reconstituted collagen grafts. While typical stress-strain profiles of all construct types displayed the characteristic non-linear toe regions followed by a quasi-linear strain regime which is typical of native arteries and other biological tissues (Fung 1993), the degree of strain and loading levels were markedly different for the different construct types. Furthermore, while the UnXL CSHs and unreinforced control constructs experienced substantial yielding and plastic deformation, Glut CSHs were highly linear ($R^2$=0.999) up to the point of catastrophic failure.

The ultimate stress parameters of the constructs underscore the differences of the stress-strain profiles. After eight days of culture, the peak stresses of uncrosslinked and Glut CSHs were 8.9-fold ($p<0.0001$) and 49.3-fold ($p<0.0001$) higher, respectively, than in the control constructs. These differences increased to 11.0-fold (UnXL, $p<0.0001$) and 65.2-fold (Glut, $p<0.0001$) fold by day twenty-three relative to the day twenty-three control as the cells continued to compact and remodel the constructs. Furthermore, Glut CSHs were 5.5-fold ($p<0.001$) and 5.9-fold ($p<0.0001$) higher than uncrosslinked CSHs at days eight and twenty-three, respectively.

The linear moduli of CSH exhibited similar increases versus the unreinforced controls. After eight days of static culturing, the linear moduli of uncrosslinked and glutaraldehyde treated CSHs were 6.2-fold ($p<0.0001$) and 163-fold ($p<0.0001$) higher, respectively, than in the control constructs. After twenty-three days of culturing, the modulus parameters were 16.8-fold ($p<0.0001$) and 156-fold ($p<0.0001$) higher in uncrosslinked and glutaraldehyde treated CSHs, respectively, than in control constructs. Crosslinking the CSHs created 26.1-fold ($p<0.0001$) and 9.3-fold ($p<0.0001$) higher linear moduli compared to untreated CSHs at days eight and twenty-three, respectively. Clearly, the use of a CSH approach in both the uncrosslinked and crosslinked forms improved the mechanical performance of vascular constructs. Additionally, these results suggested that these benefits may persist beyond the three week time points examined in this study.

As described previously, the areas under the stress-strain curves were used to give an idea of the degree of toughness in different construct samples. The energy required to bring a construct to the point of yielding was 11.0-fold ($p<0.0001$) and 21.7-fold ($p<0.0001$) higher in uncrosslinked and glutaraldehyde treated CSHs than in control constructs, respectively, after eight days of culture. Similarly, this energy was 14.9-fold ($p<0.0001$) and 40.4-fold ($p<0.0001$) higher after twenty-three days of culture. Glutaraldehyde treatment of the CSHs created a 2.0-fold ($p<0.76$) and 2.7-fold ($p<0.23$) in the mean observed yield energy parameters at days eight and twenty-three, respectively.

After eight days of culture, the energy required to bring samples to failure was 6.8-fold ($p<0.0001$) and 7.4-fold ($p<0.0001$) higher in uncrosslinked and glutaraldehyde treated CSHs than in collagen controls, respectively. These values were 13.4-fold ($p<0.0001$) and 23.1-fold ($p<0.0001$) higher after twenty-three days of culture. Glutaraldehyde treatment of the CSHs created no change in the failure energy parameters at either day eight ($p<0.999$) or day twenty-three ($p<0.83$).

The ratios of failure to yield energies indicated that these constructs experienced vary different modes of failure. The energy ratio of uncrosslinked CSHs was 1.86 and 1.78 at days eight and twenty-three, respectively. With glutaraldehyde treatment, the ratio dropped to 1.02 ($p<0.09$ vs. UnXL CSH) and 1.10 ($p<0.02$ vs. UnXL CSH) at the two time points indicating that the crosslinked constructs failed abruptly with essentially negligible plastic deformation. Collagen control constructs, on the other hand, had relatively high energy ratios—2.95 and 1.93 at days eight and twenty-three—indicating that large degrees of plastic deformation took place prior to ultimate failure. These values were statistically different from the glutaraldehyde treated CSHs at both time points (8 Day⇒$p<0.0001$, 23 Day⇒$p<0.007$) and from the UnXL CSHs after eight days ($p<0.03$) but not twenty-three days ($p<0.99$). There were no statistical differences observed with variations in the culturing duration of Glut CSHs ($p<0.999$) or UnXL CSHs ($p<0.9995$). The energy ratios in the unreinforced constructs, however, dropped from day eight to day twenty-three ($p<0.005$).

Viscoelastic Testing

While data from the uniaxial tensile testing clearly showed that dehydrating a collagen gel to form a CSH can augmented the overall mechanical strengths of TE vascular grafts, they were unable to provide information pertaining to the viscoelastic natures of the constructs. Creep and stepwise stress relaxation were performed as static viscoelastic tests to characterize these viscous and elastic properties. In the creep testing experiments, the applied mechanical load was set equal to one third of the estimated ultimate tensile stress of each construct. In the stepwise stress relaxation experiments, five discrete strain displacements were introduced to each sample at six minute intervals. Burger's four element mechanical model was fit to the data and used to elicit quantitative viscoelastic parameters.

As seen in the uniaxial tensile tests, control constructs without a collagen reinforcement sleeve were more susceptible to larger degrees of instantaneous strain than either the uncrosslinked or glutaraldehyde treated CSHs. As time passed and the transient behaviors decayed, strain in the unreinforced control constructs settled into a constant deformation rate which left unchecked eventually resulted in construct failure. Uncrosslinked CSHs exhibited some instantaneous deformation and a transient decay, but there was a marked reduction in the level of long term strain. Glutaraldehyde treated CHSs exhibited negligible instantaneous deformation and transient decays which were unable to be resolved on the observation time scales. Likewise, long-term strain behavior was essentially nonexistent.

The creep stress-strain data was fit to Burger's four element viscoelastic model. This allowed the observations perceived from the creep profiles to be expressed quantitatively. The elasticity parameter $R_1$ defined by the instantaneous deformations caused by the introduction of a step load became larger when the constructs were combined with uncrosslinked support sleeves and cultured for eight (4,200 Pa vs. 184,000 Pa, 43.8-fold increase, $p<0.05$) and twenty-three days (12,700 Pa vs. 230,000 Pa, 18.1-fold increase, $p<0.04$). This rise continued to 36.5 MPa (8,700-fold increase, $p<0.0001$ vs. control; 199-fold increase, $p<0.003$ vs. UnXL CSH) at day eight and 2,620 MPa (206,000-fold increase, $p<0.43$ vs. control; 11,400-fold increase, $p<0.43$ vs. UnXL CSH) at day twenty-three when the support sleeves were treated with glutaraldehyde. Large p-values at day twenty-three were caused by large variance in the Glut CSH data.

Similarly, the elasticity parameter $R_2$ and viscosity coefficient $\eta_2$ which defined the transient creep domain frequently exhibited statistically significant rises when collagen constructs were combined with uncrosslinked collagen support sleeves ($R_2$: 8 Days⇒12.1-fold increase, $p<0.005$; 23 Days⇒21.0-fold increase, $p<0.02$; $\eta_2$: 8 Days⇒28.1-fold increase, $p<0.001$; 23 Days⇒27.8-fold increase, $p<0.28$). The same was true with glutaraldehyde treated CSHs ($R_2$: 8 Days⇒235-fold increase, $p<0.001$ vs. Control; 19.4-fold increase, $p<0.003$ vs. UnXL CSH; 23 Days⇒249-fold increase, $p<0.19$ vs. Control; 11.9-fold increase, $p<0.22$ vs. UnXL CSH; $\eta_2$: 8 Days⇒35.0-fold increase, $p<0.001$ vs. Control; 1.25-fold increase, $p<0.47$ vs. UnXL CSH; 23 Days⇒89.1-fold increase, $p<0.14$ vs. Control; 3.21-fold increase, $p<0.31$ vs. UnXL CSH). These three parameters are important in that they describe the short-term compliance behaviors that take place with the pressure surges as blood flow is pumped through the construct.

The final viscosity coefficient $\eta_1$ was representative of the unrecoverable, long-term strain behavior. The values jumped 137-fold ($p<0.006$) and 34.3-fold ($p<0.1$ 1) when unreinforced collagen-based control constructs were combined with an uncrosslinked support sleeve and cultured for eight and twenty-three days, respectively. Again, the rise from control construct levels continued to increase to (Day 8: 53,900-fold increase, $p<0.08$ vs. Control; 394-fold increase, $p<0.19$ vs. UnXL CSH; Day 23: 18,900-fold increase, $p<0.001$ vs. Control; 552-fold increase, $p<0.001$ vs. UnXL CSH) when the support sleeves were treated with glutaraldehyde. Length of time in culture did not effect any of the Burger's model parameters.

As $\eta_1$ increases towards infinity, the constructs exhibit less and less sustained strain until Burger's viscoelastic model is eventually reduced to the model for a Standard Viscoelastic Solid. In maintaining proper vascular function, it is necessary to restrict the time-dependent creep behaviors to the short-term, recoverable domains. If the $\eta_1$ viscosity coefficient is too low, the construct will behave as a viscoelastic fluid, form aneurisms, and rupture upon implantation.

Stress relaxation testing performed the inverse characterization as the creep analysis and was used to complement the creep analysis studies. Initial stress relaxation moduli, calculated from the stress-strain relationships immediately following each step displacement, resulted from a combination of both the viscous and elastic elements of the constructs. The initial moduli jumped 9.3-fold ($p<0.0007$) and 13.4-fold ($p<0.0001$) when unreinforced collagen-based control constructs were combined with an uncrosslinked support sleeve for eight and twenty-three days of culture. These values increased again (8 Days: 55.3-fold, $p<0.0001$ vs. Control; 5.9-fold, $p<0.0003$ vs. UnXL CSH; 23 Days: 107-fold, $p<0.0001$ vs. Control; 8.0-fold, $p<0.0001$ vs. UnXL CSH) when the CSH support sleeves were treated with glutaraldehyde.

The relaxed stress relaxation moduli were defined by the stress-strain relationships six minutes after each step displacement—just before the introduction of the subsequent strain jump. By this time the transient effects of the material's viscous elements were assumed to have decayed away leaving only the elastic components to bear the loads. The relaxed moduli of uncrosslinked CSHs were 18.8-fold ($p<0.0002$) and 30.5-fold ($p<0.0001$) higher than unreinforced control constructs after eight and twenty-three days of culturing. Likewise, the moduli were higher in glutaraldehyde treated CSHs than in the control constructs (8 Days: 214-fold increase, $p<0.0001$ vs. Control; 11.4-fold increase, $p<0.0001$ vs. UnXL CSH; 23 Days: 461-fold increase, $p<0.0001$ vs. Control; 15.1-fold increase, $p<0.0001$ vs. UnXL CSH).

Ratios of the two stress relaxation moduli were used to identify the percentage of the mechanical strength in each construct which resulted from the viscous natures and from the elastic natures of the materials. The high initial to relaxed moduli ratios of the unreinforced collagen constructs indicated that a majority of their resistance to deformation was the result of their highly viscous fluid-like natures. In glutaraldehyde crosslinked CSHs, these ratios were 1.45 ($p<0.006$ vs. Control) and 1.37 ($p<0.0001$ vs. Control) for the two culturing time points investigated indicating that the materials were dominated by their elastic properties. The intermediate ratio values for the uncrosslinked CSHs revealed that they had viscoelastic properties between the unreinforced controls and the chemically treated CSHs (2.94 at 8 Days: $p<0.0005$ vs. Control, $p<0.0002$ vs. Glut CSH; 2.74 at 23 Days: $p<0.0001$ vs. Control, $p<0.0002$ vs. Glut CSH).

As in the creep analysis, the stress-strain data from the stress relaxation experiments could be expressed using mathematical descriptions such as the Burger's viscoelastic model. The four elastic parameters and coefficients of viscosity for the stepwise stress relaxation tests mirrored the trends seen in the creep investigations. After eight and twenty-three days of culturing, $R_1$ parameters rose 6.7-fold ($p<0.03$) and 13.1-fold ($p<0.0001$) when unreinforced constructs were combined with uncrosslinked support sleeves. When the sleeves were crosslinked, these parameters exhibited an additional increases (Day 8: 24.0-fold, p<0.0001 vs. Control; 3.6-fold, p<0.005 vs. UnXL CSH; Day 23: 65.5-fold, p<0.0001 vs. Control; 5.0-fold, p<0.005 vs. UnXL CSH). Similarly, $R_2$ and $\eta_2$ parameters rose when control constructs were combined with uncrosslinked CSH ($R_2$: 8 Days⇒12.4-fold increase, p<0.02; 23 Days⇒19.9-fold increase, p<0.0003; $\eta_2$: 8 Days⇒10.9-fold increase, p<0.004; 23 Days⇒21.2-fold increase, p<0.0001). The same was true with glutaraldehyde treated CSHs ($R_2$: 8 Days⇒193-fold increase, p<0.0001 vs. Control; 15.6-fold increase, p<0.0003 vs. UnXL CSH; 23 Days⇒743-fold increase, p<0.0001 vs. Control; 37.3-fold increase, p<0.0001 vs. UnXL CSH; $\eta_2$: 8 Days⇒1080-fold increase, p<0.0001 vs. Control; 98.5-fold increase, p<0.0001 vs. UnXL CSH; 23 Days⇒1880-fold increase, p<0.0001 vs. Control; 88.5-fold increase, p<0.000 1 vs. UnXL CSH). When the long-term relaxation parameter $\eta_1$ was investigated, uncrosslinked CSHs increased 31.5-fold (p<0.004) and 49.6-fold (p<0.0001) versus unreinforced controls at days eight and twenty-three, respectively. Crosslinking induced an additional increase of the $\eta_1$ coefficient (8 Days: 3,920-fold, p<0.0001 vs. Control; 124-fold, p<0.0001 vs. UnXL CSH; 23 Days: 3,880-fold, p<0.0001 vs. Control; 78.2-fold, p<0.0001 vs. UnXL CSH). As in the creep experiments, time of culture did not play a significant role in affecting the Burger's model parameters.

Burst Pressure Data

Immediately following the construction of acellular sleeves, burst analysis revealed that the supports all exhibited relatively high peak pressures. Glutaraldehyde treatment manifested in a 40% additional increase in burst strength (Glut⇒877 mmHg vs. UnXL⇒623 mmHg, p<0.0001). When the UnXL acellular supports were incubated in tissue culture media at 37° C. for eight days, the peak pressures of the sleeves dropped to 163 mmHg, or 26% of their original values (p<0.0001). The deterioration of acellular sleeves treated with glutaraldehyde was not nearly as drastic—peak pressures measured at 787 mmHg (90% of Day 0 values, p<0.35) after eight days of culture.

After eight days of culture, uncrosslinked support sleeves that were combined with cell-seeded layers to form CSHs demonstrated burst strengths that were significantly higher than in the unsupported control constructs (p<0.001) as expected, but the peak pressure dropped even further. Falling to 99 mmHg, the UnXL CSHs were only 60% as strong as UnXL acellular supports which had been cultured for eight days (p<0.02) and only 16% as strong as UnXL acellular supports that had not been exposed to culture media for eight days (p<0.0001).

Again, the loss of strength with time was less pronounced if glutaraldehyde crosslinking was employed. The decrease of peak pressure in Glut CSHs cultured for eight days (649 mmHg) did not reach statistical significance compared to XL acellular supports cultured for the same duration (<0.29) or XL acellular support sleeves that had not been exposed to culture media (<0.06). The changes of the burst pressures ofacellular sleeves with time indicated the presence of non specific, acellular modes of degradation. The relation of the strengths of acellular sleeves and of CSHs after eight days indicated the presence of cell-mediated modes of degradation as well.

Fibrin-Based Constructs

Fibrin was investigated as a collagen substitute in the vascular grafts ECM in an attempt to improve the mechanical strengths and elasticity of the constructs. TE constructs fabricated from fibrin and fibrin-collagen mixes were analyzed using gel compaction measurements, histological staining, and mechanical testing. The results described in this section correspond to experiments conducted on tubular constructs seeded with RASMs fabricated from human fibrinogen and/or Type I rat collagen. All constructs were cultured statically in an unconstrained fashion on silicon sleeves for six days prior to analysis.

In conducting the analysis on the fibrin-based construct experiments, it was noticed that the batch-to-batch variability between different sample preparations resulted in a statistically significant impact on many of the observations investigated. Since many of the changes between the treatments used were subtle, a two-way ANOVA with blocking was used to evaluate the data to avoid missing statistically relevant changes which might have otherwise been masked.

Gel Compaction Data

During the initial forty-eight hours following their fabrication, collagen-based, fibrin-based, and collagen/fibrin constructs all compacted rapidly. Although the ends of some samples exhibited slight irregularities, the three construct types compacted uniformly across the mandrel. Constructs containing fibrin exhibited increased compaction compared to their collagen-based counterparts. After six days of culture, fibrin constructs occupied only 52% of the volume of the collagen constructs (Fibrin⇒6.8% vs. Collagen⇒13.1%, p<0.0001). Gel compaction of the fibrin/collagen mixes were statistically dissimilar from either the pure fibrin or pure collagen constructs (Mix⇒9.7% vs. Collagen⇒13.1%, p<0.0003; Mix⇒9.7% vs. Fibrin⇒6.8%, p<0.002).

The differences in matrix remodeling had a greater impact on wall thickness than on the lengths of the constructs. The changes in wall thicknesses mirrored the overall compaction trends, with the fibrin constructs and the fibrin/collagen mixes reducing to 50% and 71% of the thickness of collagen constructs, respectively (Fibrin⇒0.523 mm vs. Collagen⇒1.05 mm, p<0.0001; Mix⇒0.75 mm vs. Collagen, p<0.0002; Mix vs. Fibrin, p<0.002). After the culturing period, the collagen and fibrin/collagen mixes were lightly adhered to the silicon on the mandrel. While the bonding provided enough resiliency for dynamic conditioning and other mechanical manipulations, it did not present difficulty when removing the constructs from the mandrels. Fibrin constructs, on the other hand, formed tight adhesions with the silicon and were difficult to detach without damaging the samples.

Histology

Some histological H&E staining of collagen and fibrin-based vascular grafts was performed by Christopher Cummings. The matrix of constructs fabricated from reconstituted collagen appeared markedly different than the matrix of constructs fabricated from fibrin. While the matrix in collagen-based resembled that of similar constructs described previously, the fibrin-based constructs consisted of thicker fibers which were organized into "spiderweb" shaped structures. Large voids could be seen between the fibers of the fibrin gels. The fibrin/collagen mixes possessed properties of both the collagen and fibrin-based constructs. Although the samples discussed in this section were constructed using bovine Type I collagen (ICN) instead of rat tail collagen, the fabrication processes and culturing conditions were equivalent to the other fibrin-based experiments.

Uniaxial Tensile Test Data

Fibrin-based constructs possessed different characteristic stress-strain profiles than the collagen-based constructs and fibrin/collagen mixes. They exhibited larger degrees of strain prior to imparting resistance to mechanical deformation. Following this extended "toe-region", the fibrin constructs demonstrated essentially linear stress-strain behavior ($R^2 \Rightarrow 0.99$) up to the point of failure with little to no yielding phenomena.

Fibrin-based constructs exhibited a 3.5-fold increase in ultimate stress compared to collagen-based constructs (Fibrin$\Rightarrow$18.5 kPa vs. Collagen$\Rightarrow$5.3 kPa, $p<0.0008$) and a 1.4-fold increase compared to fibrin/collagen mixes (Fibrin vs. Mix$\Rightarrow$12.9 kPa, $p<0.13$). A comparison between the collagen-based and fibrin/collagen mixed constructs revealed a 2.4-fold increase in tensile strength when fibrin was incorporated (Mix vs. Collagen, $p<0.04$).

While the use of fibrin had substantial impact on the ultimate stresses of the various constructs, the resulting linear moduli were relatively unaffected. The linear moduli of the fibrin-based, collagen-based, and fibrin/collagen mixed constructs were statistically identical with mean values of 18.6 kPa, 21.0 kPa, and 21.5 kPa respectively (Fibrin vs. Collagen, $p<0.85$; Fibrin vs. Mix, $p<0.78$; Mix vs. Collagen, $p<0.995$).

The work required for the tensile testing was obtained by integrating the area under the stress-strain curves. Observed mean yield energies were 3.6-fold larger for fibrin-based constructs than collagen-based constructs (Fibrin$\Rightarrow$0.063 mJ/mm vs. Collagen$\Rightarrow$0.18 mJ/mm, $p<0.015$) and 2.8-fold larger for fibrin/collagen mixes than collagen-based constructs (Mix$\Rightarrow$0.049 mJ/mm vs. Collagen, $p<0.083$). Observed mean failure energies were 1.26-fold larger for fibrin-based constructs than collagen-based constructs (Fibrin$\Rightarrow$0.066 mJ/mm vs. Collagen$\Rightarrow$0.052 mJ/mm, $p<0.57$) and 1.41-fold larger for fibrin/collagen mixes than collagen-based constructs (Mix$\Rightarrow$0.074 mJ/mm vs. Collagen, $p<0.27$).

The ratios of the energy parameters revealed that the matrix compositions of the constructs affected their failure behaviors. Collagen-based constructs possessed high yield to failure energy ratios compared to fibrin-based (3.0-fold increase, $p<0.0001$) and mixed constructs (2.2-fold higher, $p<0.0003$). Mixed constructs possessed higher ratios than fibrin-based constructs on average but were not significantly different statistically (1.4-fold higher, $p<0.42$). As in the glutaraldehyde treated CSHs described previously, the fibrin-based constructs exhibited negligible plastic deformation as evidenced by their essentially equivalent yield and failure energy parameters.

Creep Viscoelastic Analysis

As in the previous systems studied, mechanical characterization of the fibrin-based constructs was not limited to uniaxial tensile testing. Creep analysis was performed to obtain initial data describing changes in viscoelastic behaviors with alternative extracellular matrix materials. In general, the increased strengths of constructs fabricated exclusively from fibrin and from fibrin-collagen mixes translated into decreased strain deformations under the loads in the creep analysis.

The stress-strain data of the three construct types were modeled using Burger's four parameter mechanical analog. The fits were typically very accurate with average parameters of 0.958, 0.964, and 0.970 for the fibrin-based, collagen-based, and fibrin/collagen mixed constructs, respectively. Average parameters of elasticity and coefficients of viscosity exhibited somewhat sizable deviations due in part to the batch to batch variability that was observed. As described previously, a two-way ANOVA with blocking was employed to isolate the effects of ECM components.

The elasticity parameter $R_1$ defined by the instantaneous strain jump at the onset of the creep experiment was highest in the collagen-fibrin mix (1.4-fold increase, $p<0.14$ vs. Fibrin; 1.7-fold increase, $p<0.03$ vs. Collagen). Similar to the extended "toe regions" seen in the uniaxial tensile data, the fibrin-based constructs demonstrated large degrees of deformation as the loads were introduced. This manifested in reduced $R_1$ elasticity parameters which were statistically equivalent to collagen-based constructs.

The elasticity modulus $R_2$ and coefficient of viscosity $\eta_2$ which defined the transient region of the creep strain profile were highest in fibrin-based constructs ($R_2$: 3.9-fold increase, $p<0.0001$ vs. Collagen; 2.8-fold increase, $p<0.002$ vs. Mix; $\eta_2$: 2.9-fold increase, $p<0.02$ vs. Collagen; 2.5-fold increase, $p<0.05$ vs. Mix). This agreed with the shortened time scales needed for the fibrin-based constructs to rapidly relax to their "steady-state" creep domain. Both the $R_2$ and $\eta_2$ parameters were statistically indistinguishable between the collagen-based and mixed matrix constructs.

The coefficient of viscosity $\eta_1$, the parameter responsible for long-term, or "steady state", creep behavior, was also slightly higher in fibrin-based samples than in the other materials (4.8-fold increase, $p<0.0006$ vs. Collagen; 2.5-fold increase, $p<0.006$ vs. Mix). This was seen in the decreased rates of deformation that occurred at times long after the introduction of the creep load. Constructs containing a 50-50 mix of collagen and fibrin did not possess higher $\eta_1$ coefficients of viscosity compared to collagen-based samples ($p<0.44$) indicating that combinations of ECM components did not affect the resultant gels as much as pure fibrin compositions.

Example 10

Mechanical Testing Methods

Ring Testing Apparatus

The mechanical properties of the cell-seeded tubular constructs were resolved using a ring testing apparatus. The instrument was designed to operate in the low force loading ranges which are characteristic of the collagen-based constructs. The ring testing apparatus consisted of five major elements: the structural framework and test chamber, a force transducer load cell, a servo motor position controller, an image acquisition system, and a data acquisition system. The steel framework structure stabilized the set-up and ensured a stationary test environment. A circular test chamber was fitted with watertight observation windows in both the front and back to provide a means of capturing sample images during testing. Samples were loaded into the chamber through a 1.5" diameter entrance port at the top of the chamber. The lower hook was connected to a DCI-CP3-50-01 Mini™ linear position table (DCI Design Components, Inc., Fayetteville, Ga.) via a brass shaft which ran through an o-ring orifice in the bottom of the test chamber. The linear position table had a five inch lead screw travel range and a 30 pound payload capacity which provided 0.1 inches of travel per revolution and was rated with a position accuracy of ±0.0005 inches. Limit sensors located at the boundaries of the position table prevented damage from accidental overextension.

The upper hook in the test chamber was threaded into a GS0 series precision load cell (Transducer Techniques, Temecula, Calif.) with either a 30 or 150 gram loading range. The signal from the load cell transducer was transmitted through an amplifier signal conditioner and tuned to a 0–5 volt DC analog signal output. The signal output was directed to both a Pentium PC computer through a PCI-1200 acquisition board and the servo motor position controller. The load cell transducer was calibrated manually at the start of each series of mechanical tests using a set of weights that spanned the range of the transducer.

The integrated brushless DC servo motor (SmartMotor™ Model SM-2320, Animatics Corp., Santa Clara, Calif.) was used to drive the position table's lead screw. The motor tracked the amplified DC signal readings from the load cell using an analog input command function while communicating signal outputs to the PC computer through an RS-232 port. Term™ terminal emulation software (Animatics Corp.) was utilized to generate and transmit commands to the memory module of the servo motor.

Black and white digital images of the samples were captured during the mechanical tests using a V-1056SX 1/3" CCD camera (Marshall Electronics Inc., El Segundo, Calif.) connected to a Matox Meteor acquisition board (Matrox Electronic Systems Ltd., Montreal, Canada). Depending on the testing method used, the images were collected as 640×480 pixel pictures in either a TIF file format or as a compilation of images in an AVI file format using Inspector™ 3.0 software (Matrox Electronic Systems Ltd.). Compression of the AVI files was performed using a Microsoft file compression protocol to keep the size of the documents manageable.

Force and position data were collected at 180 samples/sec through the PCI-1200 acquisition board using LabView™ software (National Instruments, Austin, Tex.). The 12-bit acquisition board contained 8 analog inputs, 2 analog outputs, 24 digital input/output lines, and 3 counters/timers. Signal buffering of the load cell force data was performed digitally with a low-pass Butterworth filter using a 120 Hz sampling frequency and a 20 Hz cutoff frequency. Synchronized readings of both signals were compiled into an Excel™ file format for subsequent data analysis.

Sample Preparation

Tubular tissue constructs were removed from the culturing media and washed in PBS under gentle agitation. The constructs were than imaged via a color NTSC CCD camera connected to the Matrox Meteor image acquisition board to obtain dimensional information including degree of compaction and wall thickness. The rubber stoppers were removed from the glass mandrel and the constructs were loaded onto a ring slicing apparatus. Using a razor blade, the constructs were sliced into ~5 mm sections. Four small black beads were affixed with a cyanoacrylate-based adhesive to one of the cut ends of each ring sample to provide local wall strain information.

A digital caliper was used to determine the widths of each sample ring while wall thicknesses of each construct were calculated from analysis of digital images using Inspector™ 3.0 software. Specimens were handled using surgical manipulators and care was taken in all steps to minimize incidental damage. Samples were stored in PBS at room temperature until ready to be tested.

Uniaxial Tensile Test

Uniaxial tensile tests were used to characterize the overall strengths of the TE vascular constructs. By stretching ring samples to failure at a constant strain rate, it was possible to educe circumferential tensile properties of the tubular constructs. This section describes the testing procedures, the processes used to convert the data into stress-strain relationships, and the methods employed to determine the reported mechanical parameters.

Using the Term™ command generator, the hooks were positioned adjacent to one another so that it was possible to thread them through the lumen of the ring specimens with surgical manipulators. The lower hook was then dropped downward until the hooks were approximately 2.5 mm apart from one another. Prior to testing, each specimen was preconditioned to remove stress history using the Preconditioning.sm command program and the servo motor memory module. Preconditioning.sm provided the appropriate directives to stretch each sample through three cyclic 0.2 mm/sec loading sequences to approximately 20% of the strain at rupture. Force-displacement data were collected using the SampleFilter LabView™ file while images were captured into an AVI file (4 frames/sec) via Inspector™ 3.0.

Following the removal of the stress history, the samples were stretched uniaxially to failure at a constant 0.2 mm/sec using the Stretch.sm preprogrammed command file. Sample images and force-displacement data were collected as described in the preconditioning loading stage until sample failure had occurred. Following the completion of each test run, the lower hook was returned to its original location for subsequent mechanical tests.

Force-displacement readings were converted into stress-strain data to assess the material properties of the tissue. Using the tab-delineated option, the data was opened into an Excel™ spreadsheet and converted from voltage readings to the appropriate units. The force-voltage relationship determined during the load cell calibration and the sample dimensions were inserted into the appropriate spaces of the spreadsheet to calculate Cauchy, or engineering stresses. Since it was not possible to reliably assess accurate cross-sectional areas throughout the duration of the test, the stresses were normalized according to the pre-testing sample dimensions. Cauchy stresses were determined as follows:

$$\sigma\{t\} = \frac{F\{t\}}{A_o} = \frac{F\{t\}}{2TW} \qquad \text{Equation 3.1.}$$

where $\sigma\{t\}$ is the stress as a function of time, $F\{t\}$ is the force as a function of time, $A_o$ is the original cross-sectional area, T is the wall thickness, and W is the width of each ring sample. Since both construct walls are assessed at the same time in the ring specimen testing format, the dimensions are multiplied by a factor of two to obtain the cross-sectional area.

Strain-displacement relationships for the ring samples were established from the collected AVI files and the Inspector™ image analysis package. Using the BlobAnalysis function and the HookFinder script, bead and hook positions were determined at each frame from the onset of tensile deformation to just prior to the visual onset of failure. This set of data was transferred to an Excel™ spreadsheet, converted to millimeters using a Creep_Video_Data macro, and plotted to determine a linear mathematical relationship between the hooks and the beads on the left and right walls. The voltage displacement information in the original spreadsheet was converted to Eularian strain data using the hook-bead relationships and the following equation:

$$\varepsilon\{t\} = \frac{L\{t\} - L_o}{L_o} \qquad \text{Equation 3.2.}$$

where $\varepsilon\{t\}$ is the strain as a function of time, $L\{t\}$ is the distance between the hooks/beads as a function of time, and $L_o$ is the original distance between the hooks/beads. A distance of 4.01 mm was typically used for the hooks of the standard tubular constructs to standardize the strain measurements. The value corresponded to unstrained sample dimensions plus a 20% offset. The offset was necessary because of plastic deformations introduced during the preconditioning runs.

The mechanical data were plotted to obtain stress-strain relationships for each uniaxialy tested ring sample. Peak, or ultimate, stress ($\sigma_{max}$ or UTS) was identified as the maximum stress data values for each sample. The linear modulus was calculated from the best fit slopes of the linear segments of the stress-strain profiles. To standardize the moduli parameters, the linear segments were defined as the regions spanning 25–75% of the $\sigma_{max}$ in each sample. The amount of energy required to deform each sample was also calculated as an estimate of construct toughness. The yield energy was calculated by integrating the areas under the force-displacement curves from the point of zero strain to the point where sample yielding was visually observed. The failure energy was calculated by integrating the areas from the point of zero strain to the point where the stress on the sample had dropped to 50% of $\sigma_{max}$. Both yield and failure energies were normalized by the unstressed widths of each sample ring.

Step-Stress Relaxation

Stepwise stress relaxation was utilized as a static viscoelastic test method to assess the cell-seeded tubular constructs. By instantaneously stretching ring samples to set displacements and measuring the subsequent stress response as a function of time, it was possible to examine some of the viscoelastic mechanical behavior.

Ring samples were prepared as previously described and loaded onto the hooks of the mechanical testing apparatus. Specimens were preloaded with the servo motor using the StressRelax.sm command file. During the first two minutes following the preload, force data was collected through the SampleFilter Labview™ file as described in the uniaxial tensile testing section. Manual recordings from a volt meter were taken every fifteen seconds during the subsequent four minutes. At the end of the sixth minute, a step displacement was introduced to the specimens using the Relax.sm servo motor command file. Force data was again acquisitioned through Labview™ for 120 seconds followed by four minutes of manual recordings. Incremental step displacements were implemented at the $6^{th}$, $12^{th}$, $18^{th}$, $24^{th}$, and $30^{th}$ minutes. TIF file images were collected using Inspector™ after the preload and following every ensuing displacement.

Hook displacements and bead locations were calculated directly from the TIF file images using Inspector™'s BlobAnalysis function. This information was then converted into Eularian strain data using Equation 3.2. The preload force data was opened into an Excel™ spreadsheet using the tab-delineated format option. The columns were shifted to the right and time values were inserted using the appropriate sampling rate such that time zero coincided with the occurrence of the peak force reading. Manually recorded time and force data points were also entered into the spreadsheet. The voltage force readings were converted to stress values using the pretest sample dimensions and the load cell force-voltage calibration relationship. This procedure was repeated on the force files for the remaining step displacements, and the data was compiled into a single spreadsheet to form a complete data set for each sample.

As the sample stresses were plotted as a function of time, mechanical parameters including initial moduli, relaxed moduli, and relaxation periods were evaluated from the data. Initial moduli were determined by best fit linear curves of the sample stresses immediately following each displacement increment versus the corresponding hook strain at each point. Similarly, relaxed moduli were determined by best fit linear representations of the sample stresses six minutes after each step displacement versus the corresponding hook strain at each point. The relaxation periods were defined as the amount of time necessary for the loads in each sample to decay one half of the stress jumps associated with each step displacement increment. Stress relaxation profiles were also fit to linear mechanical models.

Creep Tests

Static viscoelastic creep investigations were used to complement the stepwise stress relaxation analysis. Creep is the time-dependent change in strain following the introduction of a step alteration in stress.

Once again, ring samples were prepared as previously described and loaded onto the hooks of the mechanical testing apparatus. Cross-sectional dimensions and calculated peak stress values from uniaxial tensile testing were employed to determine a target stress force values. Unless otherwise indicated, target values were aimed at one third of the sample's peak stress ($\sigma_{target} \approx \frac{1}{3} \sigma_{max}$) These forces were converted to voltages using the load cell's calibration profile and programmed into the Creep.sm servo motor file.

Following execution of the Preconditioning.sm preloading regimes, the creep test procedures were implemented. Servo motor moved the lower hook downward at 1.6 mm/sec until the target forces were realized. The hook velocities were then adjusted to 0.02 to 0.1 mm/sec downward (depending upon the sample properties) if the force readings were lower than the target force or 0.0 to 0.005 mm/sec upward if the force readings exceeded the target force. Thus it was possible to approximate a relatively constant force throughout the duration of the experiment. Specific fine tuning velocities were determined empirically for each sample type prior to testing. Force-displacement data were collected for the initial two minutes of each test using the SampleFilter LabView™ file as described previously. For the first four minutes of each creep test, series of images were captured into AVI files at 4 frames/sec using Inspector™ 3.0 software. Subsequent images were collected at 0.2 frames/sec for the following sixteen minutes of testing. Tests were halted at the point of sample failure or after twenty minutes of creep.

Strain displacement analysis was preformed on the AVI files using image analysis software. As previously described, the BlobAnalysis function and the HookFinder script were utilized to determine the locations of the hooks and beads at each point throughout the tests. The data was transferred to an Excel™ spreadsheet, converted to millimeters using the Creep_Video_Data macro, and transformed into a time-dependent strain relationship. As previously described, a 4.01 mm distance was typically used for the hooks of the standard tubular constructs to standardize the strain measurements. Average force loads for each sample were determined from the SampleFilter force-displacement files and converted into Cauchy stresses using the unstressed sample dimensions. Creep profiles were fit to linear mathematical models as later described to determine appropriate mechanical parameters.

Example 11

Mechanical Testing of Acellular Sleeves

These samples require slow testing rates to accurately elucidate their stress-strain relationships. A commercial mechanical test apparatus (DDL, Inc., Eden Prairie, Minn.) was utilized to test the acellular support sleeves.

DDL Mechanical Testing Apparatus

A 650R DDL electromechanical testing system was utilized to perform tensile tests on acellular sleeve supports. The test system was outfitted with a SM-200N load cell which was calibrated to 25 pounds according to the manufacture's protocol and connected to a pneumatic-driven upper grip through a universal connector. An environmental chamber designed to hold the samples in a saline during the mechanical testing was used in lieu of the lower grip. MtestWr software (DDL Inc.) was used to interface between the DDL apparatus and a Pentium PC.

Sample Preparation

Sleeves were briefly incubated in saline and cut along the long axis to remove them from the capillary tubes. This yielded relatively flat sheets approximately 38 mm in length and 9.5 mm in width. These sheets were further cut into test samples (~6 mm×9.5 mm) along either the circumferential or longitudinal orientation. The extreme edges of the sleeves were discarded because of physical defects introduced during the drying on the capillary tubes. Disposable plastic grips (~7 mm×20 mm) were folded in half and affixed to each end of the test samples with a small amount of a cyanoacrylate-based adhesive such that 2 mm of each sleeve were held within the plastic grips. The precise dimensions of the test samples were measured using a digital caliper. Test samples were loaded into the environmental chamber of the test apparatus and the pneumatic actuator clamp was tightened about the plastic grip and inflated to a pressure of 60 psig. The environmental chamber was filled with PBS and samples were incubated in saline for approximately ten minutes prior to testing.

Uniaxial Tensile Tests

Uniaxial tensile tests were used to gauge the strengths of the acellular support sleeves in both the circumferential and longitudinal orientations. Once the samples had been loaded into the testing chamber and allowed to equilibrate, three preconditioning cycles were performed to remove residual stress history and to eliminate slack introduced during the loading process. Samples were then stretched to failure at a constant rate of 3 mm/min while force-displacement data were collected at 60 samples/sec. The mechanical data were plotted to obtain stress-strain relationships for each sample tested. As in the cell-seeded constructs, ultimate stresses ($\sigma_{max}$) were identified as the maximum stress data values for each sample. Linear moduli were calculated as the best fit slopes of the linear segments (spanning 25–75% of the $\sigma_{max}$) of the stress-strain profiles.

Burst Pressure Testing

The mechanical performance of some of the tubular constructs and acellular support sleeves were characterized through burst pressure assessment. In these tests, entire constructs were ligated into a burst pressure chamber, and inflated at a constant flow rate until the point of rupture. This section describes the testing procedure and the analysis methods used in the burst pressure tests.

Following the specified culturing periods, constructs were removed from their growth media and washed in room temperature PBS under gentle agitation. After imaging each sample with a CCD camera, the extreme ends were removed with a razor blade. Samples were loaded into the burst chamber and sutured to the lure pegs which protruded in from the walls. The chamber was filled with PBS and sealed. Before each test, air was flushed from the system by running saline through the lumen of each construe.

A syringe pump was used to infuse PBS into the sample at a constant flow rate of 4.0 ml/min while a Millar Mikro-tip catheter-type pressure transducer recorded local pressure changes near the lumens of the constructs. The pressure transducer was connected to a 10× amplifier signal conditioner which interfaced to a computer through a PCI-1200 acquisition board using LabView™ software. As previously described, digital video images were recorded into AVI series formats every 4 seconds throughout the tests to allow for pressure-diameter relationship calculations. The tests proceeded until the samples burst as evidenced by a rapid drop in the pressure readings.

The data obtained from the burst pressure tests were analyzed in Excel™. A pressure-voltage relationship determined for the Millar pressure transducer over a 0 to 10 psig interval was used to convert the data to the appropriate units. The maximum pressure attained in each test was determined and defined as the peak, or burst pressure for the sample. The Inspector™ software line Measurement function was used to assess the outer diameters of the constructs throughout the tests. These measurements were converted to millimeters using the information from the preburst sample images. These measurements were inputted into the pressure data spreadsheet to obtain pressure-diameter correlations. Stiffness parameters were estimated using the data spanning regions ranging from 25 to 75% of the peak pressure.

Mechanical Models

Creep and stress relaxation data were fit to either the standard viscoelastic solid (SVES) three element model or Burger's four element mechanical model to determine appropriate mechanical parameters. The following sections explicate the stress-strain relationships for the creep and stress relaxation tests as defined by the SVES and Burger's linear viscoelastic models. The methods used to solve these mathematical relationships are also described.

Standard Viscoelastic Solid (SVES)

The constitutive equation for the SVES is a follows:

$$\sigma\{t\} + \frac{\eta}{R_1 + R_2}\dot{\sigma}\{t\} = \frac{R_1 R_2}{R_1 + R_2}\varepsilon\{t\} + \frac{R_1\eta}{R_1 + R_2}\dot{\varepsilon}\{t\} \qquad \text{Equation 3.3.}$$

where $\sigma\{t\}$ and $\epsilon\{t\}$ are respectively the stress and strain as functions of time, $R_1$ and $R_2$ are elastic parameters, and $\eta$ is the coefficient of viscosity. In creep testing, samples are exposed to a step increase in stress at time zero. At times greater than zero, the stress is held constant, ($\sigma\{t\}=\sigma_o$). When inputted into Equation 3.3, the strain as a function of time can be expressed as:

$$\varepsilon\{t\} = \sigma_o R_1 + \frac{R_2}{R_1 R_2} - \frac{\sigma_o}{R_2}\exp\left(\frac{-R_2 t}{\eta}\right) \qquad \text{Equation 3.4.}$$

In the stress relaxation tests, samples were exposed to step changes in strain ($\epsilon_o$). When inputted into Equation 3.3, the stress relationship as a function of time can be expressed as:

$$\sigma\{t\} = \varepsilon_o R_1 \left[ \frac{R_2}{\eta} + \left(1 - \frac{R_2}{\eta}\right) \exp\left(\frac{-\eta}{R_1 + R_2}\right) \right] \quad \text{Equation 3.5.}$$

This model allows for instantaneous changes in both stress and strain which are followed by decaying transition periods. The SVES is considered a viscoelastic solid because the materials will continue to support a stress without deformation after all the transients have died away.

Burger's Viscoelastic Model

The constitutive equation for Burger's model is as follows:

$$\sigma\{t\} + \left(\frac{\eta_1}{R_1} + \frac{\eta_1}{R_2} + \frac{\eta_2}{R_2}\right)\dot{\sigma}\{t\} + \frac{\eta_1\eta_2}{R_1 R_2}\ddot{\sigma}\{t\} = \eta_1\dot{\varepsilon}\{t\} + \frac{\eta_1\eta_2}{R_2}\ddot{\varepsilon}\{t\} \quad \text{Equation 3.6.}$$

where $\sigma\{t\}$ and $\varepsilon\{t\}$ are respectively the stress and strain as a function of time, $R_1$ and $\eta_1$ are the elastic parameter and coefficient of viscosity for the Maxwell unit, and $R_2$ and $\eta_2$ are the elastic parameter and coefficient of viscosity for the Kelvin unit. In the analytical solution for creep where samples are exposed to a constant stress ($\sigma_o$) the strain functions of Equation 3.6 can be expressed as:

$$\varepsilon(t) = \frac{\sigma_o}{R_1} + \frac{\sigma_o}{\eta_1} t + \frac{\sigma_o}{R_2}\left[1 - \exp\left(\frac{-R_2 t}{\eta_2}\right)\right] \quad \text{Equation 3.7.}$$

In the analytical solution for stress relaxation tests where samples were exposed to step changes in strain ($\varepsilon_o$) stress in Equation 3.6 as a function of time can be expressed as:

$$\sigma\{t\} = \varepsilon_o/A \, [(K_1 - K_2 L_2)\exp(-L_1 t) - (K_1 - K_2 L_2)\exp(-L_2 t)] \quad \text{Equation 3.8.}$$

where:

$$L_1 = \frac{(J_1 - A)}{2J_2} \qquad J_1 = \frac{\eta_1}{R_1} + \frac{\eta_1}{R_2} + \frac{\eta_2}{R_2}$$

$$L_2 = \frac{(J_1 + A)}{2J_2} \qquad J_2 = \frac{\eta_1 \eta_2}{R_1 R_2}$$

$$A = \sqrt{J_1^2 - 4J_2} \qquad K_1 = \eta_1$$

$$K_2 = \frac{\eta_1 \eta_2}{R_2}$$

Like the SVES, Burger's model is capable of instantaneous stress-strain changes which are followed by transition periods. Unlike the SVES, Burger's model describes a viscoelastic fluid because stress relaxation loads will eventually decay to zero and sample will continue to deform indefinitely under applied stress loads.

Mathematical Solutions

Hook data from viscoelastic tests were fitted to mechanical models using Excel's Solver Add-In package. Best fit values for each parameter were determined by minimizing the sums of the square of the errors between the proposed models and the experimental data sets. Nonlinear Newtonian searches were conducted using quadratic estimates and central derivatives. Precision and convergence criteria were set at $1\times10^{-10}$ to ensure that the application ran until a high-quality fit was obtained. Initial parameter guesses were selected to minimize erroneous root solutions, and the fits were run until acceptable solutions were obtained. Hook (overall) strain measurements were selected in favor of wall (local) strains due to the anomalous behaviors that frequently accompanied the beads. Mechanical parameters were calculated for each sample and grouped together to perform statistical inferences on the samples.

Example 12

Characterization of Cell and Construct Functionality

In addition to appropriate mechanical behaviors, there are many other requirements that will affect the success of tissue engineered vascular grafts. Knowledge of cell proliferation, viability, and matrix expression can help to ascertain the effects of various factors on cellular function. Similarly, information pertaining to ECM structure reorganization and gel compaction will help to link cellular function and culturing conditions back to construct functionality and mechanical behavior.

Construct Imaging and Dimensional Analysis

Digital images of constructs were acquired at the end of each culturing period to observe macroscopic appearances and to perform dimensional analysis. A color NTSC CCD camera outfitted with a c-mount lens was used to capture images onto a PC computer through a digital acquisition board. Files were saved into a TIFF file format and analyzed using Inspector 3.0 software. Construct lengths and widths were determined in terms of pixels through three independent measurements of each parameter. Pixels were then converted to standard units using a metric ruler that was imaged simultaneously with each construct. The volume of each construct (V) was computed using the following equation:

$$V = \left(\frac{\pi}{4}\right) \times (D_0^2 - D_i^2) \times L \quad \text{Equation 3.9.}$$

where $D_0$ was the outer diameter of the construct, $D_i$ was the inner diameter of the construct, and L was the construct length. $D_o$ and L were determined from the average of the parameter calculations while $D_i$ was assumed equal to the widths of the glass mandrel capillary tubes (or the silicone support sleeves in the case of the fibrin matrix studies).

Degree of construct compaction, reported as a percentage of original volume, was calculated using the following relationship:

$$\text{Compaction} = (V/V_o) \times 100\% \quad \text{Equation 3.10.}$$

where $V_o$ corresponded to the original volume of the construct and was calculated using the following equation:

$$V_o = \left(\frac{\pi}{4}\right) \times (11.5^2 - D_i^2) \times L_o \quad \text{Equation 3.11.}$$

$L_o$ corresponded to the original length of the constructs and was determined using the average of three independent measurements of the distances between the rubber stoppers on the mandrel. The initial outer diameters of the constructs were assumed equivalent to the inner diameters of the test tube molds (11.5 mm). Once again, $D_i$ was assumed equal to the widths of the glass mandrel capillary tubes. Average wall thickness of each construct was calculated as follows:

$$T_{ave} = (D_o - D_i)/2 \quad \text{Equation 3.12.}$$

Cell Viability Assays

Live-dead examinations were performed using a calcein-AM/ethidium homodimer-1 stain (Molecular Probes, Eugene, Oreg.) to establish cell viability and distribution throughout the constructs. Samples were rinsed 3×10 minutes in buffered saline and incubated at room temperature in a calcein-ethidium (4 µM-4 µM, respectively) saline solution for 45 min. Following three subsequent 10 min washes to remove excess staining solution, the samples were imaged on a Zeiss LSM 510 confocal microscope (Carl Zeiss, Inc., Thornwood, N.Y.). As the calcein-AM crossed the cellular membranes, the molecule was cleaved by esterase activity within viable cells to elicit cytoplasmic green fluorescence. Ethidium homodimer-1, a membrane impermeant dye, labeled the nucleic acids of dead/membrane-compromised cells with red fluorescence. Cell viability was estimated roughly as a function of distance into both the construct and the sleeve support layers.

DNA Assays

Estimations of the total number of cells within constructs were made using a Hoechst DNA binding dye. Cultured constructs were washed 3×10 minutes in PBS (pH 7.4) and stored frozen (−20° C.) until ready to be analyzed. Construct samples were then digested in a 0.5 mg/ml proteinase K solution (50 mM Tris, 0.1 M EDTA, 0.2 M NaCl, pH 7.4, ~1 ml/M cells) containing 0.1 mg/ml sodium dodecyl sulfate (SDS) at 55° C. for 12 hours (Kim and Mooney 1998). The samples were passed through a 25-gauge syringe needle three times, inspected visually to ensure complete digestion, and centrifuged for 2 min at 2000 rpm (320 g) to remove large debris. Samples were then loaded in duplicate (10 µl/well) into a 96-well black plate (VWR, Suwanee, Ga.) at 1-fold, 4-fold, and 8-fold dilutions and combined with a 0.1 µg/ml Hoechst-33258 dye solution (10 mM Tris, 1 mM EDTA $Na_2.2H_2O$, 0.2 M NaCl, pH 7.4, 200 µl/well). Following a 10–15 min incubation in the dark at room temperature, samples were read on a Spectra Max Gemini plate reader (Molecular Devices, Sunnyvale, Calif.) at 25° C. using a 365 nm excitation wavelength and a 458 nm emission wavelength. Standards created from calf-thymus DNA and known cell populations analyzed using the Coulter Multisizer were run in parallel to estimate the number of cell in each construct.

Endothelial Cell Seeding

Tubular constructs and acellular support sleeves were cut along the long axes and opened up such that their inner lumens were exposed. They were then embedded in a 3.5% agar gel in this configuration to provide a flat lumenal surface. Passage 4/5 human coronary endothelial cells (HCEC, Clonetics) were trypsinized and seeded onto the surfaces (25,000 cells/$cm^2$) for one hour at 37° C. The constructs/sleeves were then covered with endothelial cell growth media (MCDB-131 culture media supplemented with 2 mM L-glutamine, 2 ng/ml basic human fibroblast growth factor (hFGF), 10 ng/ml human endothelial growth factor (hEGF), 2 ng/ml insulin-like growth factor-I (IGF-I), 1 ng/ml vascular endothelial growth factor (VEGF), 1 µg/ml hydrocortisone, 50 µg/ml ascorbic acid, 5% FBS, 100 IU/ml penicillin, and 100 µg/ml streptomycin) and incubated for 12 hours at 37° C. The HCEC were labeled with Cell Tracker Green CMFDA, 5-chloromethyl fluorescein (Molecular Probes) and imaged on a Zeiss LSM confocal microscope.

Histology and Histochemistry

Evaluation of matrix fiber structure and cell organization were performed using histology and immunohistochemistry. While the hydrogel nature of the collagen constructs complicated the embedding and sectioning processes, satisfactory tissue slices were able to be obtained with slight additional effort. The methods outlined in this section detail the sample preparation, embedding, sectioning, staining, and visualization techniques.

Sample Preparation and Sectioning

Following each culturing period, constructs were washed in buffered saline to remove residual media. Ring sections were then cut from each sample and immersed in an Accustain 10% formalin solution (Sigma). The fixed sections were placed in plastic processing/embedding cassettes and cycled through a Pathcentre Enclosed Tissue Processor (Shandon Scientific Limited, Pittsburgh, Pa.) to dehydrate the specimens. Table 3.3 outlines the steps involved in the tissue processing protocol.

Once dehydrated, the samples were embedded in paraffin wax using a Histocentre 2 Tissue Embedding System (Shandon Scientific Limited) and sectioned into 5–6 µm slices on a HM355S Rotary Microtome (Microm, Waldorf, Germany) using an automatic feed and a disposable knife. Samples were sectioned in planes both parallel and perpendicular to the long axis of the tubular construct. Tissue slices were picked up from the knife using forceps and a paint brush and floated across the surface of a 45° C. water bath. The slices were then picked up onto Superfrost® Plus microscope slides (VWR, West Chester, Pa.) and dried at 45° C. for 2 hours. Once on slides, tissue slices were stored at room temperature until ready for staining.

TABLE 3.3

Tissue Processing Procedure for Histological Sectioning.

| Step | Procedure | Duration | Temperature |
|---|---|---|---|
| Step 1 | 70% Alcohol | 60 minutes | Ambient |
| Step 2 | 80% Alcohol | 60 minutes | Ambient |
| Step 3–5 | 95% Alcohol | 3 × 60 minutes | Ambient |
| Step 6–7 | 100% Alcohol | 2 × 60 minutes | Ambient |
| Step 8 | EtOH-Xylene | 60 minutes | Ambient |
| Step 9–10 | Xylene Substitute | 2 × 60 minutes | Ambient |
| Step 11–13 | Paraffin | 3 × 45 minutes | 60° C. |
| Total |  | ~12 hrs 15 min |  |

TABLE 3.4

H&E Staining Protocol.

| Step | Procedure | Duration |
|---|---|---|
| Steps 1–3 | Xylene Substitute | 3 × 3 minutes |
| Steps 4–6 | 100% Alcohol | 3 × 30 seconds |
| Step 7 | 80% Alcohol | 30 seconds |
| Step 8 | Tap Water | 1 minute |
| Step 9 | Hematoxylin | 4 minutes |
| Step 10 | Tap Water | 1 minute |
| Step 11 | Acid Alcohol | 1 second |
| Step 12 | Tap Water | 1 minute |
| Step 13 | Eosin Y | 1.5 minutes |
| Step 14 | 95% Alcohol | 30 seconds |
| Steps 15–17 | 100% Alcohol | 3 × 30 seconds |
| Steps 18–20 | Xylene Substitute | 3 × 30 seconds |
| Total |  | ~24 minutes |

Hematoxylin and Eosin Staining

Sectioned slides were deparaffinized and stained with hematoxylin and Eosin Y (H&E) using methods adapted from Richard-Allan Scientific (Seliktar 2000) and Advanced Tissue Sciences, Inc. (Saini 2001). A Varistain XY Automatic Stainer (Shandon Scientific Limited) set at mild agitation was employed to provide reproducibility. The individual steps involved in the staining process are outlined in Table 3.4. Hematoxylin and Eosin Y reagents were obtained from Richard-Allan Scientific (Kalamazoo, Mich.). Acid alcohol refers to 0.5% acetic acid in 70% ethanol. All other reagents were obtained Shandon Scientific Limited. Following the last staining step, specimens were mounted and coverslipped with 24×40 mm No. 1 coverslips. Excess mounting media was wiped away with a cloth soaked in xylene substitute and the slides were placed in a fume hood for several hours to dry before microscopic examination.

Verhoff Staining

Various techniques have been developed to identify elastic fibers in tissues. Verhoff's iodine-ferric chloride hemotoxylin is one of the more popular methods and has been shown to elicit fairly reproducible results. Slides were deparaffinized and rehydrated as in the H&E staining protocol. The slides were stained in an iodine-ferric hematoxylin solution (American Master Tech Scientific, Lodi, Calif.) for 20 minutes until the sections were perfectly black. The sections were then differentiated in 2% aqueous ferric chloride solution until the elastic fibers presented black against a colorless background. The ferric chloride was rinsed off in tap water (~5 minutes), and samples were counterstained in Van Gieson's stain (American Master Tech Scientific). Specimens were then washed in tap water, dehydrated, mounted, and coverslipped as in the H&E staining protocol.

Immunostaining

Structural organization of elastic fiber networks was also visualized via elastin immunostaining. Sections of constructs and tissue affixed to microscope slides were deparaffinized and rehydrated as described in the H&E staining protocol. Slides were incubated in a 5% horse serum saline solution for 60 minutes to block non-specific binding. A solution of mouse monoclonal anti-elastin antibody (Sigma, BA-4) diluted 1:50 in the horse serum blocking buffer was overlaid on top of each slide (~150 µl per slide). Slides were incubated at 37° C. in a humid environment for sixty minutes. Two saline washes followed by a 10 minute incubation in blocking buffer and two additional saline rinses were used to remove unbound antibody. A solution of FITC-conjugated goat anti-mouse secondary antibody diluted 1:50 in the horse serum blocking buffer was overlaid on top of each slide (~150 µl per slide). Again, two saline washes followed by a 10 minute incubation in blocking buffer and two additional saline rinses were used to remove unbound antibody. Slides were coverslipped using aqueous anti-fade mounting media and imaged using fluorescent microscopy. Images were collected within 24 hours to prevent signal loss.

Microscopic Examination

Examination of the stained histological sections was performed on a Zeiss Axiovert 200 microscope (Carl Zeiss, Inc.) using either a LD-A Plane 20×(0.30 NA) or a AChroplan 40×(0.65 NA) objective. Images were captured on a Kodak digital camera. Visualization of fluorescently labeled immunostained slides was accomplished on a Carl Zeiss LSM 510-model confocal microscope (Carl Zeiss, Inc.) using either a 10×(0.25 NA, 6.5 mm WD), 20×(0.30 NA, 2.2 mm WD), or 63×oil immersion (1.25 NA, 0.1 mm WD) objectives. Fluorescent samples were excited using Argon and HeNe lasers and images were collected using LSM 510 Version 2.02 software and saved in a TIFF file format.

Reverse-Transcriptase Polymerase Chain Reaction (RT-PCR)

Elastin message RNA gene transcripts were quantified through a competitive RT-PCR reaction with the BamHI/EcoRII fragment of the v-erbB gene (Clontech) which had been modified to contain gene-specific primer sequences. These primer sequences were designed using a Primer Premier 4 software package (Clontech) to ensure high template binding affinity and to minimize false priming, hairpin loops, and primer-dimerization. After PCR amplification, the modified v-erbB fragment, or PCR mimic fragment, was quantitated with a spectrophotometer at a 260 nm wavelength and aliquoted into serial dilutions ranging from 100 to 0.01 attomole/µL. The 9,306 Da oligomer sequence 5'-CGG CGC CTT CCC CGC AGT TAC CTT T-3' was used as the forward elastin primer. The 9,305 Da oligomer sequence 5'-ACA CAA CCC CTG GAA CCG CAG CAC C-3' was used as the reverse elastin primer.

Cell monolayers and three dimensional cell-seeded tissues were harvested for total RNA by disrupting the cell membranes with mechanical homogenization and RLT Buffer (Qiagen, Inc., Valencia, Calif.) containing β-mercaptoethanol. Samples were further homogenized by passing the lysate through a 25-G syringe needle five to ten times. One volume of 70% ethanol was added to the lysate and total RNA was isolated from each sample using Qiagen RNeasy columns and mini-kits. The samples were quantitated to assess the amounts of total RNA and tested for purity with a spectrophotometer at 260 nm and 280 nm wavelengths. Five micrograms of RNA from each sample were converted to cDNA with Avian Myeloblastosis Virus (AMV) reverse transcriptase (Promega, Madison, Wis.), purified with a phenol-chloroform extraction followed by an ethanol precipitation, and resuspended in 50 µl of RNase-free water. Competitive PCR reactions were run using equal volumes of sample cDNA and mimic fragment dilutions. Twenty-eight cycles (94° C., 30 sec dissociation; 63° C., 30 sec annealing; 72° C., 65 sec extension) were repeated using Taq DNA polymerase (Fisher) in PCR Buffer B (Fisher) with 0.2 mM dNTP, 2 mM of both forward and reverse primers, and 2 mM magnesium. The PCR products were separated by agarose gel electrophoresis and visualized with an UV transilluminator. Images of the DNA bands were captured with a CCD camera and quantitated using Gel-Pro Analyzer 3.0 software. Tropoelastin cDNA concentrations were considered to be equivalent to mimic fragment when the band intensities of the PCR products were balanced.

Immunoblotting

Immunoblotting techniques were used to detect the production of soluble elastin precursors. Concentrated samples were prepared from spent media and separated by molecular weight via SDS-polyacrylimide gel electrophoresis (SDS-PAGE). Proteins were then transferred onto nitrocellulose paper and probed for elastin with the BA-4 monoclonal antibody (Sigma) using standard Western blotting methods.

Sample Preparation and Ammonium Sulfate Precipitation

Spent media samples were separated into 1.7 ml aliquots in microcentrifuge tubes and combined with 30% ammonium sulfate (w:v) (Sigma). Samples were vortexed, incubated on ice overnight, and spun down at full speed (15,800 g) for 15 minutes at 4° C. The supernatants were carefully removed, and the pellets were resuspended with 100 µl DI water. Like samples were repooled together, loaded into 10,000 MWCO Slide-a-Lyzer dialysis cassettes (Pierce, Rockford, Ill.), and dialyzed against DI water for 24 hrs at 4° C. Following dialysis, samples were stored at −20° C. until ready for analysis.

SDS-PAGE and Protein Transfer

PAGE gels containing 5% stacking and 10% running acrylimide (BIO-RAD Laboratories, Hercules, Calif.) concentrations were constructed using standard fabrication protocols. Samples combined with loading buffer containing β-ME were heated at 90° C. for 3 minutes to remove secondary structural conformations and loaded into the gels (24 μl/lane). A mid-range molecular weight rainbow marker (BIO-RAD Laboratories) was used for molecular weight determination. The gels were run in an EC-140 gel electrophoresis box (E-C Apparatus Corporation, Holbrook, N.Y.) at 0.4 amps for 60 minutes using a BIO-RAD Power Pak 2000 power supply (BIO-RAD Laboratories). At the end of sixty minutes, bands from the molecular weight marker were distributed nicely throughout the length of the gel. When the blue running dye passed through the bottom of the gel, the system was taken down and the gels were processed for immunoblotting.

Protein transfer from the PAGE gels to Hybond ECL nitrocellular transfer paper was performed in an EC-140 Mini Blot Module (E-C Apparatus Corporation). Transfer modules were constructed as described in the E-C Apparatus instructions manual using sandwiches containing layers of filter paper and Scotch Brite™ sponge pads. Transfers were performed at 80 volts for 45 minutes. At the end of the transfer, bright bands from the lower weight marker proteins were visible on the nitrocellulose paper. Although the largest proteins may not have transferred completely, additional transfers resulted in the loss of smaller proteins through the nitrocellulose paper. Membranes were removed from the blotting apparatus and immediately placed in a 5% blocking buffer containing 5% dehydrated non-fat milk (w:v) in Tris Buffered Saline-Tween 20 (Sigma).

Immunoblotting and Antibody Incubations

Blocking was performed overnight at 4° C. under gentle agitation. The membranes were then covered with monoclonal anti-elastin mouse IgG antibody (Sigma, BA-4) which had been diluted 1:1,000 in a 2.5% non-fat milk TBS Tween blocking buffer at room temperature for 90 minutes. The membranes were washed 3×5 minutes in TBS-Tween and covered with the secondary HRP-conjugated anti-mouse antibody (1:1,000 dilution) (Amersham Pharmacia Biotech) in 2.5% blocking buffer at room temperature for 90 minutes. Three five-minute TBS-Tween washes were performed to remove the unbound antibody, and the protein sides of the membranes were covered with an ECL-Plus chemiluminescent solution (Amersham Pharmacia Biotech) for five minutes. At the end of the incubations, membrane papers were covered with plastic wrap and incubated with X-ray film (Kodak, Rochester, N.Y.) for 2 to 25 minutes. The film was processed and digitized using a 32-bit scanner. Images were saved as TIF files for data analysis.

Cyanogen Bromide (CNBr) Digestion

The degree of crosslinking in acellular sleeves was assessed using CNBr digestion. CNBr was added to 70% formic acid (Sigma) to form a 10 mg/ml solution. Sections of sleeves weighing 1.5–2.5 mg were immersed in the solution at approximately a 1:90 (w:v) ratio and incubated for 24 hours at 4° C. under gentle agitation. Sham digestions were performed in 70% formic acid as controls. Following the digestion, the samples were centrifuged briefly to pellet undissolved matrix and run on a 10% SDS-PAGE gel as described previously. The gels were removed from the electrophoresis apparatus and incubated in a colloidal Coomassie blue solution (BIO-RAD Laboratories) for 90 minutes followed by a 45-minute rinse in an acetic acid destaining solution. The gels were then rinsed overnight in DI water and imaged with a CCD camera.

It must be noted that, as used in this specification and the claims, the singular forms "a," "an," and "the" include plural referents unless the context clearly dictates otherwise. Thus, for example, reference to a vector composition containing "an agent" means molar quantities of such an agent.

It is to be understood that this invention is not limited to the particular combinations, methods, and materials disclosed herein as such combinations, methods, and materials may vary somewhat. It is also to be understood that the terminology employed herein is used for the purpose of describing particular embodiments only and is not intended to be limiting.

What is claimed is:

1. A tubular construct suitable for implantation, comprising, a biological support structure comprising a gel matrix admixed with a cellular composition comprising one or more types of cells and products of cells, and an intact elastin scaffold.

2. The tubular construct of claim 1, wherein the gel matrix comprises collagen.

3. The tubular construct of claim 1, wherein the gel matrix comprises fibrin.

4. The tubular construct of claim 1, wherein the cellular composition comprises smooth muscle cells.

5. The tubular construct of claim 1, wherein the cellular composition comprises altered or modified cells.

6. The tubular construct of claim 1, wherein the cellular composition and the intact elastin scaffold are derived from the same species.

7. A method of repair of soft tissue, comprising, implanting a tubular construct suitable for implantation, comprising, a biological support structure comprising a gel matrix admixed with a cellular composition comprising one or more types of cells and products of cells, and an intact elastin scaffold.

8. The method of claim 7, wherein the gel matrix comprises collagen.

9. The method of claim 7, wherein the gel matrix comprises fibrin.

10. The method of claim 7, wherein the cellular composition comprises smooth muscle cells.

11. The method of claim 7, wherein the cellular composition comprises altered or modified cells.

12. The method of claim 7, wherein the cellular composition and the intact elastin scaffold are derived from the same species.

13. A method for determining activity of agents, comprising, a) providing a tubular construct, comprising, a biological support structure comprising a gel metrix admixed with a cellular composition comprising one or more types of cells and products of cells, and an intact elastin scaffold, b) adding at least one agent to the tubular construct and c) determining an effect on the tubular construct.

14. The method of claim 13, wherein the gel matrix of the tubular construct comprises structural proteins collagen, fibrin, or elastin.

15. The method of claim 13, wherein the cellular composition comprises altered or modified cells.

* * * * *